United States Patent
Matsumoto et al.

(10) Patent No.: US 9,637,451 B2
(45) Date of Patent: May 2, 2017

(54) INDOLE COMPOUND

(71) Applicant: ASTELLAS PHARMA INC., Chuo-ku, Tokyo (JP)

(72) Inventors: Shunichiro Matsumoto, Tokyo (JP); Takafumi Shimizu, Tokyo (JP); Tomoyuki Saito, Tokyo (JP); Takatoshi Kanayama, Tokyo (JP); Hiroaki Tanaka, Tokyo (JP); Chiharu Mori, Tokyo (JP); Kazuhiro Yokoyama, Tokyo (JP); Shigeo Matsui, Tokyo (JP)

( * ) Notice: Subject to any disclaimer, the term of this patent is extended or adjusted under 35 U.S.C. 154(b) by 0 days.

(21) Appl. No.: 15/109,878

(22) PCT Filed: Jan. 13, 2015

(86) PCT No.: PCT/JP2015/050691
§ 371 (c)(1),
(2) Date: Jul. 6, 2016

(87) PCT Pub. No.: WO2015/108039
PCT Pub. Date: Jul. 23, 2015

(65) Prior Publication Data
US 2016/0332966 A1 Nov. 17, 2016

(30) Foreign Application Priority Data
Jan. 14, 2014 (JP) .................. 2014-004560

(51) Int. Cl.
*C07D 209/16* (2006.01)
*C07D 403/12* (2006.01)
*C07D 401/12* (2006.01)
*C07D 417/12* (2006.01)
*C07D 413/12* (2006.01)

(52) U.S. Cl.
CPC ......... *C07D 209/16* (2013.01); *C07D 401/12* (2013.01); *C07D 403/12* (2013.01); *C07D 413/12* (2013.01); *C07D 417/12* (2013.01)

(58) Field of Classification Search
None
See application file for complete search history.

(56) References Cited

U.S. PATENT DOCUMENTS

| 2004/0014969 A1 | 1/2004 | Decamps-Francois et al. |
| 2008/0027121 A1 | 1/2008 | Laudon et al. |
| 2010/0204276 A1 | 8/2010 | Marchand et al. |
| 2015/0203505 A1 | 7/2015 | Kanayama et al. |
| 2015/0368220 A1 | 12/2015 | Watanabe et al. |

FOREIGN PATENT DOCUMENTS

| WO | 9732871 A1 | 9/1997 |
| WO | 2006078006 A1 | 7/2006 |
| WO | 2008049997 | * 5/2008 |
| WO | 2014010602 A1 | 1/2014 |
| WO | 2014010603 A1 | 1/2014 |

OTHER PUBLICATIONS

Treatments and drugs at <http://www.mayoclinic.org/diseases-conditions/urinary-incontinence/basics/treatment/con-20037883>> visited Sep. 7, 2016.*
Spadoni et al., ChemMedChem 2006, 1, 1099-1105.*
Database Caplus Chemical Abstracts Service, Columbus, Ohio, US; Database Accession No. 2008:505155, Abstract of WO 2008049997, Les Laboratoires Servier, Fr., Marchand et al., May 2, 2008.*
Database Caplus Chemical Abstracts Service, Columbus, Ohio, US; Database Accession No. 2014:720310, Abstract of CN 103755686, China Pharmaceutical University, Peop. Rep. China; Shandong Yi-Kang Pharmaceutical Co., Ltd., Apr. 30, 2014.*
Xie et al., European Journal of Medicinal Chemistry 102 (2015) 363-374.*
Koki K. et al.: "Neurochemical Properties of Ramelteon (TAK-375), a Selective MT1/MT2 Receptor agonist", Neuropharmacology, vol. 48, pp. 301-310, (2005).
Miyomoto, M. et al.:"Behavioral Pharmacology of Ramelteon (TAK-375) in Small Mammals", Annals of Neurology. vol. 54 (Suppl 7), p. S46, #104, (2003).
Markl et al., "N-Acetyl-5-arylalkoxytryptamine Analogs: Probing the Melatonin Receptors for MT1-Selectivity", Arch. Pharma. Chem. Life Sci., vol. 344, pp. 666-674, (2011).

(Continued)

*Primary Examiner* — Karl J Puttlitz

(57) ABSTRACT

[Problem]
To provide a compound useful as a $MT_1$ and/or $MT_2$ receptor agonist.
[Solution]
The present inventors have studied on $MT_1$ and/or $MT_2$ receptor agonists, and have confirmed that indole compounds have the activity. As a result, the present invention is accomplished. That is, a compound represented by formula (I) or a salt thereof according to the present invention has a $MT_1$ and/or $MT_2$ receptor agonistic activity and has a low ability of migrating into central nervous system. Therefore, the compound or a salt thereof can be used as a peripheral $MT_1$ and/or $MT_2$ receptor agonist, and therefore can be used as a therapeutic and/or prophylactic agent for urinary incontinence, particularly stress urinary incontinence and mixed urinary incontinence.

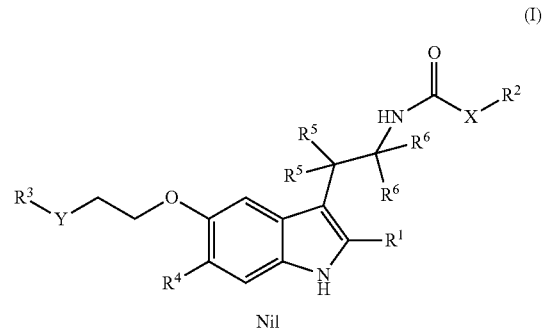

17 Claims, No Drawings

(56) References Cited

OTHER PUBLICATIONS

Spadoni et al., "Towards the Development of Mixed MT1-Agonist/MT2-Antagonist Melatonin Receptor Ligands", ChemMedChem, vol. 1, pp. 1099-1105, (2006).
Gomez-Pinilla et al., "Effect of Melatonin on Age Associated Changes in Guinea Pig Bladder Function", The Journal of Urology, vol. 177, pp. 1558-1561, (2007).
PCT/JP2015/050691 (WO2015/108039): Written Opinion of the International Search Authority and International Search Report (2015). (English Translation of International Search Report provided).

* cited by examiner

INDOLE COMPOUND

TECHNICAL FIELD

The present invention relates to an indole compound which is useful as an active ingredient for a pharmaceutical composition, for example, a pharmaceutical composition for treating or preventing urinary incontinence.

BACKGROUND ART

Urinary incontinence is a condition in which involuntary leakage of urine is involved and recognized objectively and these become social or hygienic problems (Journal of Clinical Pharmacy and Therapeutics, 25, 251-263 (2000)). As typical examples of urinary incontinence, stress urinary incontinence, urge urinary incontinence, functional urinary incontinence, reflex urinary incontinence, overflow urinary incontinence, a mixed type of urinary incontinence which involves stress urinary incontinence and urge urinary, and the like have been known.

The most common type of the urinary incontinence is stress urinary incontinence and it has been reported that 50% of women suffering from the urinary incontinence is stress urinary incontinence (International Urogynecology Journal, 11 (5), 301-319 (2000)). The stress urinary incontinence refers to a disease in which when abdominal pressure rises during coughing, sneezing, exercise, or the like, urine leaks out involuntarily even though there is no contraction of the bladder. The causes of stress urinary incontinence can be largely divided into two types. One is the bladder neck/urethra hypermobility, in which the transmission of abdominal pressure to the urethra fails due to bladder neck ptosis, based on the pelvic floor muscle relaxation, and thus only the intravesical pressure rises during the rise of abdominal pressure and urine leaks. The other is that the reduction of a sphincter muscle function due to intrinsic sphincter deficiency causes urine leakage when the abdominal pressure rises. There is a high possibility that the onset of stress urinary incontinence involves weakening of the pelvic floor muscles due to aging and childbirth, and deterioration of the urethral function. In particular, the trauma of the pelvis by pregnancy and vaginal childbirth is known as a risk factor for a persistent stress urinary incontinence onset, and it has been reported that a prevalence rate of stress urinary incontinence for five years after the first birth is about 30% (Neurourology and Urodynamics, 21 (1), 2-29 (2002)).

Urge urinary incontinence is a disease in which urine leaks involuntarily immediately after a complaint of a strong suddenly occurring and irrepressible desire to urinate which is hard to endure (urge and sudden desire of urination). The mixed type of urinary incontinence is a condition in which a combination of plural types of urinary incontinence is developed, and most of them involve development of urge urinary incontinence and stress urinary incontinence.

Urinary incontinence has a major impact on the quality of life (QOL). Concerns about its symptoms restrict the range of activities of patients, making the patients feel loneliness and social isolation.

As a therapeutic drug for stress urinary incontinence, duloxetine having a serotonin-norepinephrine reuptake inhibitory action (SNRI) has been reported (International Urogynecology Journal, 14, 367-372 (2003)).

Duloxetine has been reported to be effective against stress urinary incontinence in clinical trials, but has also been reported to have side effects such as nausea, insomnia, and dizziness (BJU International, 94, 31-37 (2004)).

In the neuroreflex of the autonomic nerves by stretch stimulus of the bladder in the urine storage phase, an $\alpha_1$ adrenoceptor is present in the urethra and plays a role to maintain continence by inducing urethral contraction. To date, it has been reported that a plurality of drugs having $\alpha_1$ adrenoceptor agonistic actions have a strong urethral contraction action, and in clinical trials, a drug having an $\alpha_1$ adrenoceptor agonistic action is effective against stress urinary incontinence (Journal of Clinical Pharmacy and Therapeutics, 25, 251-263 (2000), International Urogynecology Journal, 14, 367-372 (2003), Urology, 62 (Sup 4 A), 31-38 (2003), and BJU International, 93, 162-170 (2004)). However, it has been known that an $\alpha_1$ adrenoceptor agonist has cardiovascular side effects such as increased blood pressure or the like (International Urogynecology Journal, 14, 367-372 (2003) and BJU International, 93, 162-170 (2004)).

As described above, it is considered that as a drug treatment for stress urinary incontinence, it is effective to increase the urethral resistance so as to maintain continence when intravesical pressure rises during the urine storage phase, and thus, drugs based on some mechanisms of action have been studied. However, there is a strong desire for the development of an agent for treating stress urinary incontinence, based on a novel mechanism of action with fewer side effects.

Meanwhile, melatonin represented by the following formula is a hormone secreted by the pineal gland, which exhibits an inhibitory effect on the function and growth of gonad. Melatonin affects the circadian rhythm in animals, and plays a role to tune the reproductive function to a light cycle of the environment.

[Chem. 1]

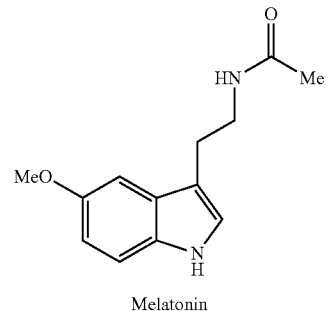

Melatonin

As the receptors of melatonin, there have been known three subtypes, $MT_1$, $MT_2$, and $MT_3$ (Cell and Tissue Research, 309, 151-162 (2002) and Journal of Biological Chemistry 275, 31311-31317 (2000)). $MT_1$ and $MT_2$ are G protein-coupled receptors (GPCR) which are coupled to Gi and Gq, but $MT_3$ is a quinone reductase (QR2) which has a melatonin binding site. The affinity of melatonin for the $MT_1$ and $MT_2$ receptors is high, but the affinity of melatonin for the $MT_3$ receptor is low (Journal of Biological Chemistry 275, 31311-31317 (2000)).

Incidentally, there have been a number of reports that $MT_1$ and/or $MT_2$ receptor agonists are useful for the treatment of central nervous system diseases such as sleeping disorders and depression.

As the representative $MT_1$ and/or $MT_2$ receptor agonists, the following compounds have been reported.

A compound represented by the following formula (A) has an $MT_1$ and $MT_2$ receptor agonistic activity and can be used for preventing or treating sleep-awake rhythm disorders, jet lag, abnormality of physical conditions due to work in three shifts or the like, seasonal depression disorder, reproductive and neuroendocrine diseases, senile dementia, Alzheimer's disease, various disorders due to aging, cerebral circulatory disorder, head injury, spinal cord injury, stress, epilepsy, convulsions, anxiety, depression, Parkinson's disease, hypertension, glaucoma, cancer, insomnia, diabetes mellitus, and the like. The compound has been reported to have properties of modulating immunomodulation, intelligence, tranquilizers, and ovulation control (Patent Document 1). In particular, ramelteon represented by the following formula has been known as an agent for treating insomnia characterized by hypnagogic disorder (Non-Patent Documents 1 and 2).

[Chem. 2]

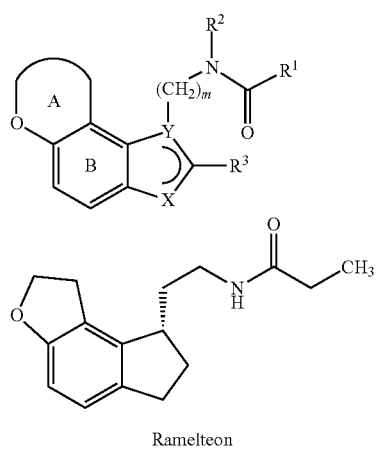

Ramelteon (Refer to this publication for the symbols in the formula.)

It has been described that a compound represented by the formula (B) has an affinity for a melatonin receptor and is useful for the treatment of stress, sleeping disorders, anxiety, seasonal affective disorder or major depression, cardiovascular pathology, digestive system pathology, insomnia and fatigue due to jet lag, schizophrenia, panic attacks, depression, appetite disorders, obesity, insomnia, mental disorders, epilepsy, diabetes mellitus, Parkinson's disease, senile dementia, various disorders caused by normal or pathological aging, migraine, memory loss, and Alzheimer's disease, is useful against cerebral circulation disorders, is useful for the treatment of hypogonadism, has anovulation and immunomodulatory characteristics, and is useful in the application for the treatment of cancer (Patent Document 2).

[Chem. 3]

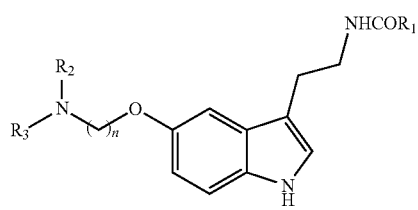

(In the formula, $R_1$ represents a $C_{1-6}$ alkyl group or the like, $R_2$ and $R_3$ are combined with a nitrogen atom to which they are bonded to form 5- to 8-membered heterocycle, in which the heterocycle does not contain an additional hetero atom, and n represents an integer of 2 to 6.)

It has been described that some compounds including compounds represented by the following formulae (C) and (D) have an affinity for $MT_1$ and $MT_2$ receptors (Non-Patent Document 3).

[Chem. 4]

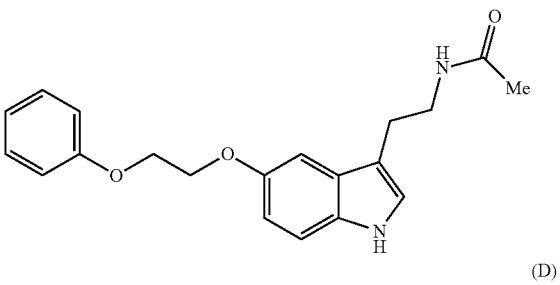

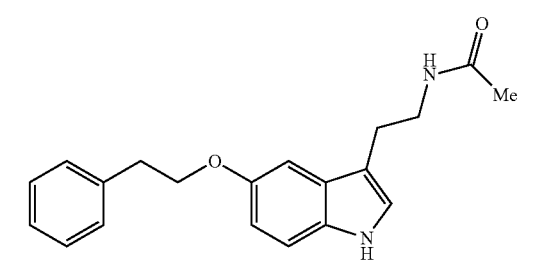

It has been described that some compounds including compounds represented by the following formulae (E) and (F) have an affinity for $MT_1$ and $MT_2$ receptors (Non-Patent Document 4).

[Chem. 5]

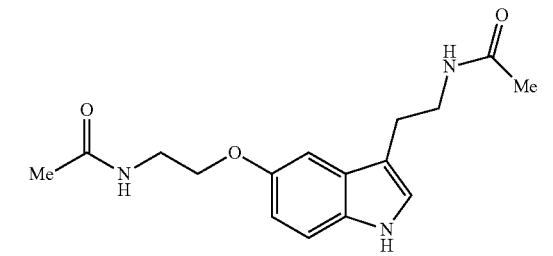

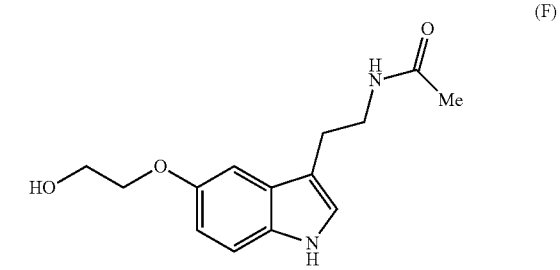

It has been described that a compound represented by the formula (G) has an affinity for $MT_1$ and $MT_2$ receptors, is useful for the treatment of stress, sleeping disorders, anxiety, seasonal affective disorder or major depression, cardiovascular pathology, digestive system pathology, insomnia and fatigue due to jet lag, schizophrenia, panic attacks, depression, appetite disorders, obesity, insomnia, pain, mental disorders, epilepsy, diabetes mellitus, Parkinson's disease, senile dementia, various disorders caused by normal or pathological aging, migraine, memory loss, and Alzheimer's disease, is useful against cerebral circulation disorders, is useful for the treatment of hypogonadism, has anovulation and immunomodulatory characteristics, and can be used for the treatment of cancer (Patent Document 3).

[Chem. 6]

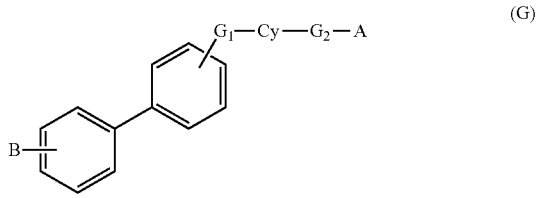

(G)

(In the formula, $G_1$ represents —X'—$(CH_2)_n$—X—$(CH_2)_m$—X"—, X represents $CH_2$ or the like, X' and X" each represent an oxygen atom or the like, n and m each represent the same or different integers of 0 to 5, Cy represents indole or the like, the indole has a substituent such as a hydrogen atom and a lower alkyl at the 2-position and is bonded to $G_2$ from the 3-position, $G_2$ represents a chain containing 1 to 6 carbon atoms which may be substituted with at least one group such as halogen, A represents NRCOR' or the like, and R and R' each represent a hydrogen atom, a $C_{1-6}$ alkyl group, or the like. Refer to this publication for the other symbols.)

Furthermore, a compound represented by the following formula (H), which has a peripheral $MT_1$ and/or $MT_2$ receptor agonistic activity and is useful against urological diseases, in particular, stress urinary incontinence, has been reported (Patent Document 4).

[Chem. 7]

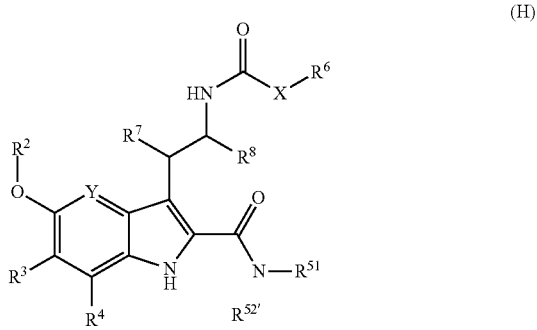

(H)

(In the formula, Y is N or $CR^1$, $R^1$, $R^3$, and $R^4$ are the same as or different from each other and are lower alkyl which may be substituted, H, or halogen, $R^2$ is lower alkyl which may be substituted with at least one substituent selected from a group consisting of halogen and cyano, and further, $R^2$ may be combined with $R^1$ to form —$(CH_2)_n$— or $R^2$ may be combined with $R^3$ to form —$(CH_2)_n$—, n is 2 or 3, X is a bond, —$NR^{11}$—, or —$NR^{11}$—O—, and $R^6$ represents lower alkyl which may be substituted, cycloalkyl which may be substituted, or the like. Refer to this publication for the other symbols.)

In addition, it has been described that melatonin, ramelteon, agomelatine, tasimelteon, and TIK-301, which are compounds having a melatonin receptor activating action, contract the isolated urethra in a rat to increase the urethral pressure of the rat (Patent Document 5).

RELATED ART

Patent Document

[Patent Document 1] WO 97/032871
[Patent Document 2] WO 2008/049997
[Patent Document 3] WO 2002/022555
[Patent Document 4] WO 2014/010602
[Patent Document 5] WO 2014/010603

Non-Patent Document

[Non-Patent Document 1] Neuropharmacology, 48, 301-310 (2005)
[Non-Patent Document 2] Annals of Neurology, 54 (suppl 7), S46-48 (2003)
[Non-Patent Document 3] Arch. Pharm. Chem. Life Sci., 344, 666-674, (2011)
[Non-Patent Document 4] Chem Med Chem, 1, 1099-1105 (2006)

DISCLOSURE OF INVENTION

Problems to be Solved by the Invention

The present invention provides a compound which is useful as an active ingredient for a pharmaceutical composition, for example, a pharmaceutical composition for treating or preventing urinary incontinence based on a novel mechanism of action.

Means for Solving the Problems

The present inventors have conducted extensive studies to achieve a creation of a drug for treating urinary incontinence based on a novel mechanism of action, and as a result, they have found that ramelteon described above, which is a representative $MT_1$ and/or $MT_2$ receptor agonist, exhibits a urethra contractile action via $MT_1$ and/or $MT_2$ receptor, and the $MT_1$ and/or $MT_2$ receptor agonist is useful for the treatment or prevention of urinary incontinence (WO 2014/010602 and WO 2014/010603). Each of known $MT_1$ and/or $MT_2$ receptor agonists has an action against diseases in the central nervous system, such as sleeping disorders, depression or the like. Thus, it has been contemplated that in the case where the $MT_1$ and/or $MT_2$ receptor agonists are used for the treatment or prevention of urinary incontinence, it is preferable to separate the action on urinary incontinence and the action on the diseases in the central nervous system, since it is not preferable that the agonists exhibit an action of the diseases in the central nervous system (including, for example, a sleep action) when administered at an effective dose. Therefore, the present inventors have further conducted extensive studies to achieve a creation of a compound having a strong action on urinary incontinence.

As a result, the present inventors have found that an indole compound of the formula (I) has a peripheral and excellent MT$_1$ and/or MT$_2$ receptor agonistic activity and is useful as a drug for treating or preventing urinary incontinence, thereby completing the present invention.

That is, the present invention relates to a compound of the formula (I) or a salt thereof, as well as a pharmaceutical composition comprising the compound of the formula (I) or a salt thereof and a pharmaceutically acceptable excipient.

[Chem. 8]

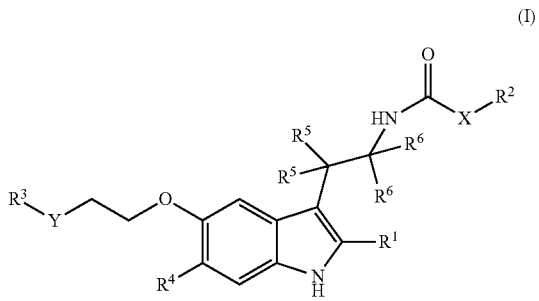

(I)

(In the formula,
$R^1$ is H or $C_{1-6}$ alkyl which may be substituted,
X is a bond, —NH—, or —N($C_{1-6}$ alkyl)-,
$R^2$ is $C_{1-6}$ alkyl which may be substituted,
Y is a bond, —CH$_2$—, —NH—, or —O—,
$R^3$ is 5- to 6-membered heteroaryl which may be substituted, and when Y is a bond, $R^3$ may further be —NR$^{31}$—CO—O—R$^{32}$,
$R^{31}$ is H or $C_{1-6}$ alkyl,
$R^{32}$ is $C_{1-6}$ alkyl,
$R^4$ is H, $C_{1-6}$ alkyl which may be substituted, or halogen,
$R^5$'s are the same as or different from each other, and are H or $C_{1-6}$ alkyl which may be substituted, and
$R^6$'s are the same as or different from each other and are H or $C_{1-6}$ alkyl which may be substituted.)

In addition, unless otherwise specified, when symbols in a certain chemical formula in the present specification are also used in another chemical formula, the same symbol represents the same meaning.

The present invention particularly relates to a compound of the above formula (I) specified by the following definition or a salt thereof, as well as a pharmaceutical composition comprising the compound of the formula (I) or a salt thereof and a pharmaceutically acceptable excipient:

in the formula,
$R^1$ is H or $C_{1-6}$ alkyl,
X is a bond, —NH—, or —N($C_{1-6}$ alkyl)-,
$R^2$ is $C_{1-6}$ alkyl which may be substituted with 1 to 3 halogens,
Y is a bond or —O—, wherein
(i) when Y is —O—, $R^3$ is 5- to 6-membered heteroaryl having at least one hetero atom selected from a group consisting of O, S, and N,
(ii) when Y is a bond, $R^3$ is 5-membered heteroaryl having at least two hetero atoms selected from a group consisting of O, S, and N,
the heteroaryl represented by above (i) and (ii) may be substituted with 1 to 3 substituents selected from a group consisting of $C_{1-6}$ alkyl which may be substituted with 1 to 3 substituents selected from a group consisting of —OH, —O—($C_{1-6}$ alkyl), and halogen; —O—($C_{1-6}$ alkyl); $C_{3-8}$ cycloalkyl; and halogen, when Y is a bond, $R^3$ may further be —NR$^{31}$—CO—O—R$^{32}$,
$R^{31}$ is H or $C_{1-6}$ alkyl,
$R^{32}$ is $C_{1-6}$ alkyl,
$R^4$ is H or halogen,
$R^5$'s are the same as or different from each other, and are H or $C_{1-6}$ alkyl, and
$R^6$'s are the same as or different from each other and are H or $C_{1-6}$ alkyl.)

The present invention relates to a pharmaceutical composition, in particular, a pharmaceutical composition for treating or preventing urinary incontinence, comprising the compound of the formula (I) or a salt thereof. Further, the pharmaceutical composition includes a pharmaceutical composition, in particular, a pharmaceutical composition for treating or preventing urinary incontinence, comprising the compound of the formula (I) or a salt thereof and a pharmaceutically acceptable excipient, and an agent for treating or preventing urinary incontinence, comprising the compound of the formula (I) or a salt thereof.

The present invention relates to use of the compound of the formula (I) or a salt thereof for the manufacture of a pharmaceutical composition for treating or preventing urinary incontinence; use of the compound of the formula (I) or a salt thereof for treating or preventing urinary incontinence; the compound of the formula (I) or a salt thereof for treating or preventing urinary incontinence; and a method for treating or preventing urinary incontinence, comprising administering to a subject an effective amount of the compound of the formula (I) or a salt thereof. Meanwhile, the term "subject" is a human being or other animals in need of treatment or prevention thereof, and according to a certain embodiment, a human being in need of treatment or prevention thereof.

Effects of the Invention

The compound of the formula (I) or a salt thereof is a compound which acts as a peripheral MT$_1$ and/or MT$_2$ receptor agonist and it is possible to separate the action on urinary incontinence and the action on the central nervous system disease. The compound of the formula (I) or a salt thereof can be used as an active ingredient for a pharmaceutical composition for treating or preventing urinary incontinence, and preferably stress urinary incontinence and a mixed type of urinary incontinence.

EMBODIMENTS FOR CARRYING OUT THE INVENTION

Hereinafter, the present invention will be described in detail.

In the present specification, the "urinary incontinence" is a disease in which urine leaks out involuntarily, and examples thereof include stress urinary incontinence, urge urinary incontinence, a mixed type of urinary incontinence, functional urinary incontinence, and reflex urinary incontinence.

The "stress urinary incontinence" is a disease in which when abdominal pressure rises during coughing, sneezing, exercise, or the like, urine leaks out involuntarily even though there is no contraction of the bladder. The "urge urinary incontinence" is a disease in which urine leaks involuntarily immediately after a complaint of a strong suddenly occurring and irrepressible desire to urinate which is hard to endure (urge and sudden desire of urination). The mixed type of urinary incontinence is a disease which involves development of the urge urinary incontinence and the stress urinary incontinence.

The use of the pharmaceutical composition of the present invention is urinary incontinence; in another embodiment, stress urinary incontinence or a mixed type of urinary incontinence; in a further other embodiment, stress urinary incontinence; and in a still further embodiment, a mixed type of urinary incontinence.

In the present specification, the "$MT_1$ and/or $MT_2$ receptor" mean(s) "an $MT_1$ receptor and an $MT_2$ receptor", or "an $MT_1$ receptor".

The "$C_{1-6}$ alkyl" is linear or branched alkyl having 1 to 6 carbon atoms (which is hereinafter simply referred to as $C_{1-6}$), for example, methyl, ethyl, n-propyl, isopropyl, n-butyl, isobutyl, sec-butyl, tert-butyl, n-pentyl, or n-hexyl; in another embodiment, $C_{1-3}$ alkyl; in a further embodiment, methyl, ethyl, or n-propyl; in a still further embodiment, methyl or ethyl; in a still further embodiment, methyl; and in a still further embodiment, ethyl.

The "halogen" means F, Cl, Br, or I; preferably, F, Cl, or Br; more preferably, F or Cl; and further more preferably, F.

The "$C_{3-8}$ cycloalkyl" is a $C_{3-8}$ saturated hydrocarbon ring group; specifically, cyclopropyl, cyclobutyl, cyclopentyl, cyclohexyl, cycloheptyl, or cyclooctyl; in another embodiment, $C_{3-6}$ cycloalkyl; and in a further embodiment, cyclopropyl.

The "5- to 6-membered heteroaryl having at least one hetero atom selected from a group consisting of O, S, and N" is 5- to 6-membered monocyclic heteroaryl having at least one hetero atom selected from a group consisting of oxygen, sulfur and nitrogen as a ring atom, in which examples of the 6-membered heteroaryl include pyridyl, pyrazinyl, pyrimidinyl, pyridazinyl, and the like, and examples of the 5-membered heteroaryl include imidazolyl, triazolyl, tetrazolyl, thiazolyl, pyrazolyl, isothiazolyl, oxazolyl, isoxazolyl, thiadiazolyl, oxadiazolyl, thienyl, furyl, pyrrolyl, and the like. In a certain embodiment, the "5- to 6-membered heteroaryl having at least one hetero atom selected from a group consisting of O, S, and N" is pyridyl, pyrazinyl, pyrimidinyl, thiazolyl, pyrazolyl, or isoxazolyl; in another embodiment, pyridyl, pyrazinyl, pyrimidinyl, pyrazolyl, or isoxazolyl; in a further embodiment, pyridyl or pyrazolyl; and in a still further embodiment, pyrazolyl.

Further, the "5-membered heteroaryl having at least two hetero atoms selected from a group consisting of O, S, and N" is 5-membered heteroaryl of the "5- to 6-membered heteroaryl having at least one hetero atom selected from a group consisting of O, S, and N", as described above having at least two hetero atoms as a ring atom; in a certain embodiment, imidazolyl, triazolyl, tetrazolyl, thiazolyl, pyrazolyl, isothiazolyl, oxazolyl, isoxazolyl, thiadiazolyl, or oxadiazolyl; in another embodiment, thiazolyl, pyrazolyl, or isoxazolyl; in a further embodiment, thiazolyl or pyrazolyl; and in a still further embodiment, pyrazolyl.

In the present specification, the expression "which may be substituted" represents "which is not substituted" or "which has at least one substituent". For example, the "which may be substituted with 1 to 3 substituents" means "which is not substituted" or "which is substituted with 1, 2, or 3 substituents". Further, in the case having a plurality of substituents, the substituents may be the same as or different from each other.

In a certain embodiment, the substituent of "$C_{1-6}$ alkyl which may be substituted" in $R^1$, $R^2$, $R^4$, $R^5$, and $R^6$ is $C_{1-6}$ alkyl which may be substituted with 1 to 3 substituents selected from a group consisting of —OH, —O—($C_{1-6}$ alkyl), and halogen; —O—($C_{1-6}$ alkyl); $C_{3-8}$ cycloalkyl; and halogen.

In a certain embodiment, the substituent of "5- to 6-membered heteroaryl which may be substituted" in $R^3$ is $C_{1-6}$ alkyl which may be substituted with 1 to 3 substituents selected from a group consisting of —OH, —O—($C_{1-6}$ alkyl), and halogen; —O—($C_{1-6}$ alkyl); $C_{3-8}$ cycloalkyl; and halogen, in another embodiment, $C_{1-6}$ alkyl which may be substituted with 1 to 3 halogens; —O—($C_{1-6}$ alkyl); $C_{3-8}$ cycloalkyl; or halogen, in another embodiment, $C_{1-6}$ alkyl which may be substituted with 1 to 3 halogens; —O—($C_{1-6}$ alkyl); or halogen, in a further embodiment, $C_{1-6}$ alkyl which may be substituted with 1 to 3 halogens; or halogen, in a still further embodiment, methyl, ethyl, n-propyl, methoxy, trifluoromethyl, cyclopropyl, F, Cl, or Br, in a still further embodiment, methyl, ethyl, trifluoromethyl, or Cl, in a still further embodiment, methyl, methoxy, or trifluoromethyl, in a still further embodiment, methyl or methoxy, in a still further embodiment, methyl or trifluoromethyl, and in a still further embodiment, methyl.

Certain embodiments of the compound of the formula (I) of the present invention are shown below.

(1) The compound or a salt thereof, in which $R^1$ is H or $C_{1-6}$ alkyl which may be substituted.

(1-1) The compound or a salt thereof, in which $R^1$ is H or $C_{1-6}$ alkyl.

(1-2) The compound or a salt thereof, in which $R^1$ is H or methyl.

(1-3) The compound or a salt thereof, in which $R^1$ is H.

(1-4) The compound or a salt thereof, in which $R^1$ is methyl.

(2) The compound or a salt thereof, in which X is a bond, —NH—, or —N($C_{1-6}$ alkyl)-.

(2-1) The compound or a salt thereof, in which X is a bond or —NH—.

(2-2) The compound or a salt thereof, in which X is a bond.

(2-3) The compound or a salt thereof, in which X is —NH—.

(3) The compound or a salt thereof, in which $R^2$ is $C_{1-6}$ alkyl which may be substituted.

(3-1) The compound or a salt thereof, in which $R^2$ is $C_{1-6}$ alkyl which may be substituted with 1 to 3 halogens.

(3-2) The compound or a salt thereof, in which $R^2$ is $C_{1-6}$ alkyl which may be substituted with 1 to 3 F.

(3-3) The compound or a salt thereof, in which $R^2$ is $C_{1-6}$ alkyl.

(3-4) The compound or a salt thereof, in which $R^2$ is methyl, ethyl, n-propyl, or difluoromethyl.

(3-5) The compound or a salt thereof, in which $R^2$ is methyl or ethyl.

(3-6) The compound or a salt thereof, in which $R^2$ is ethyl.

(3-7) The compound or a salt thereof, in which $R^2$ is methyl.

(4) The compound or a salt thereof, in which Y is a bond, —$CH_2$—, —NH—, or —O—.

(4-1) The compound or a salt thereof, in which Y is a bond or —O—.

(4-2) The compound or a salt thereof, in which Y is a bond.

(4-3) The compound or a salt thereof, in which Y is —O—.

(5) The compound or a salt thereof, in which $R^3$ is 5- to 6-membered heteroaryl which may be substituted, provided that when Y is a bond, $R^3$ may further be —$NR^{31}$—CO—O—$R^{32}$, $R^{31}$ is H or $C_{1-6}$ alkyl, and $R^{32}$ is $C_{1-6}$ alkyl.

(5-1) The compound or a salt thereof, in which (i) when Y is —O—, $R^3$ is 5- to 6-membered heteroaryl having at least one hetero atom selected from a group consisting of O, S, and N, or (ii) when Y is a bond, $R^3$ is 5-membered heteroaryl having at least two hetero atoms selected from a group consisting of O, S, and N, the heteroaryl may be substituted with 1 to 3 substituents selected from a group consisting of $C_{1-6}$ alkyl which may be substituted with 1 to 3 substituents selected from a group consisting of —OH, —O—($C_{1-6}$ alkyl), and halogen; —O—($C_{1-6}$ alkyl); $C_{3-8}$ cycloalkyl; and halogen, when Y is a bond, $R^3$ may further be —$NR^{31}$—CO—O—$R^{32}$, and $R^{31}$ is H or $C_{1-6}$ alkyl, and $R^{32}$ is $C_{1-6}$ alkyl.

(5-2) The compound or a salt thereof, in which (i) when Y is —O—, $R^3$ is heteroaryl selected from a group consisting of pyridyl, pyrazinyl, pyrimidinyl, thiazolyl, pyrazolyl, and isoxazolyl, or (ii) when Y is a bond, $R^3$ is heteroaryl selected from a group consisting of thiazolyl, pyrazolyl, and isoxazolyl, the heteroaryl represented by above (i) and (ii) may be substituted with 1 to 3 substituents selected from a group consisting of $C_{1-6}$ alkyl which may be substituted with 1 to 3 halogens; —O—($C_{1-6}$ alkyl); $C_{3-8}$ cycloalkyl; and halogen, when Y is a bond, $R^3$ may further be —NH—CO—O—$R^{32}$, and $R^{32}$ is $C_{1-6}$ alkyl.

(5-3) The compound or a salt thereof, in which (i) when Y is —O—, $R^3$ is 5- to 6-membered heteroaryl selected from a group consisting of pyridyl, pyrazinyl, pyrimidinyl, pyrazolyl, and isoxazolyl, the 5- to 6-membered heteroaryl may be substituted with 1 to 3 substituents selected from a group consisting of $C_{1-6}$ alkyl which may be substituted with 1 to 3 halogens; —O—($C_{1-6}$ alkyl); $C_{3-8}$ cycloalkyl; and halogen, or (ii) when Y is a bond, $R^3$ is 5-membered heteroaryl selected from a group consisting of thiazolyl and pyrazolyl, and the 5-membered heteroaryl may be substituted with 1 to 3 substituents selected from a group consisting of $C_{1-6}$ alkyl which may be substituted with 1 to 3 halogens; and halogen, when Y is a bond, $R^3$ may further be —NH—CO—O—$R^{32}$, and $R^{32}$ is $C_{1-3}$ alkyl.

(5-4) The compound or a salt thereof, in which (i) when Y is —O—, $R^3$ is 5- to 6-membered heteroaryl having at least one hetero atom selected from a group consisting of O, S, and N, or (ii) when Y is a bond, $R^3$ is 5-membered heteroaryl having at least two hetero atoms selected from a group consisting of O, S, and N, and the heteroaryl represented by above (i) and (ii) may be substituted with 1 to 3 substituents selected from a group consisting of $C_{1-6}$ alkyl which may be substituted with 1 to 3 substituents selected from a group consisting of —OH, —O—($C_{1-6}$ alkyl), and halogen; —O—($C_{1-6}$ alkyl); $C_{3-8}$ cycloalkyl; and halogen.

(5-5) The compound or a salt thereof, in which (i) when Y is —O—, $R^3$ is heteroaryl selected from a group consisting of pyridyl, pyrazinyl, pyrimidinyl, thiazolyl, pyrazolyl, and isoxazolyl, or (ii) when Y is a bond, $R^3$ is heteroaryl selected from a group consisting of thiazolyl, pyrazolyl, and isoxazolyl, and the heteroaryl may be substituted with 1 to 3 substituents selected from a group consisting of $C_{1-6}$ alkyl which may be substituted with 1 to 3 halogens; —O—($C_{1-6}$ alkyl); $C_{3-8}$ cycloalkyl; and halogen.

(5-6) The compound or a salt thereof, in which (i) when Y is —O—, $R^3$ is 5- to 6-membered heteroaryl selected from a group consisting of pyridyl, pyrazinyl, pyrimidinyl, pyrazolyl, and isoxazolyl, the 5- to 6-membered heteroaryl may be substituted with 1 to 3 substituents selected from a group consisting of $C_{1-6}$ alkyl which may be substituted with 1 to 3 halogens; —O—($C_{1-6}$ alkyl); $C_{3-8}$ cycloalkyl; and halogen, or (ii) when Y is a bond, $R^3$ is 5-membered heteroaryl selected from a group consisting of thiazolyl and pyrazolyl, and the 5-membered heteroaryl may be substituted with 1 to 3 substituents selected from a group consisting of $C_{1-6}$ alkyl which may be substituted with 1 to 3 halogens; and halogen.

(5-7) The compound or a salt thereof, in which (i) when Y is —O—, $R^3$ is pyridyl or pyrazolyl; or (ii) when Y is a bond, $R^3$ is pyrazolyl, and the pyridyl and the pyrazolyl may be substituted with 1 to 3 substituents selected from a group consisting of $C_{1-6}$ alkyl which may be substituted with 1 to 3 halogens; and —O—($C_{1-6}$ alkyl).

(5-8) The compound or a salt thereof, in which (i) when Y is —O—, $R^3$ is pyridyl substituted with one substituent selected from a group consisting of methyl and methoxy, or pyrazolyl substituted with one methyl; or (ii) when Y is a bond, $R^3$ is pyrazolyl substituted with one substituent selected from a group consisting of methyl and trifluoromethyl.

(5-9) The compound or a salt thereof, in which $R^3$ is pyrazolyl substituted with one substituent selected from a group consisting of methyl and trifluoromethyl.

(5-10) The compound or a salt thereof, in which $R^3$ is pyrazolyl substituted with one methyl.

(5-11) The compound or a salt thereof, in which $R^3$ is pyrazolyl, and the pyrazolyl may be substituted with 1 to 3 substituents selected from a group consisting of $C_{1-6}$ alkyl which may be substituted with 1 to 3 halogens; and —O—($C_{1-6}$ alkyl).

(6) The compound or a salt thereof, in which $R^4$ is H, $C_{1-6}$ alkyl which may be substituted, or halogen.

(6-1) The compound or a salt thereof, in which $R^4$ is H or halogen.

(6-2) The compound or a salt thereof, in which $R^4$ is H, F or Cl.

(6-3) The compound or a salt thereof, in which $R^4$ is H or F.

(7) The compound or a salt thereof, in which $R^5$ and $R^6$ are the same as or different from each other and are H or $C_{1-6}$ alkyl which may be substituted.

(7-1) The compound or a salt thereof, in which $R^5$ and $R^6$ are the same as or different from each other and are H or $C_{1-6}$ alkyl.

(7-2) The compound or a salt thereof, in which $R^5$ and $R^6$ are the same as or different from each other and are H or methyl.

(7-3) The compound or a salt thereof, in which $R^5$'s are the same as or different from each other and are H or methyl, and $R^6$'s are H.

(7-4) The compound or a salt thereof, in which $R^5$ and $R^6$ are both H.

(8) The compound or a salt thereof, which is a combination of any two or more of the embodiments in (1) to (7-4) as described above, which do not conflict with each other.

The present invention includes the compound or a salt thereof, which is a combination of any two or more of the embodiments in (1) to (7-4) as described above, which do not conflict with each other, as described in (8) above, and specific examples thereof include the following embodiments.

(9) An embodiment which is a combination of (1-2), (2-1), (3-2), (4-1), (5-2), (6-1), and (7-2) above.

The compound of the formula (I) or a salt thereof, in which $R^1$ is H or methyl, X is a bond or —NH—, $R^2$ is $C_{1-6}$ alkyl which may be substituted with 1 to 3 F, Y is a bond or —O—, wherein (i) when Y is —O—, $R^3$ is heteroaryl selected from a group consisting of pyridyl, pyrazinyl, pyrimidinyl, thiazolyl, pyrazolyl, and isoxazolyl, or (ii) when Y is a bond, $R^3$ is heteroaryl selected from a group consisting of thiazolyl, pyrazolyl, and isoxazolyl, the heteroaryl represented by above (i) and (ii) may be substituted with 1 to 3 substituents selected from a group consisting of $C_{1-6}$ alkyl which may be substituted with 1 to 3 halogens; —O—($C_{1-6}$ alkyl); $C_{3-8}$ cycloalkyl; and halogen, when Y is a bond, $R^3$ may further be —NH—CO—O—$R^{32}$, $R^4$ is H or halogen, and $R^5$ and $R^6$ are the same as or different from each other and are H or methyl.

(10) An embodiment which is a combination of (1-2), (2-1), (3-5), (4-1), (5-7), (6-1), and (7-3) above.

The compound or a salt thereof as described in (9), in which $R^2$ is methyl or ethyl, (i) when Y is —O—, $R^3$ is pyridyl or pyrazolyl, or (ii) when Y is a bond, $R^3$ is pyrazolyl, the pyridyl and the pyrazolyl may be substituted with 1 to 3 substituents selected from a group consisting of $C_{1-6}$ alkyl which may be substituted with 1 to 3 halogens; and —O—($C_{1-6}$ alkyl), $R^5$'s are the same as or different from each other and are H or methyl, and, $R^6$'s are H.

(11) An embodiment which is a combination of (1-2), (2-1), (3-5), (4-1), (5-8), (6-1), and (7-3) above.

The compound or a salt thereof as described in (10), in which (i) when Y is —O—, $R^3$ is pyridyl substituted with one substituent selected from a group consisting of methyl and methoxy, or pyrazolyl substituted with one methyl; or (ii) when Y is a bond, $R^3$ is pyrazolyl substituted with one substituent selected from a group consisting of methyl and trifluoromethyl.

(12) An embodiment which is a combination of (1-2), (2-2), (3-5), (4-3), (5-10), (6-3), and (7-4) above.

The compound or a salt thereof as described in (11), in which

X is a bond,

Y is —O—, $R^3$ is pyrazolyl substituted with one methyl, $R^4$ is H or F, and $R^5$ and $R^6$ are both H.

Other embodiments of the present invention are shown below.

In certain embodiments, the present invention includes compounds selected from the following group or salts thereof:

N-[2-(6-fluoro-5-{2-[(1-methyl-1H-pyrazol-3-yl)oxy]ethoxy}-1H-indol-3-yl)ethyl]acetamide, N-[2-(2-methyl-5-{2-[(1-methyl-1H-pyrazol-3-yl)oxy]ethoxy}-1H-indol-3-yl)ethyl]acetamide, and N-[2-(2-methyl-5-{2-[(1-methyl-1H-pyrazol-3-yl)oxy]ethoxy}-1H-indol-3-yl)ethyl]propanamide.

In another embodiment, the present invention includes compounds selected from the following group or salts thereof:

1-[2-(5-{2-[(6-methoxypyridin-3-yl)oxy]ethoxy}-1H-indol-3-yl)ethyl]-3-methylurea, N-[2-(5-{2-[(6-methylpyridin-2-yl)oxy]ethoxy}-1H-indol-3-yl)ethyl]acetamide, N-[2-(6-fluoro-2-methyl-5-{2-[(1-methyl-1H-pyrazol-3-yl)oxy]ethoxy}-1H-indol-3-yl)ethyl]acetamide, N-(2-{2-methyl-5-[2-(3-methyl-1H-pyrazol-1-yl)ethoxy]-1H-indol-3-yl}ethyl)propanamide, and 1-[2-(5-{2-[(6-methoxypyridin-3-yl)oxy]ethoxy}-2-methyl-1H-indol-3-yl)ethyl]-3-methylurea.

In a further embodiment, the present invention includes compounds selected from the following group or salts thereof:

N-[2-(5-{2-[(1-methyl-1H-pyrazol-3-yl)oxy]ethoxy}-1H-indol-3-yl)ethyl]propanamide, 1-methyl-3-[2-(2-methyl-5-{2-[(2-methylpyridin-4-yl)oxy]ethoxy}-1H-indol-3-yl)ethyl]urea, 1-methyl-3-[2-(2-methyl-5-{2-[(1-methyl-1H-pyrazol-3-yl)oxy]ethoxy}-1H-indol-3-yl)ethyl]urea, N-[(2R)-2-(6-fluoro-5-{2-[(1-methyl-1H-pyrazol-3-yl)oxy]ethoxy}-1H-indol-3-yl)propyl]acetamide, and N-[(2R)-2-(6-chloro-5-{2-[(1-methyl-1H-pyrazol-3-yl)oxy]ethoxy}-1H-indol-3-yl)propyl]acetamide.

In a still further embodiment, the present invention includes compounds selected from the following group or salts thereof:

N-[2-(5-{2-[(6-methoxypyridin-3-yl)oxy]ethoxy}-1H-indol-3-yl)ethyl]acetamide,

N-[2-(5-{2-[3-(trifluoromethyl)-1H-pyrazol-1-yl]ethoxy}-1H-indol-3-yl)ethyl]acetamide, and N-[2-(2-methyl-5-{2-[(2-methylpyridin-4-yl)oxy]ethoxy}-1H-indol-3-yl)ethyl]acetamide.

The compound of the formula (I) may exist in the form of tautomers or geometrical isomers depending on the kind of substituents. In the present specification, the compound of the formula (I) shall be described in only one form of isomer, yet the present invention includes other isomers, and also includes isolated forms of the isomers, or a mixture thereof.

In addition, the compound of the formula (I) may have asymmetric carbon atoms or axial chirality in some cases, and correspondingly, it may exist in the form of optical isomers. The present invention includes both an isolated form of the optical isomers of the compound of the formula (I) or a mixture thereof.

Furthermore, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and Pharmaceutical Research and Development, Drug Design, Hirokawa Publishing Company (1990), Vol. 7, 163-198.

Moreover, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyl tartaric acid, citric acid, methanesulfonic acid, ethanesulfonic acid, benzenesulfonic acid, p-toluenesulfonic acid, aspartic acid, and glutamic acid, and salts with inorganic bases such as sodium, potassium, magnesium, calcium, and aluminum or organic bases such as methylamine, ethylamine, ethanolamine, lysine, and ornithine, salts with various amino acids or amino acid derivatives such as acetylleucine, ammonium salts, and the like.

The salts of the compound of the formula (I) can also be prepared by carrying out a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemate (for example, fractional crystallization for inducing diastereomer salts with optically active bases or acids, chromatography using a chiral column or the like, and others), and further, the isomers can also be prepared from an appropriate optically active starting compound.

Moreover, the present invention also includes various hydrates or solvates, and crystal polymorphs and co-crystalline substances of the compound of the formula (I) or a salt thereof. In addition, the present invention also includes compounds labeled with various radioactive or non-radioactive isotopes.

(Preparation Methods)

The compound of the formula (I) or a salt thereof can be prepared using the characteristics based on the basic structure or the type of substituents and by applying various known synthesis methods. During the preparation, replacement of the functional group with a suitable protective group (a group that can be easily converted into the functional group) at the stage from starting material to an intermediate may be effective depending on the type of functional groups in the production technology in some cases. Such a protective group may include, for example, the protective groups described in "Greene's Protective Groups in Organic Synthesis (4$^{th}$ edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, the prodrug of the compound of the formula (I) can be prepared by introducing a specific group at the stage from a starting material to an intermediate, or by further carrying out the reaction using the obtained compound of the formula (I), as in the case of the above-mentioned protective group. The reaction can be carried out by using methods known to those skilled in the art, such as ordinary esterification, amidation, and dehydration.

Hereinbelow, the representative preparation methods for the compound of the formula (I) will be described. Each of the production processes may also be carried out with reference to the References appended in the present description. Further, the preparation methods of the present invention are not limited to the examples as shown below.

(Production Process 1)

[Chem. 9]

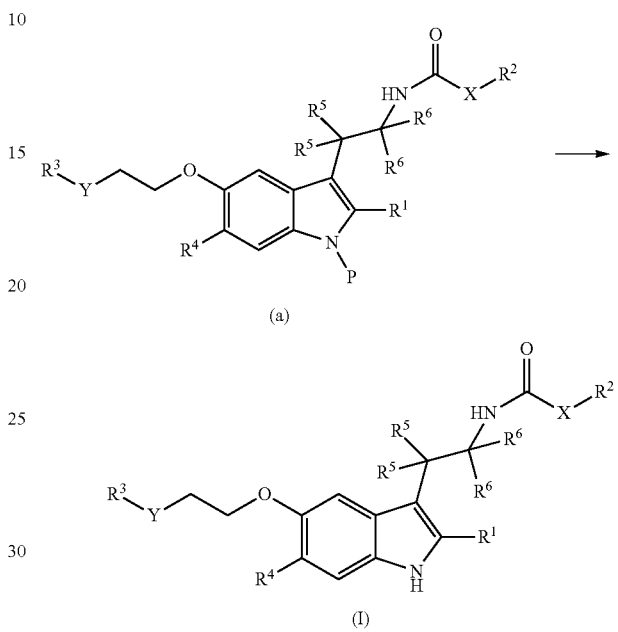

(In the formula, P represents a protective group. The same shall apply hereinafter.)

The present production process is a method in which a compound (a) is subjected to deprotection of nitrogen atoms in the indole to prepare the compound of the formula (I), which is the compound of the present invention. Here, examples of the protective group P include a p-toluene sulfonyl group and the like.

The present reaction can be carried out with reference to "Protective Groups in Organic Synthesis" written by Greene and Wuts, 4$^{th}$ edition, John Wiley & Sons Inc., 2006. Examples thereof include a reaction using magnesium which has been activated by sonication in methanol.

(Production Process 2)

[Chem. 10]

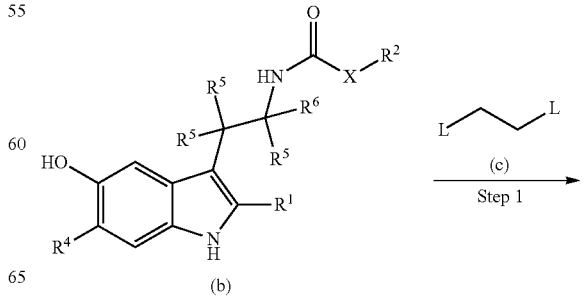

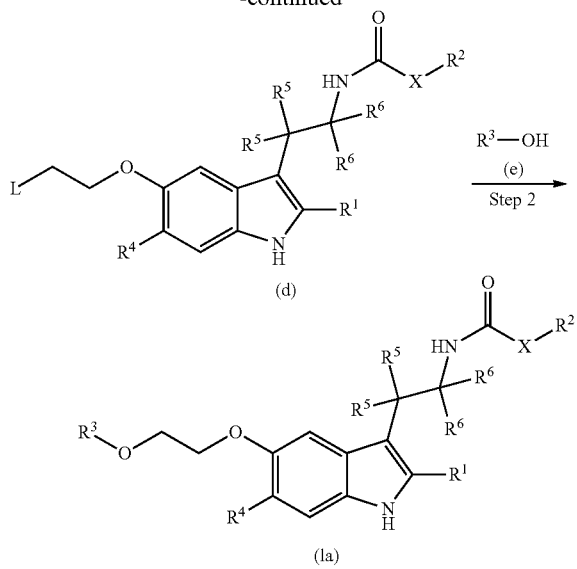

(In the formula, L represents a leaving group. The same shall apply hereinafter.)

The present production process is a method for preparing a compound of the formula (Ia), that is the compound of the formula (I) which is the compound of the present invention, in which Y is —O—. Here, examples of the leaving group L include a p-toluene sulfonyloxy group, a bromo group, and the like, and L's may be the same as or different from each other.

(Step 1)

This step is a step of preparing a compound of the formula (d) from a compound of the formula (b) and a compound of the formula (c).

In this reaction, the compound of the formula (b) and the compound of the formula (c), in equivalent amounts or in an excess amount of the compound of the formula (c), are used, and the mixture is stirred in a solvent which is inert to the reaction, under from cooling to heating and refluxing, and preferably from 0° C. to 80° C., usually for 0.1 hours to 5 days, in the presence of a base. Examples of the solvent used herein are not particularly limited, but include aromatic hydrocarbons such as benzene, toluene, xylene, and the like, ethers such as diethyl ether, tetrahydrofuran, dioxane, dimethoxyethane, and the like halogenated hydrocarbons such as dichloromethane, 1,2-dichloroethane, chloroform, and the like, N,N-dimethyl formamide, dimethyl sulfoxide, ethyl acetate, acetonitrile, and a mixture thereof. Examples of the base include organic bases such as triethylamine, diisopropylethylamine, 1,8-diazabicyclo[5.4.0]-7-undecene, n-butyllithium, and the like, and inorganic bases such as sodium carbonate, potassium carbonate, cesium carbonate, sodium hydride, potassium tert-butoxide, and the like. It may be advantageous to carry out a reaction in the presence of a phase transfer catalyst such as tetra-n-butylammonium chloride in some cases.

REFERENCES

"Organic Functional Group Preparations" written by S. R. Sandler and W. Karo, 2$^{nd}$ edition, Vol. 1, Academic Press Inc., 1991, "Courses in Experimental Chemistry (5$^{th}$ edition)" edited by The Chemical Society of Japan, Vol. 14 (2005) (Maruzen).

(Step 2)

This step is a step of preparing a compound of the formula (Ia) from a compound of the formula (d) and a compound of the formula (e). The reaction condition of the present step is the same as the step 1 as described above.

(Preparation of Starting Compounds)

The starting compounds in the preparation methods above can be prepared by using any of, for example, the methods below, the methods described in Preparation Examples as described later, known methods, or modified methods thereof.

(Starting Material Synthesis 1)

[Chem. 11]

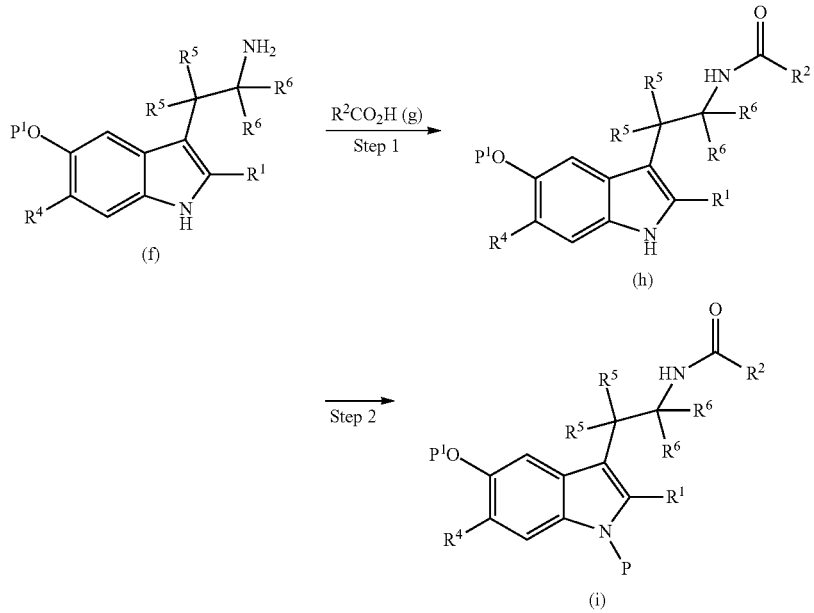

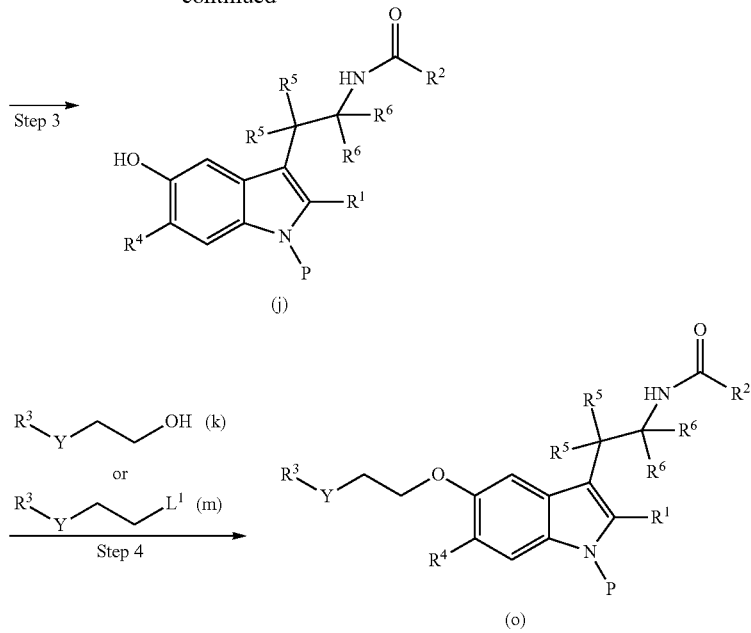

(In the formula, P and P$^1$ represent protective groups, and L$^1$ represents a leaving group.)

The present production process is a method for preparing a compound of the formula (o), which is the compound of the formula (a) in which X is a bond. Here, examples of the protective group P include a p-toluene sulfonyl group and the like, and examples of the protective group P$^1$ include a benzyl group, a methyl group, and the like. Further, examples of the leaving group L$^1$ include a bromo group, a chloro groups, and the like.

(Step 1)

This step is a step of preparing a compound of the formula (h) by subjecting a compound of the formula (f) and a compound of the formula (g) to an amidation reaction.

In this reaction, the compound of the formula (f) and the compound of the formula (g) in equivalent amounts, or either thereof in an excess amount are used, and the mixture is stirred in a solvent which is inert to the reaction, under from cooling to heating, and preferably from −20° C. to 60° C., usually for 0.1 hours to 5 days, in the presence of a condensing agent. Examples of the solvent used herein are not particularly limited, but include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, dimethoxyethane, and the like, N,N-dimethylformamide, dimethylsulfoxide, ethyl acetate, acetonitrile, water, and a mixture thereof. Examples of the condensing agent include, but are not limited to, 1-(3-dimethylaminopropyl)-3-ethylcarbodiimide, dicyclohexylcarbodiimide, 1,1'-carbonyldiimidazole, diphenylphosphoryl azide, and phosphorus oxychloride. It is preferable in some cases for the progress of the reaction to use an additive (for example, 1-hydroxybenzotriazole). In addition, it is preferable in some cases for the smooth progress of the reaction to use organic bases such as triethylamine, N,N-diisopropylethylamine, N-methylmorpholine, and the like, or inorganic bases such as potassium carbonate, sodium carbonate, potassium hydroxide, and the like.

Furthermore, it is also possible to use a method in which a compound of the formula (g) is converted to a reactive derivative thereof, which is then reacted with a compound of the formula (f). Examples of the reactive derivative of the carboxylic acid include acid halides that can be obtained by the reaction with a halogenating agent such as phosphorus oxychloride, thionyl chloride, and the like, mixed acid anhydrides that can be obtained by the reaction with isobutylchloroformate or the like, and active esters that can be obtained by condensation with 1-hydroxybenzotriazole or the like. The reaction of the reactive derivatives with the compound (f) can be carried out under from cooling to heating, and preferably from −20° C. to 60° C., in a solvent which is inert to the reaction, such as halogenated hydrocarbons, aromatic hydrocarbons, ethers, and the like.

In addition, it is also possible to use a method in which a compound of the formula (f) is reacted with carboxylic anhydride instead of a compound of the formula (g) in the presence of a base such as triethylamine and the like. Examples of the carboxylic acid anhydride include acetic anhydride, propionic anhydride, and the like. The reaction of the carboxylic acid anhydride with the compound of the formula (f) can be carried out under from cooling to heating, and preferably from −20° C. to 60° C., in a solvent which is inert to the reaction, such as halogenated hydrocarbons, aromatic hydrocarbons, ethers, and the like.

REFERENCES

"Organic Functional Group Preparations" written by S. R. Sandler and W. Karo, 2$^{nd}$ edition, Vol. 1, Academic Press Inc., 1991, "Courses in Experimental Chemistry (5$^{th}$ edition)" edited by The Chemical Society of Japan, Vol. 16 (2005) (Maruzen).

(Step 2)

This step is a reaction of protecting the position 1 of the indole of the compound of the formula (h). The present reaction can be carried out with reference to "Protective Groups in Organic Synthesis" written by Greene and Wuts, 4th edition, John Wiley & Sons Inc., 2006.

(Step 3)

This step is a step of preparing a compound of the formula (j) by deprotection reaction of the compound of the formula (i).

This step can be carried out with reference to "Protective Groups in Organic Synthesis" written by Greene and Wuts, 4th edition, John Wiley & Sons Inc., 2006.

(Step 4)

This step is a step of preparing a compound of the formula (o) by reacting a compound of the formula (j) with a compound of the formula (k) or a compound of the formula (m).

In the present step, in the case of using the compound of the formula (k), a method of using known diazocarboxylic acid esters or diazocarboxylic acid amides together with known phosphines, or a so-called known Mitsunobu reaction or a modified method thereof using (tributylphospholanylidene)acetonitrile (Tsunoda Reagent) or the like, which are well-known methods to a person skilled in the art.

In the present reaction, the compound (j) and the compound (k) in equivalent amounts, or either thereof in an excess amount are used, and the mixture is stirred in a solvent which is inert to the reaction, under from cooling to heating and refluxing, and preferably from 0° C. to 150° C., usually for 0.1 hours to 5 days. Examples of the solvent used herein are not particularly limited, but include aromatic hydrocarbons, ethers, halogenated hydrocarbons, N,N'-dimethyl formamide (DMF), dimethyl sulfoxide (DMSO), ethyl acetate, acetonitrile, and a mixture thereof.

As the references for the present reaction, for example, the following references can be referred to.

Synthesis (1981), 1

Tetrahedron Letters (1995) 36, 2529; ibid, (1996) 37, 2463

Further, the reaction condition in the case of using the compound of the formula (m) in the present step is the same as in the step 1 of the production process 2 as described above.

(Starting Material Synthesis 2)

[Chem. 12]

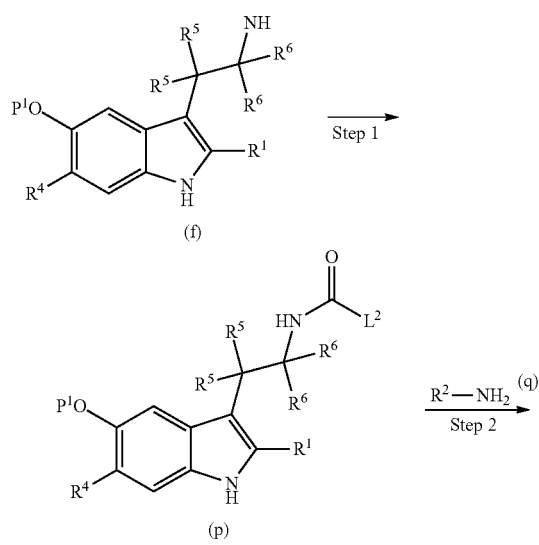

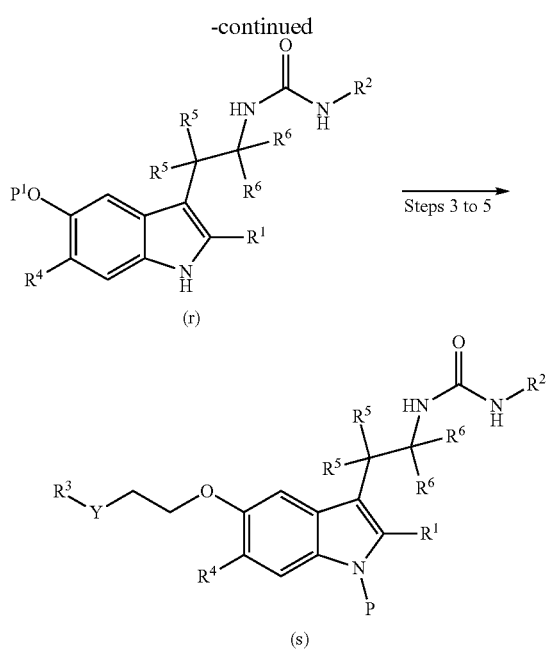

(In the formula, $L^2$ represents a leaving group.)

The present production process is a method for preparing a compound of the formula (s), which is the compound of the formula (a) in which X is NH, via a compound of the formula (p) from the compound of the formula (f). Here, examples of the leaving group $L^2$ include imidazolyl, a 4-nitrophenoxy group, and the like.

(Step 1)

This step is carried out by reacting the compound (f) with a carbonylating reagent in an equivalent amount or in an excess amount, under cooling to heating, and preferably from −20° C. to 80° C., usually for about 0.1 hours to 1 day, in a solvent which is inert to the reaction. Examples of the carbonylating reagent include 1,1'-carbonyldiimidazole, 4-nitrophenyl chloroformate, diphosgene, triphosgene, phenyl chloroformate, and the like. Examples of the solvent as used herein are not particularly limited, but include halogenated hydrocarbons such as dichloromethane, 1,2-dichloroethane, chloroform, and the like, aromatic hydrocarbons such as benzene, toluene, xylene, and the like, ethers such as diethyl ether, tetrahydrofuran, dioxane, dimethoxyethane, and the like, N,N-dimethyl formamide, dimethyl sulfoxide, ethyl acetate, acetonitrile, and a mixture thereof. Further, it may be advantageous in some cases for the smooth progress of the reaction to carry out the reaction in the presence of a base such as triethylamine or the like.

(Step 2)

This step is a step in which without isolating the compound of the formula (p), to the reaction mixture is added a compound of the formula (q) in an equivalent amount or in an excess amount, and the mixture is reacted under cooling to heating, and preferably from −20° C. to 80° C., usually for about 0.1 hours to 1 day. In the case where the compound of the formula (p) is stable, this may be isolated once and then reacted with the compound of the formula (q).

REFERENCES

"Organic Functional Group Preparations" written by S. R. Sandier and W. Karo, 2nd edition, Vol. 2, Academic Press Inc., 1991

(Steps 3 to 5)

This step can be carried out by the same method as the steps 2 to 4 of Starting Material Synthesis 1 as described above.

TEST EXAMPLE

The pharmacological activity of the compound of the formula (I) was confirmed by the tests shown below.

Test Example 1

Test for Evaluating Activation of Human $MT_1$ and Human $MT_2$ Receptor by Test Compound Using Human $MT_1$ and Human $MT_2$ Receptor-Expressing Cells Experimental Method (1) Construction of Expression Vectors of Human $MT_1$ and Human $MT_2$ Receptors and $G_{q/i}$ Chimeric G Protein A human $MT_1$ receptor gene (GenBank Accession No.: NM_005958.3) and a human $MT_2$ receptor gene (GenBank Accession No.: NM_005959.3) were each introduced into an expression vector pcDNA3.1/Zeo (Invitrogen, Inc.). Further, a gene sequence expressing a $G_{q/i}$ chimeric G protein, in which 5 amino acids at the C terminal of a protein encoded by a human $G_q$ gene (GenBank Accession No.: NM_002072.4) are substituted with 5 amino acids at the C terminal of a protein encoded by a $G_i$ gene (GenBank Accession No.: NM_002069.5), was introduced into pcDNA3.1/Hyg (Invitrogen, Inc.).

(2) Construction of Cells Stably Expressing Human $MT_1$ and Human $MT_2$ Receptors An expression vector of a human $MT_1$ receptor and an expression vector of a human $G_{q/i}$ chimeric G protein were introduced into HEK293EBNA1 cells, and an expression vector of a human $MT_2$ receptor and an expression vector of a human $G_{q/i}$ chimeric G protein were introduced into HEK293 cells. The introduction was carried out according to the attached instructions, using a Lipofectoamine (registered trademark) 2000 Reagent (Invitrogen, Inc.). Cells thus introduced were incubated in a 10% FBS-containing DMEM (Invitrogen, Inc.) medium including 0.02 mg/mL of zeocin and 0.05 mg/mL of hygromycin as selection drugs for 15 days under an environment of 37° C. and 5% $CO_2$, thereby acquiring drug-resistant clones.

(3) Measurement of Intracellular $Ca^{2+}$ Concentration by FLIPR (Registered Trademark)

The respective stably expressing cells were dispensed into 96-well poly-D-lysine-coated plates (Falcon Co.) to 40,000 cells/well the day before the experiment, and incubated overnight in a DMEM (Invitrogen, Inc.) medium including 10% FBS at 37° C. and 5% $CO_2$. The medium was replaced with a loading buffer (washing solution (Hank's balanced salt solution (HBSS) including 20 mM HEPES-NaOH and 2.5 mM probenecid as a final concentration) including 2 μM Fluo-4AM (Dojindo Co.) and 0.04% Pluronic F-127 (Life Technologies), and incubated for 1 hour at 37° C. and 5% $CO_2$. Thereafter, the cells were washed with a plate washer (ELx405, BIO-TEK Instrument, Inc.) set with the washing solution, and set in an intracellular $Ca^{2+}$ concentration measuring systems (FLIPR (registered trademark), Molecular Device Co.). The test compound was dissolved in dimethylsulfoxide (DMSO), diluted to a final concentration of −12 to −5 log M, set in a FLIPR (registered trademark) device together with the cells, and added to the cells in the device. At this time, a change in the intracellular $Ca^{2+}$ concentrations was measured.

For the agonistic activity, when a maximum reaction by ramelteon was taken as 100%, the activation action (Emax (%)) of the test compound with respect to the maximum reaction of ramelteon was determined and an efficacy ($EC_{50}$ (nM)) was calculated by a logistic regression method.

The $EC_{50}$ values and the Emax values of melatonin (purchased from Sigma), ramelteon (purified from 8-mg tablets of Rozerem purchased from Takeda Pharmaceutical Co., Ltd.), and the Example compounds of the present invention are shown in Table 1. Ex represents Example No. of the test compound.

TABLE 1

| | Human $MT_1$ | | Human $MT_2$ | |
|---|---|---|---|---|
| Ex. | $EC_{50}$ (nM) | Emax (%) | $EC_{50}$ (nM) | Emax (%) |
| Melatonin | 1.1 | 94 | 4.3 | 91 |
| Ramelteon | 0.28 | 100 | 1.1 | 100 |
| 1 | 3.9 | 95 | 14 | 119 |
| 2 | 7.0 | 125 | 17 | 125 |
| 3 | 9.9 | 94 | 51 | 127 |
| 4 | 18 | 102 | 33 | 102 |
| 5 | 13 | 89 | 150 | 48 |
| 6 | 7.5 | 103 | 10 | 119 |
| 7 | 18 | 90 | 22 | 125 |
| 8 | 9.1 | 93 | 12 | 107 |
| 9 | 9.9 | 84 | 32 | 116 |
| 10 | 8.3 | 95 | 21 | 117 |
| 11 | 0.71 | 107 | 2.4 | 99 |
| 12 | 7.7 | 96 | 18 | 93 |
| 13 | 4.3 | 105 | 7.0 | 110 |
| 14 | 5.5 | 100 | 13 | 102 |
| 15 | 8.4 | 106 | 12 | 110 |
| 16 | 10 | 100 | 100 | 82 |
| 17 | 5.9 | 84 | 33 | 91 |
| 18 | 7.7 | 89 | 21 | 123 |
| 19 | 5.7 | 94 | 17 | 91 |
| 20 | 4.1 | 115 | 7.7 | 119 |
| 21 | 7.0 | 103 | 44 | 59 |
| 22 | 7.3 | 105 | 8.7 | 95 |
| 23 | 21 | 87 | 54 | 68 |
| 24 | 13 | 99 | 18 | 71 |
| 25 | 1.5 | 105 | 2.9 | 96 |
| 26 | 8.8 | 97 | 9.8 | 106 |
| 27 | 8.7 | 83 | 10 | 82 |
| 28 | 6.8 | 119 | 35 | 62 |
| 29 | 10 | 100 | 24 | 112 |
| 30 | 4.8 | 106 | 15 | 110 |
| 31 | 1.4 | 104 | 28 | 88 |

TABLE 2

| | Human $MT_1$ | | Human $MT_2$ | |
|---|---|---|---|---|
| Ex. | $EC_{50}$ (nM) | Emax (%) | $EC_{50}$ (nM) | Emax (%) |
| 32 | 3.4 | 96 | 50 | 66 |
| 33 | 4.3 | 103 | 60 | 53 |
| 34 | 4.3 | 93 | 10 | 125 |
| 35 | 3.7 | 94 | 8.3 | 114 |
| 36 | 6.0 | 101 | 15 | 96 |
| 37 | 2.1 | 105 | 7.1 | 104 |
| 38 | 2.0 | 97 | 13 | 105 |
| 39 | 7.2 | 104 | 51 | 49 |
| 40 | 6.3 | 81 | 160 | 42 |
| 41 | 11 | 75 | 26 | 93 |
| 42 | 7.9 | 97 | 12 | 103 |
| 43 | 5.3 | 110 | 7.1 | 104 |
| 44 | 3.3 | 103 | 4.5 | 102 |
| 45 | 2.3 | 99 | 14 | 127 |
| 46 | 3.4 | 78 | 6.3 | 76 |
| 47 | 9.8 | 124 | 41 | 145 |

TABLE 2-continued

| | Human MT$_1$ | | Human MT$_2$ | |
|---|---|---|---|---|
| Ex. | EC$_{50}$ (nM) | Emax (%) | EC$_{50}$ (nM) | Emax (%) |
| 48 | 8.4 | 92 | 56 | 106 |
| 49 | 5.6 | 102 | 11 | 119 |
| 50 | 8.5 | 89 | 6.4 | 111 |
| 51 | 5.3 | 95 | 4.7 | 108 |
| 52 | 10 | 92 | 5.6 | 117 |
| 53 | 1.0 | 112 | 4.8 | 99 |
| 54 | 0.77 | 111 | 2.6 | 109 |
| 55 | 8.0 | 109 | 9.1 | 133 |
| 56 | 15 | 92 | 9.9 | 125 |
| 57 | 12 | 94 | 13 | 114 |
| 58 | 1.2 | 99 | 3.4 | 99 |
| 59 | 6.6 | 120 | 9.6 | 99 |
| 60 | 7.2 | 94 | 9.2 | 104 |
| 61 | 6.9 | 84 | 5.4 | 92 |
| 62 | 11 | 101 | 16 | 118 |
| 63 | 9.7 | 90 | 9.0 | 105 |
| 64 | 1.6 | 102 | 2.1 | 116 |

From the results above, it was confirmed that the Example compound of the present invention has human MT$_1$ and/or human MT$_2$ receptor agonistic activities.

Test Example 2

Test to Evaluate Effect of Test Compound on Urethral Pressure

It has been reported that an increase in the urethral pressure is useful for the treatment of urinary incontinence, in particular, stress urinary incontinence (for example, Drugs, 64, 14, 1503-1516 (2004)). In order to confirm whether the compound of the present invention increases the urethral pressure and thus is useful for the treatment of urinary incontinence, in particular, stress urinary incontinence, the following tests were carried out.

Experimental Method

SD female rats were anesthetized with urethane and subjected to laparotomy. Then, the bladder apex was incised and a catheter was inserted from the bladder apex. Further, the catheter tip was ligated and fixed to be located in the proximal urethra portion. The catheter was connected to a pressure transducer and an infusion pump. Further, a catheter for administrating the compound was fitted into the femoral vein. Physiological saline was continuously infused into the urethra and the perfusion pressure in the urethra was measured. After the urethral pressure was stabilized, the test compound that had been dissolved in physiological saline, or physiological saline including 5% dimethylacetamide and 0.5% Cremophor was administered intravenously at 0.01 mg/kg or 0.1 mg/kg, and a change in urethral pressures was measured.

Further, the results of administering an active metabolite of midodrine (ST-1059: purchased from CHEMIZON) (J. Urology, 118, 980-982 (1977)) which is an $\alpha_1$ adrenoceptor agonist and is confirmed to have a clinical effect on stress urinary incontinence at doses, 0.01 mg/kg and, 0.1 mg/kg in rats, presumed to correspond to the clinical doses are referenced and shown in the Tables below.

The increment value in the urethral pressures of ramelteon and the Example compounds of the present invention at the time of administration are shown in Table 3. Ex represents Example No. of the test compound and N.T represents Not Tested.

TABLE 3

| | Increment value in the urethral pressures (mmHg) | |
|---|---|---|
| Ex. | 0.1 mg/kg | 0.01 mg/kg |
| ST-1059 | 9.6 ± 1.8 | 4.9 ± 1.1 |
| Ramelteon | 11.1 ± 1.7 | 6.4 ± 1.0 |
| 1 | 9.3 ± 1.5 | 6.7 ± 0.6 |
| 4 | 7.5 ± 1.6 | N.T. |
| 5 | 8.2 ± 1.0 | 4.8 ± 0.6 |
| 6 | 9.6 ± 1.3 | 6.7 ± 1.1 |
| 7 | 6.9 ± 0.9 | 6.3 ± 0.8 |
| 8 | 7.6 ± 1.3 | 4.7 ± 0.4 |
| 9 | 8.0 ± 1.2 | N.T. |
| 10 | 8.0 ± 1.2 | 4.4 ± 1.2 |
| 11 | 8.1 ± 0.6 | 4.1 ± 0.8 |
| 13 | 10.0 ± 2.3 | 7.7 ± 1.5 |
| 15 | 11.2 ± 0.5 | 6.4 ± 0.5 |
| 18 | 8.3 ± 0.7 | N.T. |
| 23 | 8.9 ± 0.9 | 5.6 ± 1.0 |
| 31 | 7.7 ± 1.2 | 5.2 ± 0.9 |
| 37 | 9.0 ± 0.6 | N.T. |
| 38 | 9.4 ± 2.6 | N.T. |

Ramelteon and the Example compounds of the present invention administration groups exhibited an increment value in the urethral pressures which is equal to or more than that of ST-1059. From this, it was suggested that ramelteon and the Example compounds of the present invention have an action of increasing the urethral pressure.

Test Example 3

Test for Evaluation of Central Nervous System Penetration

It has been reported that the "central nervous system penetration" can be expressed by an index indicating a ratio of the concentration of the test compound in the cerebrospinal fluid (hereinafter described as CSF) (hereinafter described as $C_{CSF}$) to the unbound concentration of the test compound in the plasma (hereinafter described as $C_{plasma,u}$) which is the ratio of unbound concentration in the CSF-plasma (which means a value represented by $C_{CSF}/C_{plasma,u}$, and hereinafter described as $K_{p,uu,CSF}$), or a ratio of the total concentration of the test compound in the brain (hereinafter described as $C_{brain}$) to the total concentration of the test compound in the plasma (hereinafter described as $C_{plasma,t}$) which is the ratio of the concentration in the brain-plasma (which means a value represented by $C_{brain}/C_{plasma,t}$, and hereinafter described as $K_{p,brain}$) (Xenobiotica, 42, 11-27 (2012) and J. Pharmacol. Exp. Ther., 325, 349-356 (2008)). For example, it has been described that using, for example, a sample collected after 15 minutes from the intravenous administration of the test compound, the $K_{p,uu,CSF}$ from the drug concentrations in CSF and the plasma is calculated, from which the central nervous system penetration is evaluated. Further, it has been described that with plural drugs known to have a low central nervous system penetration, that is, Verapamil, Quinidine, and Imatinib, the $K_{p,uu,CSF}$ value was a value of 0.11 or less (Xenobiotica, 42, 11-27 (2012)).

In addition, it has been reported that the central nervous system penetration can be expressed by an index indicating a ratio of an area under the curve (AUC) of the unbound concentration-time in the CSF-plasma ($K_{p,uu,CSF,AUC}$), which is a ratio of the area under the curve of time of the test compound in CSF to the AUC of the unbound concentration of the test compound in the plasma, and a ratio of an area under the curve of the concentration-time in the brain-plasma ($K_{p,brain,AUC}$), which is a ratio of the AUC of the total concentration in the brain to the AUC of the total concentration in the plasma (Bioorg. Med. Chem. Lett., 22, 2932-2937, (2012)).

(1) Measurement of Unbound Fraction (fp) in Plasma of Rat by Ultracentrifugation Method A test compound (100 μg/mL, 50% acetonitrile solution) at 1% (v/v) with respect to the amount of the plasma was added to rat plasma, and dispensed to a sample for a supernatant and a sample for the plasma. The sample for a supernatant was ultracentrifuged at 436,000×g and 37° C. for 140 minutes, and the sample for the plasma was incubated at 37° C. for 140 minutes.

After 140 minutes, the sample for a supernatant after the ultracentrifugation and the sample for the plasma were taken, and mixed with the blank plasma or the blank supernatant, respectively. Acetonitrile including an internal standard material was added to each of the samples with the removal of protein, and after the centrifugation at 2150×g and 4° C. for 10 minutes the supernatant was injected into LC-MS/MS.

The unbound fraction in the plasma was calculated by the following equation.

$$fp = \frac{1/D}{1/(fu, app) - 1 + 1/D}$$ [Chem. 13]

(In the formula, fp: an unbound fraction in the plasma and D: a dilution rate of the plasma.

fu,app=the peak area ratio of a supernatant sample/the peak area ratio of a plasma sample, and peak area ratio=the peak area of a test compound/the peak area of an internal standard material).

(2) Measurement of Unbound Fraction (fp) in Plasma of Rat by Equilibrium Dialysis Method The unbound fraction in the plasma by an equilibrium dialysis method was measured as follows, using Rapid Equilibrium Dialysis Device (RED device: ThermoScientific Co., Ltd.).

To the plasma of a rat was added a test compound (0.2 mM, 50% acetonitrile solution) in an amount corresponding to 1% (v/v) of the plasma amount, and 200 μL of obtained plasma sample was filled into a plasma chamber of a RED device insert. A buffer chamber was filled with 350 μL of PBS, followed by performing equilibrium dialysis by stirring in a $CO_2$ incubator at 37° C. for 16 hours. The sample after the completion of the equilibrium dialysis was recovered and the volume of the plasma sample was measured. To the plasma sample after the completion of the equilibrium dialysis were added PBS, a 20 mM ammonium formate buffer, and acetonitrile including an internal standard material. Similarly, to the PBS sample after the completion of the equilibrium dialysis was added a blank plasma, a 20 mM ammonium formate buffer, and acetonitrile including an internal standard material. This sample was left to stand at 4° C. for 30 minutes and then centrifuged 1500×g for 10 minutes, and the supernatant was measured by LC-MS/MS. The unbound fraction in the plasma was calculated by the following equation.

$$fp = Cf/\{(Cp-Cf)(V/V0)+Cf\}$$

fp: an unbound fraction in the plasma
Cf: a drug concentration on the side of buffer after dialysis
Cp: a drug concentration on the side of plasma after dialysis
V: a plasma volume after dialysis
V0: a plasma volume before dialysis (3) CSF-to-Plasma Unbound Concentration Ratio in Rat At 15 minutes after intravenously administration of the test compound to the rats, the plasma and CSF were collected. A 50% acetonitrile solution and an acetonitrile including internal standard material were added to the collected plasma or CSF. After centrifuging this sample at 4° C. and 2150×g for 10 minutes, the supernatant was measured by LC-MS/MS, and the total concentration of the test compound in the plasma ($C_{plasma,t}$) and the concentration of the test compound in CSF ($C_{CSF}$) were obtained. The unbound concentration in the plasma ($C_{plasma,u}$) of the test compound and the CSF-to-plasma unbound concentration ratio ($K_{p,uu,CSF}$) of the test compound was calculated by the following equation.

$$C_{plasma,u} = fp \times C_{plasma,t}$$ [Chem. 14]

$$K_{p,uu,CSF} = \frac{C_{CSF}}{C_{plasma,u}}$$

(4) Brain-to-Plasma Concentration Ratio in Rat

At 15 minutes after intravenously administration of the test compound to the rats, the plasma and brain were collected. A 50% acetonitrile solution and an acetonitrile including internal standard material were added to the collected plasma. The collected brain was added to a 2-fold volume of PBS and homogenized. A 50% acetonitrile solution and an acetonitrile including internal standard material were added to the brain homogenate. The sample was centrifuged at 4° C. and 2150×g for 10 minutes, the supernatant was measured by LC-MS/MS, and the total concentration of the test compound in the brain ($C_{brain}$) and the total concentration of the test compound in the plasma ($C_{plasma,t}$) were obtained. The brain-to-plasma concentrations ratio ($K_{p,brain}$) was calculated by the following equation.

$$K_{p,brain} = \frac{C_{brain}}{C_{plasma,t}}$$ [Chem. 15]

The $K_{p,uu,CSF}$ values and the $K_{p,brain}$ values of ramelteon and some Example compounds of the present invention are shown in Table 4. Ex represents Example No. of the test compound. Unless otherwise specified, the $K_{p,uu,CSF}$ was calculated using the fp values determined by an ultracentrifugation method. Further, N.T. represents Not Tested.

TABLE 4

| Ex. | $K_{p, uu, CSF}$ | $K_{p, brain}$ |
| --- | --- | --- |
| Ramelteon | 1.74 | N.T. |
| 1 | 0.05 | N.T. |
| 4 | 0.11 | 0.29 |
| 5 | 0.10 | 0.089 |
| 6 | 0.06 | 0.09 |
| 7 | 0.14 | 0.03 |
| 8 | 0.08 | 0.04 |
| 9 | N.D. | 0.01 |
| 10 | 0.07 | 0.02 |
| 11 | 0.05 | N.T. |
| 13 | 0.03 | N.T. |
| 15 | 0.04 | N.T. |

TABLE 4-continued

| Ex. | $K_{p, uu, CSF}$ | $K_{p, brain}$ |
|---|---|---|
| 18 | 0.11 | 0.03 |
| 23 | 0.04 | 0.03 |
| 31 | 0.01 | N.T. |
| 37 | 0.08 | 0.01 |
| 38 | 0.08 | 0.02 |

(Ramelteon represents the values of $K_{p,uu,CSF}$ after 10 minutes after the intravenous administration. Further, the $K_{p,uu,CSF}$ of Examples 37 and 38 was calculated using the fp values determined by an equilibrium dialysis method. In addition, N.D. denotes the concentration of the test compound in CSF that is no higher than the detection limit.)

(5) Ratio of Area Under Curve of Unbound Concentration-Time in CSF-Plasma in Rat and Ratio of Area Under Curve of Concentration-Time in Brain-Plasma in Rat A test compound was orally administered to a rat, and the plasma and CSF after 15 minutes, 30 minutes, 1 hour, 2 hours, and 4 hours were collected and measured by the same method as for the intravenous administration. The ratio of area under curve of unbound concentration-time in CSF-plasma in a rat $K_{p,uu,CSF,AUC}$ and the ratio of area under curve of concentration-time in the brain-plasma in a rat, $K_{p,brain,AUC}$, were calculated by the following equations. $AUC_{0-t}$ was calculated by a trapezoidal method.

$$K_{p,uu,CSF,AUC} = AUC_{0-t,CSF} / AUC_{0-t,plasma,u}$$

$$K_{p,brain,AUC} = AUC_{0-t,brain} / AUC_{0-t,plasma,t}$$

$$AUC_{0-t,plasma,u} = fp \times AUC_{0-t,plasma,t}$$

$AUC_{0-t,CSF}$; Drug $AUC_{0-t}$ in CSF
$AUC_{0-t,plasma,u}$; Unbound drug $AUC_{0-t}$ in plasma
$AUC_{0-t,plasma,t}$; Drug $AUC_{0-t}$ in plasma
$AUC_{0-t,brain}$; Drug $AUC_{0-t}$ in brain
($K_{p,uu,CSF,AUC}$ was calculated using the fp values according to an equilibrium dialysis method.)

The $K_{p,uu,CSF,AUC}$ values and $K_{p,brain,AUC}$ values of ramelteon, and some Example compounds of the present invention are shown in Table 5. Ex represents Example No. of the test compound.

TABLE 5

| Ex. | $K_{p, uu, CSF, AUC}$ | $K_{p, brain, AUC}$ |
|---|---|---|
| Ramelteon | 1.25 | N.T. |
| 1 | 0.05 | 0.01 |
| 6 | 0.07 | 0.02 |
| 7 | 0.12 | 0.017 |

From the results above, it was found that ramelteon had a $K_{p,uu,CSF}$ value of more than 1, a higher concentration in CSF than that in the plasma, and a high central nervous system penetration, whereas the Example compounds of the present invention had a lower central nervous system penetration than ramelteon with the $K_{p,uu,CSF}$ values of 0.2 or less, as shown from the results above, and some Example compounds had a significantly lower central nervous system penetration with the value of less than 0.1. In addition, it was found that the Example compounds of the present invention had highly lower $K_{p,brain}$, $K_{p,uu,CSF,AUC}$, and $K_{p,brain,AUC}$ values than ramelteon, and some Example compounds had a significantly lower central nervous system penetration with the value of less than 0.1.

Test Example 4

Measurement Test of Electroencephalogram in Rat (1) Handling

In order to accustom the animals to operations during the experiment, handling was carried out for about 1 minute for one example once a day from the next day of the animal acquisition to the day before the administration.

(2) Method for Preparing Electroencephalogram Electrode-Implanted Specimen

After the completion of a quarantine period, the animals showing no abnormal health condition were subjected to an electroencephalogram electrode chronic implantation surgery with reference to brain atlas of Pellegrino (Plenum Press, New York (1979)), or the like. Under anesthesia with pentobarbital sodium, the rat was calibrated in a brain stereotaxic apparatus. In the frontal cortex, a monopolar silver ball electrode having a diameter of the tip of about 1 mm was placed on a hard film of the brain. Into the hippocampus, a laminated bipolar electrodes made of stainless steel was stuck. The reference electrode was screwed around the olfactory brain. Further, as for the electromyogram measurement, the lead wire was implanted in the both electrodes about 1 cm between the electrodes in the neck portion. The other end was exposed to the head portion subcutaneously. The electrodes and the lead wires were subjected to soldering with connector sockets and fixed to the skull with a dental resin or the like.

(3) Sorting and Grouping of Animals

It was confirmed that rats which had been subjected to an electroencephalogram electrode chronic implantation surgery were recovered from the invasion of the surgery, and stable electroencephalogram were obtained therefrom. The weights of the animals were measured after 6 days or longer from the surgery using an electronic scale balance the day before the first administration, and rats were distributed in the descending order of body weights to perform administration. The administration order for the test materials was determined by a stratified random allocation method using a random number function of a spreadsheet software Excel (Microsoft Corporation).

(4) Measurement Method

The rats were accommodated in a measurement cage under rat feeding and water supply on the morning of the day of administration, and accustomed to the measurement environment. After measuring the weight using an electronic scale balance, a lead wire and a connector socket were connected 30 minutes or more before the start of the electroencephalogram measurement, and the rat was accustomed in the measurement state under no anesthesia and no custody. The test compounds were intraperitoneally or orally administered to the rats and the electroencephalogram was measured continuously until 6 hours after the administration.

The doses and administration routes of the compounds are shown below.

Ramelteon: solvent, 0.1 mg/kg, 1 mg/kg, and 10 mg/kg; intraperitoneal administration Example 1: solvent, 3 mg/kg, 30 mg/kg, and 300 mg/kg; oral administration Example 6: solvent, 10 mg/kg, 30 mg/kg, and 300 mg/kg; oral administration The electrical signals of electroencephalogram and of electromyogram were applied to an electroencephalogram system and an electroencephalogram frequency analysis program of a personal computer was used to acquire the wave form of the electroencephalogram from the electroencephalograph system. In addition, the image signals of the electroencephalogram waveform were applied to an EEG video system and recorded on DVD-R using a DVD recorder. The behavior observation was carried out through a video camera at the same time as the electroencephalogram measurement and the images were also recorded on DVD-R using DVD recorder.

(5) Analysis Method (i) Spontaneous Electroencephalogram

The presence or absence of abnormality in the electroencephalogram waveform in up to 6 hours from immediately after the administration, to each animal, respectively, was observed.

(ii) Sleep-Awake Cycle

The analysis of a sleep-awake cycle was carried out using a sleep stage display-supporting program (MTS50061B, Japan Santec Corporation) based on the electroencephalogram waveforms acquired with an electroencephalogram frequency analysis program. Using the index of electroencephalogram, electromyogram, and behavior, the sleep steps were classified into an awake phase, a rest phase, a slow wave light sleep (S.W.L.S.) phase, a slow wave deep sleep (S.W.D.S.) phase, and a fast wave sleep (F.W.S., REM sleep) phase. Further, the rest phase, the slow wave light sleep phase, and the slow wave deep sleep phase were summed to determine a slow wave sleep (S.W.S., Non-REM sleep) phase. The respective sleep steps (the awake phase, the rest phase, the slow wave light sleep phase, the slow wave deep sleep phase, and the fast wave sleep phase), classified in a 20-second unit for up to six hours after the administration from the completion of the administration, were displayed as a histogram, and, for each of the sleep steps, the occupancy was determined. As the assessment criteria in the respective sleep steps, the criteria described in Japanese Pharmacological Journal 84, 25-89 (1984) were used.

(6) Results

As a result of the electroencephalogram analysis test carried out using ramelteon, it was confirmed that there is a tendency that the occupancy of the sleep step of electroencephalogram from a dose of 0.1 mg/kg increases, the occupancy of the respective sleep steps at 1 mg/kg significantly increases, and there is a sleep action. On the other hand, as a result of the test above carried out using the compound of Example 1 of the present invention, it was confirmed that no change in the occupancy in the respective sleep steps of electroencephalogram could be seen at any of the doses, and there was no sleep action.

Further, as a result of the test above carried out using the compound of Example 6, it was confirmed that no change in the occupancy in the respective sleep steps of electroencephalogram could be seen and there was no sleep action at the doses of 10 mg/kg and 30 mg/kg. On the other hand, a variation in the electroencephalogram was observed with the dose of 300 mg/kg.

This indicates that the concentration of the compound of the present invention in the brain does not reach the concentration expressing a sleep action up to a dose of 300 mg/kg of the compound of Example 1 and 30 mg/kg of the compound of Example 6. On the other hand, as shown in Test Example 2, it was confirmed that the compounds of Examples 1 and 6 of the present invention exhibit a good urethral pressure increasing action at a dose of 0.01 mg/kg, and thus, the compounds of Examples 1 and 6 show a urethral pressure increasing action at a dose which does not exhibit a sleep action. These results demonstrates that the $K_{p,uu,CSF}$ values, $K_{p,brain}$ values, $K_{p,uu,CSF,AUC}$ values, and $K_{p,brain,AUC}$ values indicative of the central nervous system penetration, the compounds of the present invention having the $K_{p,uu,CSF}$ values, $K_{p,brain}$ values, $K_{p,uu,CSF,AUC}$ values, and $K_{p,brain,AUC}$ values of 0.1 or less does not exhibit an action on central nervous system diseases at the dose having an action on urinary incontinence, and further, the compounds of Examples 1 and 6 does not exhibit a sleep action or the like when administered at an effective dose in the application of treating urinary incontinence.

From the results of Text Example 1 above, it was confirmed that the compound of the present invention has an $MT_1$ and/or $MT_2$ receptor agonistic action. Further, when some of the compounds were examined for a urethral pressure increasing action, the compounds exhibited the same increasing action as shown in Test Example 2. Incidentally, when some of the compounds were examined for central nervous system penetration, it was confirmed that their central nervous system penetration is low and they do not exhibit an action against central nervous system diseases such as a sleep action in an effective dose in the application of treating urinary incontinence as shown in Text Examples 3 and 4. Therefore, it is expected that the compound of the formula (I) can be used for the treatment or prevention of urinary incontinence, and preferably of stress urinary incontinence and a mixed type of urinary incontinence.

A pharmaceutical composition including one or two or more kinds of the compound of the formula (I) or a salt thereof as an active ingredient can be prepared using excipients that are usually used in the art, that is, excipients for pharmaceutical preparation, carriers for pharmaceutical preparation, and the like, according to the methods usually used.

Administration can be accomplished either by oral administration via tablets, pills, capsules, granules, powders, solutions, and the like, or parenteral administration via injections, such as intraarticular, intravenous, or intramuscular injections, and the like, suppositories, eye drops, eye ointments, transdermal liquid preparations, ointments, transdermal patches, transmucosal liquid preparations, transmucosal patches, inhalers, and the like.

As a solid composition for oral administration, tablets, powders, granules, and the like are used. In such a solid composition, one or two or more kinds of the active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or with a film of a gastric or enteric coating substance.

The liquid composition for oral administration includes pharmaceutically acceptable emulsions, solutions, suspensions, syrups, elixirs, or the like, and also includes generally used inert diluents, for example, purified water or ethanol. In addition to the inert diluent, the liquid composition may also include auxiliary agents such as a solubilization assisting agent, a moistening agent, and a suspending agent, sweeteners, flavors, aromatics, and antiseptics.

The injections for parenteral administration include sterile aqueous or non-aqueous solution preparations, suspensions, or emulsions. The aqueous solvent includes, for example, distilled water for injection and physiological saline. Examples of the non-aqueous solvent include alcohols such as ethanol. Such a composition may further include a tonicity agent, an antiseptic, a moistening agent, an emulsifying agent, a dispersing agent, a stabilizing agent, or a solubilizing assisting agent. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

Usually, in the case of oral administration, the daily dose is from about 0.001 to 100 mg/kg, preferably from 0.1 to 30 mg/kg, and more preferably from 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once or plural times a day. The dose is appropriately decided in response to the individual case by taking the symptoms, the age, and the gender, and the like into consideration.

Although there are differences depending on a route of administration, a dosage form, an administration site, and a type of the excipient or additive, a pharmaceutical composition of the present invention comprises 0.01 to 100% by weight of, as an embodiment, 0.01 to 50% by weight of, one or more of the compound of the formula (I) or a salt thereof which is the active ingredient.

The compound of the formula (I) may be used in combination with various agents for preventing or treating diseases on which the compound of the formula (I) is considered to show the effect. Such the combined preparations may be administered simultaneously, or separately and continuously, or at a desired time interval. The preparations to be co-administered may be a blend, or may be prepared individually.

EXAMPLES

Hereinbelow, the preparation methods for the compound of the formula (I) will be described in more detail with reference to Examples. Further, the present invention is not limited to the compounds described in the Examples below. Further, the preparation processes for the starting compounds will be each described in Preparation Examples. In addition, the preparation methods for the compound of the formula (I) are not limited to the preparation methods of the specific Examples shown below, but the compound of the formula (I) can be prepared by a combination of these preparation methods or a method that is apparent to a person skilled in the art.

Furthermore, the following abbreviations may be used in some cases in Examples, Preparation Examples, and Tables below.

PEx: Preparation Example No., Ex: Example No., PSyn: Preparation Example No. prepared by the same method (for example, in the case where Psyn is "PEx3", prepared by the same method as in Preparation Example 3), Syn: Example No. prepared by the same method (for example, in the case where Syn is "Ex1", prepared by the same method as in Example 1), Str: Structural chemical formula (Me represents methyl, Et represents ethyl, nPr: normal propyl, cPr: cyclopropyl, Boc: tert-butyloxycarbonyl, Ts: p-toluenesulfonyl, TMS: trimethylsilyl, and TBDPS: tert-butyldiphenylsilyl), DAT: Physicochemical data, ESI+: m/z values in mass spectroscopy (Ionization ESI, representing [M+H]$^+$ unless otherwise specified), ESI−: m/z values in mass spectroscopy (Ionization ESI, representing [M−H]$^-$ unless otherwise specified), APCI/ESI+: APCI/ESI-MS [M+H]$^+$ (atmospheric pressure chemical ionization APCI, and APCI/ESI means simultaneous measurement of APCI and ESI and represents [M+H]$^+$ unless otherwise specified), APCI/ESI−: APCI/ESI-MS [M−H]$^-$ (atmospheric pressure chemical ionization APCI, and APCI/ESI means simultaneous measurement of APCI and ESI and represents [M−H]$^-$ unless otherwise specified), 1H-NMR (DMSO-d$_6$): signal δ (ppm) in $^1$H NMR in DMSO-d$_6$, 1H-NMR (CDCl$_3$): signal δ (ppm) in $^1$H NMR in CDCl$_3$, s: singlet, d: doublet, t: triplet, q: quartet, br: broad line (e.g.: brs), and m: multiplet. Further, in the case where both of compounds represented by two structural formulae are shown as a Preparation Example compound, an additional description 'and' in the structural formula denotes that the compounds represented by the structural formulae are obtained as a mixture. In addition, HCl in the structural formula represents that the compound is monohydrochloride.

Further, in the present specification, a nomenclature software such as ACD/Name (registered trademark, Advanced Chemistry Development, Inc.) may be used for nomenclature of compounds in some cases.

The X-ray powder diffraction was measured using RINT-TTRII under the conditions of a tube of Cu, a tube current of 300 mA, a tube voltage of 50 kV, a sampling width of 0.020°, a scanning speed of 4°/min, a wavelength of 1.54056 angstroms, and a measurement diffraction angle (2θ) of 2.5° to 40°. The operation of the equipments, including data processing, is according to the method and the procedure instructed for each of equipment.

With respect to the numerical values obtained from various patterns, some errors may occur due to the direction of crystal growth, the particle size, the measurement conditions, or the like. Thus, such errors are taken into account and, in the present specification, the term "around" used in the values of the diffraction angles (2θ) in the X-ray powder diffraction pattern means that the error range which is usually accepted in this data measurement method is included and means an approximate value, in one embodiment, it means a range of the value ±0.2°. Further, with the X-ray powder diffraction patterns, the interval of crystal lattice and the overall patterns are important for identification of crystals in terms of the properties of the data, and since the diffraction angle and the diffraction intensity may vary slightly depending on the direction of crystal growth, the particle size, and the measurement conditions, it should not be strictly construed.

In addition, for a convenience, a concentration of mol/L is represented by M. For example, a 1 M aqueous sodium hydroxide solution means a 1 mol/L aqueous sodium hydroxide solution.

Preparation Example 1

To 50.0 mL of methanesulfonic acid was added 9.10 g of methionine at room temperature, followed by stirring. Then, 4.70 g of 7-fluoro-6-methoxy-2,3,4,9-tetrahydro-1H-β-carbolin-1-one was added thereto, followed by stirring at 65° C. overnight. The reaction mixture was added portionwise to ice water, followed by stirring, and the precipitated solid was collected by filtration. The obtained solid was washed with water and dried under reduced pressure to obtain 4.53 g of 7-fluoro-6-hydroxy-2,3,4,9-tetrahydro-1H-β-carbolin-1-one as a solid.

Preparation Example 2

A mixture of 1.00 g of 5-hydroxy-2-methoxypyridine, 7.06 mL of 1,2-dibromoethane, 11.0 g of potassium carbonate, and 20.0 mL of acetonitrile was heated to 60° C. and stirred overnight. The reaction mixture was cooled to room temperature, the solid was separated by filtration, and the filtrate was concentrated under reduced pressure. The obtained residue was purified by silica gel column chromatography (hexane:ethyl acetate=90:10 to 50:50) to obtain 1.63 g of 5-(2-bromoethoxy)-2-methoxypyridine as an oily substance.

Preparation Example 3

A mixture of 3.20 g of N-[2-(5-hydroxy-1H-indol-3-yl)ethyl]acetamide, 12.6 mL of 1,2-dibromoethane, 57.3 g of cesium carbonate, and 64.0 mL of dimethyl formamide was heated to 70° C., followed by stirring for 4 hours. The reaction mixture was cooled to room temperature, and then a saturated aqueous sodium hydrogen carbonate solution was added thereto, followed by extraction with ethyl acetate. The organic layer was washed with saturated aqueous sodium chloride solution and concentrated under reduced pressure. The obtained residue was purified by silica gel column chromatography (chloroform:methanol=100:0 to 20:1) to obtain 301 mg of N-{2-[5-(2-bromoethoxy)-1H-indol-3-yl]ethyl}acetamide as an oily substance.

Preparation Example 4

In a mixture of 84 mL of dimethyl formamide and 90 mL of 4.5 M hydrochloric acid was suspended 14.0 g of 4-(benzyloxy) aniline hydrochloride. To the obtained mixture was slowly added 22.9 mL of an aqueous solution of 4.51 g of sodium nitrite under ice-cooling, followed by stirring for 2.5 hours under ice-cooling (solution A). To 11.0 g of ethyl 2-oxopiperidine-3-carboxylate was added 72.5 mL of a 1 M aqueous potassium hydroxide solution, followed by stirring at room temperature for 1.5 hours (solution B). To the previously obtained solution A was added the solution B under ice-cooling, followed by adjusting to pH 4.6 by the addition of a saturated aqueous sodium acetate solution, and stirring for 4 hours under ice-cooling. The precipitated solid was collected by filtration to obtain 5.94 g of 3-{[4-(benzyloxy)phenyl]hydrazono}piperidin-2-one (a mixture of E and Z isomers) as a solid.

Preparation Example 5

In 45 mL of a 80% aqueous formic acid solution was dissolved 5.57 g of 3-{[4-(benzyloxy)phenyl]hydrazono}piperidin-2-one (a mixture of E and Z isomers), followed by heating and stirring at 100° C. for 1 hour. The reaction mixture was cooled to room temperature and then ice-cooled, water was added thereto, and the precipitated solid was collected by filtration to obtain 3.44 g of 6-(benzyloxy)-2,3,4,9-tetrahydro-1H-β-carbolin-1-one as a solid.

Preparation Example 6

In a mixture of 30 mL of ethanol and 30 mL of water was suspended 5.79 g of 6-(benzyloxy)-2,3,4,9-tetrahydro-1H-β-carbolin-1-one, and 10.3 g of potassium hydroxide was added thereto, followed by stirring at 105° C. for 7 hours. The reaction mixture was cooled to room temperature and ice-cooled, 9.06 mL of acetic acid was added thereto, and the precipitated solid was collected by filtration to obtain 5.67 g of 3-(2-aminoethyl)-5-(benzyloxy)-1H-indole-2-carboxylic acid as a solid.

Preparation Example 7

In a mixture of 18 mL of tetrahydrofuran and 18 mL of water was suspended 5.67 g of 3-(2-aminoethyl)-5-(benzyloxy)-1H-indole-2-carboxylic acid, and 4.61 g of sodium hydrogen carbonate and 5.19 g of di-tert-butyl dicarbonate were added thereto, followed by stirring at room temperature for 5 hours. The reaction mixture was concentrated under reduced pressure and then adjusted to be weakly acidic by adding 1 M hydrochloric acid, followed by extraction with ethyl acetate. The obtained organic layer was washed with saturated aqueous sodium chloride solution, dried over anhydrous sodium sulfate, and concentrated under reduced pressure. The obtained solid was washed with hexane:ethyl acetate=90:10 to obtain 7.04 g of 5-(benzyloxy)-3-{2-[(tert-butoxycarbonyl)amino]ethyl}-1H-indole-2-carboxylic acid as a solid.

Preparation Example 8

In 98.9 mL of dimethyl formamide were dissolved 7.00 g of 5-(benzyloxy)-3-(2-[(tert-butoxycarbonyl)amino]ethyl)-1H-indole-2-carboxylic acid, 8.75 mL of N,N-diisopropylethylamine, and 2.50 g of methylamine hydrochloride, and 7.13 g of O-(7-azabenzotriazol-1-yl)-N,N,N',N'-tetramethyluronium hexafluorophosphate was added thereto, followed by stirring at room temperature for 5 hours. To the reaction mixture was added water and the precipitated solid was collected by filtration to obtain 6.87 g of tert-butyl {2-[5-(benzyloxy)-2-(methylcarbamoyl)-1H-indol-3-yl]ethyl}carbamate as a solid.

Preparation Example 9

In 30 mL of dioxane was suspended 6.87 g of tert-butyl {2-[5-(benzyloxy)-2-(methylcarbamoyl)-1H-indol-3-yl]ethyl}carbamate, and 30 mL of hydrogen chloride (4 M dioxane solution) was added thereto, followed by stirring at room temperature overnight. The solvent was evaporated under reduced pressure to obtain 6.10 g of 3-(2-aminoethyl)-5-(benzyloxy)-N-methyl-1H-indole-2-carboxamide hydrochloride as a solid.

Preparation Example 10

Under an argon atmosphere, to a mixture of 4.00 g of 2-chloropyrazine, 27.3 mL of ethylene glycol, and 60.0 mL of dioxane was added 4.70 g of potassium tert-butoxide under ice-cooling, followed by stirring at 60° C. overnight. The reaction mixture was cooled to room temperature and then concentrated under reduced pressure, and to the obtained residue was added an aqueous ammonium chloride solution, followed by extraction with chloroform. The organic layer was washed with saturated aqueous sodium chloride solution and the organic layer was concentrated under reduced pressure. The obtained residue was purified by silica gel column chromatography (hexane/ethyl acetate=30:70 to 0:100) to obtain 2.77 g of 2-(pyrazin-2-yloxy)ethanol as an oily substance.

Preparation Example 11

In a mixture of 60.0 mL of dioxane and 60.0 mL of water was suspended 12.0 g of 3-(2-aminoethyl)-5-(benzyloxy)-1H-indole-2-carboxylic acid, and 18.9 mL of triethylamine and 12.0 g of N-[2-(trimethylsilyl)ethoxycarbonyloxy]succinimide were added thereto, followed by stirring at room temperature overnight. After the completion of the reaction, the reaction mixture was concentrated under reduced pressure until the volume reached a half thereof. The reaction mixture was adjusted to be acidic by adding 1 M hydrochloric acid and then ethyl acetate was added thereto. The precipitated solid was separated by filtration and the filtrate was extracted with ethyl acetate. The organic layer was washed with saturated aqueous sodium chloride solution, dried over anhydrous sodium sulfate, and then concentrated under reduced pressure. The obtained solid was washed with hexane:ethyl acetate=5:1 to obtain 13.8 g of 5-(benzyloxy)-3-[2-({[2-(trimethylsilyl)ethoxy]carbonyl}amino)ethyl]-1H-indole-2-carboxylic acid as a solid.

Preparation Example 12

A mixture of 4.90 g of 1-methyl-1H-pyrazol-3-ol, 17.6 mL of 2-bromoethanol, 34.5 g of potassium carbonate, and 73.5 mL of acetonitrile was stirred overnight under heating and refluxing. The reaction mixture was cooled to room temperature, and the solid was separated by filtration and washed with ethyl acetate. The filtrate was concentrated under reduced pressure. The obtained residue was purified by silica gel column chromatography (hexane:ethyl acetate=60:40 to 10:90) to obtain 3.33 g of 2-[(1-methyl-1H-pyrazol-3-yl)oxy]ethanol as an oily substance.

Preparation Example 13

To 12.0 mL of dimethyl formamide were added 400 mg of N-(2-{5-(2-bromoethoxy)-6-fluoro-1-[(4-methylphenyl)sulfonyl]-1H-indol-3-yl}ethyl)acetamide, 220 mg of 5-fluoro-6-methoxy-3-pyridinol, and 800 mg of cesium carbonate, followed by heating to 70° C. and stirring for 3 hours. The reaction mixture was cooled to room temperature, and water was added thereto, followed by extraction with ethyl acetate. The organic layer was washed with water and then concentrated under reduced pressure, and the obtained residue was purified by silica gel column chromatography (chloroform:methanol=100:0 to 90:10) to obtain 348 mg of N-[2-(6-fluoro-5-{2-[(5-fluoro-6-methoxypyridin-3-yl)oxy]ethoxy}-1-[(4-methylphenyl)sulfonyl]-1H-indol-3-yl)ethyl]acetamide as a solid.

Preparation Example 14

A mixture of 300 mg of N-[(2R)-2-({6-fluoro-5-hydroxy-1-[(4-methylphenyl)sulfonyl]-1H-indol-3-yl}propyl]acetamide, 726 mg of cesium carbonate, 215 mg of 1-(2-chloroethyl)-3-methyl-1H-pyrazole, 28.0 mg of tetrabutylammonium iodide, and 6.00 mL of dimethyl formamide was stirred at 50° C. for 18 hours. The reaction mixture was cooled to room temperature, 6 mL of water was added thereto, and the precipitated solid was collected by filtration and washed with water:dimethyl formamide=1:1 to obtain 245 mg of N-[(2R)-2-{6-fluoro-1-[(4-methylphenyl)sulfonyl]-5-[2-(3-methyl-1H-pyrazol-1-yl)ethoxy]-1H-indol-3-yl}propyl]acetamide as a solid.

Preparation Example 15

A mixture of 2.49 g of 2-[(2R)-2-(6-fluoro-5-methoxy-1H-indol-3-yl)propyl]-1H-isoindol-1,3(2H)-dione, 17.7 g of hydrazine monohydrate, and 75.0 mL of methanol was stirred at room temperature for 2 hours. To the reaction mixture was added 100 mL of a 1 M aqueous sodium hydroxide solution, followed by extraction with chloroform. The organic layer was washed with saturated aqueous sodium chloride solution, the solvent was concentrated under reduced pressure, and then the obtained residue was purified by amino silica gel column chromatography (chloroform:methanol=100:0 to 50:1 to 30:1) to obtain 1.28 g of (2R)-2-(6-fluoro-5-methoxy-1H-indol-3-yl)propan-1-amine as an oily substance.

Preparation Example 16

7.59 g of 1-{2-[5-(benzyloxy)-1H-indol-3-yl]ethyl}-3-methylurea was added to a mixture of 380 mL of ethanol and 76.0 mL of tetrahydrofuran, and 1.24 g of 10/o palladium on carbon (54% aqueous) was added thereto under an argon gas flow, followed by stirring at room temperature for 1 hour under a hydrogen atmosphere. The catalyst was separated by filtration and the solvent was evaporated under reduced pressure to obtain 5.93 g of 1-[2-(5-hydroxy-1H-indol-3-yl)ethyl]-3-methylurea as a solid.

Preparation Example 17

A mixture of 5.65 g of (3R)-4-(1,3-dioxo-1,3-dihydro-2H-isoindol-2-yl)-3-methylbutanal, 4.70 g of (3-fluoro-4-methoxyphenyl)hydrazine hydrochloride, and 141 mL of acetic acid was stirred for 2 hours under refluxing. The reaction mixture was cooled to room temperature and then concentrated under reduced pressure. To the obtained residue was added 500 mL of chloroform, followed by washing with 400 mL of a 1 M aqueous sodium hydroxide solution. The organic layer was washed with saturated aqueous sodium chloride solution, dried over anhydrous sodium sulfate, and concentrated under reduced pressure. The obtained residue was purified by silica gel column chromatography (hexane:ethyl acetate=100:0 to 4:1 to 2:1) to obtain 2.49 g of 2-[(2R)-2-(6-fluoro-5-methoxy-1H-indol-3-yl)propyl]-1H-isoindol-1,3(2H)-dione as a solid.

Preparation Example 18

Under an argon atmosphere, to a mixture of 123 mL of dichloromethane and 123 mL of dimethylsulfoxide were added 8.41 g of 2-[(2R)-4-hydroxy-2-methylbutyl]-1H-isoindol-1,3(2H)-dione and 15.1 mL of triethylamine, followed by ice-cooling, and then a solution in which 17.2 g of a sulfurtrioxide-pyridine complex was dissolved in 123 mL of dimethylsulfoxide was added dropwise thereto over 10 minutes. After the completion of dropwise addition, the mixture was warmed to room temperature and stirred for 4 hours. The reaction mixture was poured into water, followed by extraction with ethyl acetate. The organic layer was washed with saturated aqueous sodium chloride solution, dried over anhydrous sodium sulfate, and concentrated under reduced pressure. The obtained residue was purified by silica gel column chromatography (hexane:ethyl acetate=100:0 to 4:1) to obtain 5.65 g of (3R)-4-(1,3-dioxo-1,3-dihydro-2H-isoindol-2-yl)-3-methylbutanal as an oily substance.

Preparation Example 19

Under an argon atmosphere, to a mixture of 28.8 g of (2R)-4-{[tert-butyl(diphenyl)silyl]oxy}-2-methylbutan-1-ol, 16.1 g of phthalimide, 28.6 g of triphenyl phosphine, and 500 mL of tetrahydrofuran was added dropwise a mixture of 23.8 g of diisopropyl azodicarboxylate and 50.0 mL of toluene over 30 minutes under ice-cooling. After the completion of dropwise addition, the mixture was warmed to room temperature, followed by stirring for 1.5 hours. The reaction mixture was concentrated under reduced pressure and the obtained residue was purified by silica gel column chromatography (hexane:ethyl acetate=100:0 to 90:1 to 84:16) to obtain 39.7 g of 2-[(2R)-4-({[tert-butyl(diphenyl)silyl]oxy}-2-methylbutyl]-1H-isoindol-1,3(2H)-dione as a solid.

Preparation Example 20

In 11.8 mL of tetrahydrofuran was dissolved 1.28 g of (2R)-2-(6-fluoro-5-methoxy-1H-indol-3-yl)propan-1-amine, and 11.8 mL of a 1 M aqueous sodium hydroxide solution and 1.09 mL of acetic anhydride were added thereto, followed by stirring at room temperature for 3 hours. The reaction mixture was extracted with chloroform, the organic layer was concentrated under reduced pressure, and then the obtained residue was purified by silica gel column chromatography (chloroform:methanol=100:1 to 30:1) to obtain 1.57 g of N-[(2R)-2-(6-fluoro-5-methoxy-1H-indol-3-yl)propyl]acetamide as an oily substance.

Preparation Example 21

Under an argon atmosphere, in 60.0 mL of dichloromethane was dissolved 1.95 g of N-(2-{5-methoxy-2-methyl-1-[(4-methylphenyl)sulfonyl]-1H-indol-3-yl}ethyl)propanamide, and 10.0 mL of boron tribromide (a 1.0 M dichloromethane solution) was added dropwise thereto under ice-cooling, followed by stirring for 45 minutes under ice-cooling. To the reaction mixture was added methanol, and water was added thereto, followed by extraction with chloroform. The organic layer was concentrated under reduced pressure and then the obtained residue was purified by silica gel column chromatography (chloroform:methanol=97:3 to 92:8) to obtain 1.51 g of N-(2-{5-hydroxy-2-methyl-1-[(4-methylphenyl)sulfonyl]-1H-indol-3-yl}ethyl)propanamide as a solid.

Preparation Example 22

A mixture of 3.00 g of 7-fluoro-6-hydroxy-2,3,4,9-tetrahydro-1H-β-carbolin-1-one, 2.82 g of potassium carbonate, 4.19 g of 3-(2-bromoethoxy)-1-methyl-1H-pyrazole, and 60.0 mL of dimethylformamide was stirred at 70° C. overnight. The reaction mixture was cooled to room temperature and then water was added thereto. The precipitated solid was collected by filtration and washed with water. To a mixture of the obtained solid, 6.94 mL of ethanol, and 6.94 mL of water was added 1.98 g of potassium hydroxide, followed by stirring at 105° C. for 24 hours. The reaction mixture was cooled to room temperature and then ice-cooled, 2.53 mL of concentrated hydrochloric acid was added thereto, and the reaction mixture was concentrated under reduced pressure. To the residue was added 18.8 mL of 4 M hydrochloric acid, followed by stirring at 90° C. for 5 hours. The reaction mixture was cooled to room temperature, adjusted to be basic by the addition of potassium carbonate, and then extracted with chloroform, and the organic layer was concentrated under reduced pressure. The obtained residue was purified by amino silica gel column chromatography (chloroform:methanol=99:1 to 92:8) to obtain 536 mg of 2-(6-fluoro-5-{2-[(1-methyl-1H-pyrazol-3-yl)oxy]ethoxy}-1H-indol-3-yl)ethanamine as a solid.

Preparation Example 23

To 12.0 mL of dimethylformamide were added 600 mg of 2-({3-(2-acetamidoethyl)-1-[(4-methylphenyl)sulfonyl]-1H-indol-5-yl}oxy)ethyl 4-methylbenzenesulfonate, 230 mg of 3-fluoro-5-hydroxy-2-methoxypyridine, and 700 mg of potassium carbonate, followed by heating to 70° C. and stirring for 1.5 hours. The reaction mixture was cooled to room temperature and water was added thereto, followed by extraction with ethyl acetate. The organic layer was washed with water and then concentrated under reduced pressure, and the obtained residue was purified by silica gel column chromatography (chloroform:methanol=100:0 to 90:10), and further purified by amino silica gel column chromatography (chloroform:ethyl acetate=100:0 to 0:100) to obtain 515 mg of N-[2-(5-{2-[(5-fluoro-6-methoxypyridin-3-yl)oxy]ethoxy}-1-[(4-methylphenyl)sulfonyl]-1H-indol-3-yl)ethyl]acetamide as a solid.

Preparation Example 24

A mixture of 200 mg of N-(2-{5-hydroxy-2-methyl-1-[(4-methylphenyl)sulfonyl]-1H-indol-3-yl}ethyl)acetamide, 505 mg of cesium carbonate, 158 mg of ethyl 2-chloroethylcarbamate, 9.00 mg of potassium iodide, and 4.00 mL of dimethyl formamide was stirred at 50° C. overnight. The reaction mixture was cooled to room temperature and water was added thereto, followed by extraction with chloroform. The organic layer was concentrated under reduced pressure and the obtained residue was purified by silica gel column chromatography (chloroform:methanol=99:1 to 93:7) to obtain 182 mg of ethyl [2-({3-(2-acetamidoethyl)-2-methyl-1-[(4-methylphenyl)sulfonyl]-1H-indol-5-yl}oxy)ethyl]carbamate as a solid.

Preparation Example 25

A mixture of 3.20 g of N-[2-(6-fluoro-5-methoxy-1H-indol-3-yl)ethyl]acetamide, 1.20 mL of a 50% aqueous sodium hydroxide solution, 480 mg of tetrabutyl ammonium hydrogen sulfate, and 51.0 mL of tetrahydrofuran was stirred at room temperature for 10 minutes. 3.20 g of p-toluenesulfonylchloride was added thereto, followed by stirring vigorously for 1 hour. The reaction mixture was diluted by adding water, and the precipitated solid was collected by filtration and washed with water and diethyl ether to obtain 4.42 g of N-(2-{6-fluoro-5-methoxy-1-[(4-methylphenyl)sulfonyl]-1H-indol-3-yl}ethyl)acetamide as a solid.

Preparation Example 26

In 8.00 mL of dimethylformamide were suspended 400 mg of N-(2-{5-hydroxy-2-methyl-1-[(4-methylphenyl)sulfonyl]-1H-indol-3-yl}ethyl)propanamide and 650 mg of cesium carbonate, and to the mixture was added 300 mg of 3-(2-bromoethoxy)-1-methyl-1H-pyrazole, followed by stirring at room temperature for 8 hours. To the reaction mixture was added water, followed by extraction with ethyl acetate. The organic layer was washed with water and concentrated under reduced pressure, and the obtained residue was purified by silica gel column chromatography (chloroform:methanol=99:1 to 92:8) to obtain 596 mg of N-[2-(2-methyl-1-[(4-methylphenyl)sulfonyl]-5-{2-[(1-methyl-1H-pyrazol-3-yl)oxy]ethoxy}-1H-indol-3-yl)ethyl]propanamide.

Preparation Example 27

A mixture of 700 mg of N-(2-{6-fluoro-5-hydroxy-1-[(4-methylphenyl)sulfonyl]-1H-indol-3-yl}ethyl)acetamide, 1.50 mL of 1,2-dibromoethane, 1.40 g of cesium carbonate, and 14.0 mL of dimethylformamide was stirred at room temperature for 5 hours, followed by the addition of 1.50 mL of 1,2-dibromoethane and 1.50 g of cesium carbonate thereto, and further stirring at room temperature overnight. To the reaction mixture was added water, and the precipitated solid was collected by filtration and washed with diethyl ether to obtain 918 mg of N-(2-{5-(2-bromoethoxy)-6-fluoro-1-[(4-methylphenyl)sulfonyl]-1H-indol-3-yl}ethyl)acetamide as a solid.

Preparation Example 28

To 140 mL of tetrahydrofuran was mixed 13.8 g of 2-[5-(benzyloxy)-1H-indol-3-yl]ethanamine, and 12.7 g of 1,1'-carbonyldiimidazole was added thereto, followed by stirring at room temperature for 30 minutes. 55.0 mL of methylamine (9.8 M methanol solution) was added thereto, followed by stirring at room temperature for 16 hours. The reaction mixture was concentrated under reduced pressure and then the obtained residue was diluted with chloroform. The organic layer was washed with water and then concentrated under reduced pressure. To the obtained residue was added diisopropylether, and then the mixture was concentrated under reduced pressure. The obtained solid was collected by filtration and washed with diisopropylether to obtain 13.0 g of 1-{2-[5-(benzyloxy)-1H-indol-3-yl]ethyl}-3-methylurea as a solid.

Preparation Example 29

In 65.0 mL of dichloromethane were dissolved 2.71 g of 2-(5-methoxy-2-methyl-1H-indol-3-yl)ethanamine and 5.00 mL of triethylamine, and 2.50 mL of propionic anhydride was added thereto, followed by stirring at room temperature overnight. To the reaction mixture was added water, followed by extraction with chloroform. The organic layer was concentrated under reduced pressure and then the obtained residue was purified by silica gel column chromatography (chloroform:methanol=97:3 to 92:8) to obtain 2.73 g of N-[2-(5-methoxy-2-methyl-1H-indol-3-yl)ethyl]propanamide.

Preparation Example 30

In 160 mL of tetrahydrofuran was dissolved 39.7 g of 2-[(2R)-4-{[tert-butyl(diphenyl)silyl]oxy}-2-methylbutyl]-1H-isoindol-1,3(2H)-dione, and 124 mL of tetrabutylammonium fluoride (a 1 M tetrahydrofuran solution) was added thereto, followed by stirring at room temperature for 5 hours. The reaction mixture was concentrated under reduced pressure and the obtained residue was purified by silica gel column chromatography (chloroform:methanol=100:0 to 90:10 to 30:1) to obtain 8.43 g of 2-[(2R)-4-hydroxy-2-methylbutyl]-1H-isoindol-1,3(2H)-dione as an oily substance.

Preparation Example 31

To 10.0 mL of acetonitrile were added 400 mg of N-(2-{5-(2-bromoethoxy)-1-[(4-methylphenyl)sulfonyl]-1H-indol-3-yl}propyl)acetamide, 160 mg of 1-methyl-1H-pyrazol-3-ol and 870 mg of cesium carbonate, followed by heating to 70° C. and stirring for 3 hours. The reaction mixture was cooled to room temperature and water was added thereto, followed by extraction with ethyl acetate. The organic layer was concentrated under reduced pressure and the obtained residue was purified by silica gel column chromatography (chloroform:methanol=100:0 to 90:10) to obtain 268 mg of N-[2-(1-[(4-methylphenyl)sulfonyl]-5-{2-[(1-methyl-1H-pyrazol-3-yl)oxy]ethoxy}-1H-indol-3-yl)propyl]acetamide as a solid.

Preparation Example 32

Under an argon atmosphere, a mixture of 215 mg of 2-(trimethylsilyl)ethyl [2-(5-hydroxy-2-methyl-1H-indol-3-yl)ethyl]carbamate, 137 mg of 2-[(1-methyl-1H-pyrazol-3-yl)oxy]ethanol, 355 µL of cyanomethylene tributylphosphorane, and 4.30 mL of toluene was stirred for 6 hours under heating and refluxing. The reaction mixture was cooled to room temperature and then concentrated under reduced pressure, and the obtained residue was purified by silica gel column chromatography (hexane:ethyl acetate=95:5 to 55:45) to obtain 260 mg of 2-(trimethylsilyl)ethyl [2-(2-methyl-5-{2-[(1-methyl-1H-pyrazol-3-yl)oxy]ethoxy}-1H-indol-3-yl)ethyl]carbamate as an oily substance.

Preparation Example 33

In 2.00 mL of dichloromethane was dissolved 260 mg of 2-(trimethylsilyl)ethyl [2-(2-methyl-5-{2-[(1-methyl-1H-pyrazol-3-yl)oxy]ethoxy}-1H-indol-3-yl)ethyl]carbamate, and 1.50 mL of trifluoroacetate was added thereto, followed by stirring at room temperature for 2 hours. To the reaction mixture was added a saturated aqueous sodium hydrogen carbonate solution, followed by extraction with chloroform, and the aqueous layer was saturated with potassium carbonate and extracted with ethyl acetate. To the organic layer was added anhydrous sodium sulfate, the solid was separated by filtration, and then amino silica gel was added thereto, followed by concentrating under reduced pressure. The obtained residue was purified by amino silica gel column chromatography (chloroform:methanol=100:0 to 95:5) to obtain 176 mg of 2-(2-methyl-5-{2-[(1-methyl-1H-pyrazol-3-yl)oxy]ethoxy}-1H-indol-3-yl)ethanamine as an oily substance.

Preparation Example 34

Under an argon gas flow, to a mixture of 584 mg of 2-(trimethylsilyl)ethyl {2-[5-(benzyloxy)-2-(hydroxymethyl)-1H-indol-3-yl]ethyl}carbamate, 409 mg of palladium (II) chloride, 12.0 mL of tetrahydrofuran, and 1.20 mL of methanol was added 175 mg of sodium borohydride, followed by stirring at room temperature for 3 hours. To the reaction mixture was added water, and the insoluble materials were separated by filtration through celite. The obtained filtrate was extracted with ethyl acetate, and the organic layer was dried over anhydrous sodium sulfate and concentrated under reduced pressure. The obtained residue was mixed with 940 mg of palladium (II) chloride, 30.0 mL of tetrahydrofuran, and 3.00 mL of methanol under an argon gas flow, and 401 mg of sodium borohydride was added thereto, followed by stirring at room temperature for 1.5 hours. To the reaction mixture was added water, and the insoluble materials were separated by filtration through celite. The obtained filtrate was extracted with ethyl acetate, and the organic layer was dried over anhydrous sodium sulfate and concentrated under reduced pressure. The obtained residue was purified by silica gel column chromatography (hexane:ethyl acetate=90:10 to 40:60) to obtain 327 mg of 2-(trimethylsilyl)ethyl [2-(5-hydroxy-2-methyl-1H-indol-3-yl)ethyl]carbamate as an oily substance.

Preparation Example 35

In 20.3 mL of tetrahydrofuran was dissolved 1.02 g of 5-(benzyloxy)-3-[2-({[2-(trimethylsilyl)ethoxy]

carbonyl}amino)ethyl]-1H-indole-2-carboxylic acid, and 725 mg of 1,1'-carbonyldiimidazole was added thereto, followed by stirring at room temperature for 2 hours. The reaction mixture was ice-cooled, and then to the reaction mixture was added dropwise 2.54 mL of an aqueous sodium borohydride (254 mg) solution, followed by stirring for 1 hour under ice-cooling. To the reaction mixture was added a saturated aqueous ammonium chloride solution, followed by stirring for 10 minutes and then extraction with ethyl acetate. The organic layer was washed with a saturated aqueous sodium hydrogen carbonate solution and a saturated aqueous sodium chloride solution, dried over anhydrous magnesium sulfate, and concentrated under reduced pressure. The obtained residue was purified by silica gel column chromatography (hexane:ethyl acetate=80:20 to 60:40) to obtain 797 mg of {2-(trimethylsilyl)ethyl(2-[5-(benzyloxy)-2-(hydroxymethyl)-1H-indol-3-yl]ethyl}carbamate as a solid.

Preparation Example 36

To a mixture of 2.73 g of N-[2-(5-methoxy-2-methyl-1H-indol-3-yl)ethyl]propanamide, 27.0 mL of a 500/0 aqueous sodium hydroxide solution, 480 mg of benzyltriethylammonium chloride, and 54.0 mL of tetrahydrofuran was added 3.00 g of p-toluenesulfonyl chloride, followed by stirring vigorously for 1 hour, adding 3.00 g of p-toluene sulfonyl chloride thereto, and further stirring vigorously for 1 hour. 3.00 g of p-toluene sulfonyl chloride was added thereto, followed by further stirring vigorously for 1 hour. To the reaction mixture was added water, followed by extraction with chloroform. The organic layer was concentrated under reduced pressure and then the obtained residue was purified by silica gel column chromatography (chloroform:methanol=99:1 to 93:7) to obtain 2.29 g of N-(2-{5-methoxy-2-methyl-1-[(4-methylphenyl)sulfonyl]-1H-indol-3-yl}ethyl)propanamide as an amorphous substance.

Preparation Example 37

Under a nitrogen atmosphere, a mixture of 500 mg of (3-fluoro-4-methoxyphenyl)hydrazine hydrochloride, 358 μL of 5-chloro-2-pentanone, 20.0 mL of ethanol, and 4.00 mL of water was heated and refluxed overnight. The reaction mixture was cooled to room temperature and then concentrated under reduced pressure. To the obtained residue was added water, then adjusted to be alkaline with a 1 M aqueous sodium hydroxide solution, and extracted with chloroform. The organic layer was concentrated under reduced pressure and the obtained residue was purified by amino silica gel column chromatography (chloroform:methanol=98:2 to 93:7) to obtain 569 mg of a mixture of 2-(6-fluoro-5-methoxy-2-methyl-1H-indol-3-yl)ethanamine and 2-(4-fluoro-5-methoxy-2-methyl-1H-indol-3-yl)ethanamine as an oily substance.

Preparation Example 38

A mixture of 2.00 g of N-[2-(5-hydroxy-1H-indol-3-yl)ethyl]acetamide, 10.0 g of 1,2-bis(4-methylbenzenesulfonyloxy)ethane, 12.0 g of cesium carbonate, and 60.0 mL of dimethylformamide was heated to 80° C. and stirred for 1 hour. The reaction mixture was cooled to room temperature and to the reaction mixture was added ethyl acetate. The organic layer was washed with a saturated aqueous sodium hydrogen carbonate solution and saturated aqueous sodium chloride solution, dried over anhydrous sodium sulfate, and then concentrated under reduced pressure. The obtained residue was purified by silica gel column chromatography (chloroform:methanol=100:0 to 95:5 to 10:1) to obtain 2.40 g of 2-{[3-(2-acetamidoethyl)-1H-indol-5-yl]oxy}ethyl 4-methylbenzenesulfonate as an oily substance.

Preparation Example 39

To a mixture of 200 mg of N-(2-{5-hydroxy-2-methyl-1-[(4-methylphenyl)sulfonyl]-1H-indol-3-yl}ethyl)propanamide, 263 mg of triphenylphosphine, 95.0 mg of 2-(3-methyl-1H-pyrazol-1-yl)ethanol, and 2.10 mL of tetrahydrofuran was added dropwise a solution of 234 mg of bis(2-methoxyethyl) azodicarboxylate in 1.05 mL of tetrahydrofuran under ice-cooling. After the completion of dropwise addition, the mixture was warmed to room temperature and stirred overnight. The reaction mixture was diluted with ethyl acetate and washed with water, and then the organic layer was concentrated under reduced pressure. The obtained residue was purified by silica gel column chromatography (chloroform:methanol=98:2 to 93:7) to obtain 155 mg of N-(2-{2-methyl-1-[(4-methylphenyl)sulfonyl]-5-[2-(3-methyl-1H-pyrazol-1-yl)ethoxy]-1H-indol-3-yl}ethyl)propanamide.

Preparation Example 41

A mixture of 20.0 g of 1-methyl-1H-pyrazol-3-ol, 180 mL of 1,2-dibromoethane, 114 g of potassium carbonate, and 500 mL of acetonitrile was stirred at 50° C. for 5 hours. The reaction mixture was cooled to room temperature, the solid was separated by filtration, and then the filtrate was concentrated under reduced pressure. To the obtained residue was added water, followed by extraction with ethyl acetate. The organic layer was washed with a saturated aqueous sodium hydrogen carbonate solution and saturated aqueous sodium chloride solution, and dried over anhydrous sodium sulfate. The obtained organic layer was concentrated under reduced pressure to obtain 31.0 g of 3-(2-bromoethoxy)-1-methyl-1H-pyrazole as an oily substance.

Preparation Example 43

To a mixture of 8 mL of ethanol and 8 mL of water was added 1.38 g of N-[2-(5-{2-[(1-methyl-1H-pyrazol-3-yl)oxy]ethoxy}-1H-indol-3-yl)ethyl]acetamide, and 2.2 g of potassium hydroxide was added thereto, followed by stirring at 100° C. for 2 days. The reaction mixture was cooled to room temperature and then saturated aqueous sodium chloride solution was added thereto, followed by extraction with chloroform. The organic layer was concentrated under reduced pressure and then the obtained residue was purified by amino silica gel column chromatography (chloroform:methanol=99:1 to 93:7) to obtain 932 mg of 2-(5-{2-[(1-methyl-1H-pyrazol-3-yl)oxy]ethoxy}-1H-indol-3-yl)ethanamine as an oily substance.

In the same manner as the methods of Preparation Examples above, the compounds of Preparation Examples 40, 42, and 44 to 96 shown in Tables below were prepared.

The structures of the compounds of Preparation Examples are shown in Tables 6 to 24, and the physicochemical data and preparation methods of the compounds of Preparation Examples are shown in Tables 25 to 27.

Example 1

Under a nitrogen gas flow, an activated magnesium suspension (prepared by subjecting 50 mg of magnesium in 2.00 mL of methanol to an ultrasonic treatment) was added to a mixture of 590 mg of N-[2-(2-methyl-1-[(4-methylphenyl)sulfonyl]-5-{2-[(1-methyl-1H-pyrazol-3-yl)oxy]ethoxy}-1H-indol-3-yl)ethyl]propanamide, 160 mg of magnesium, and 20.0 mL of methanol, followed by stirring for 3 hours while cooling in a water bath under a nitrogen gas flow. To the reaction mixture was added 160 mg of magnesium, followed by further stirring for 3 hours, and 160 mg of magnesium was added thereto, followed by further stirring for 1 hour. To the reaction mixture was added a saturated aqueous ammonium chloride solution, followed by extraction with chloroform. The organic layer was concentrated under reduced pressure and then the obtained residue was purified by silica gel column chromatography (chloroform:methanol=98:2 to 92:8) to obtain 270 mg of N-[2-{2-methyl-5-(2-[(1-methyl-1H-pyrazol-3-yl)oxy]ethoxy}-1H-indol-3-yl)ethyl]propanamide as a solid.

Example 2

To 3.92 mL of acetonitrile were added 112 mg of N-{2-[5-(2-bromoethoxy)-1H-indol-3-yl]ethyl}acetamide, 67.6 mg of 1-methyl-1H-pyrazol-3-ol, and 393 mg of cesium carbonate, followed by stirring at 60° C. for 10 hours. The reaction mixture was cooled to room temperature, and water was added thereto, followed by extraction with ethyl acetate. The organic layer was concentrated under reduced pressure and the obtained residue was purified by silica gel column chromatography (chloroform:methanol=10:1) to obtain 100 mg of N-[2-(5-{2-[(1-methyl-1H-pyrazol-3-yl)oxy]ethoxy}-1H-indol-3-yl)ethyl]acetamide as an oily substance.

Example 3

A mixture of 200 mg of N-[2-(5-hydroxy-1H-indol-3-yl)ethyl]acetamide, 160 mg of 2-(pyrazin-2-yloxy)ethanol, 508 µL of cyanomethylene tributylphosphorane, and 4.00 mL of toluene was stirred at 90° C. for 1.5 hours and at 110° C. for 1.5 hours. The reaction mixture was cooled to room temperature and concentrated under reduced pressure, and the obtained residue was purified by silica gel column chromatography (chloroform:methanol=100:0 to 95:5), and further purified by amino silica gel column chromatography (chloroform:methanol=100:0 to 95:5) twice to obtain 250 mg of N-(2-{5-[2-(pyrazin-2-yloxy)ethoxy]-1H-indol-3-yl}ethyl)acetamide as a solid.

Example 4

To a mixture of 200 mg of N-[2-(5-hydroxy-1H-indol-3-yl)ethyl]acetamide, 261 mg of 2-[3-(trifluoromethyl)-1H-pyrazol-1-yl]ethanol, 361 mg of triphenylphosphine, and 2.00 mL of tetrahydrofuran was added dropwise 625 µL of diethyl azodicarboxylate (a 2.2 M toluene solution) under ice-cooling. After the completion of dropwise addition, the mixture was warmed to room temperature and stirred overnight. The reaction mixture was concentrated under reduced pressure and the obtained residue was purified by silica gel column chromatography (chloroform:methanol=100:0 to 10:1) to obtain 65.0 mg of N-[2-(5-{2-[3-(trifluoromethyl)-1H-pyrazol-1-yl]ethoxy}-1H-indol-3-yl)ethyl]acetamide as an oily substance.

Example 5

A mixture of 100 mg of N-(2-[5-(2-bromoethoxy)-1H-indol-3-yl]ethyl) acetamide, 77.0 mg of 5-hydroxy-2-methoxypyridine, 301 mg of cesium carbonate, and 3.00 mL of dimethylformamide was stirred at 70° C. for 48 hours. The reaction mixture was cooled to room temperature, and then water was added thereto, followed by extraction with chloroform. The organic layer was washed with saturated aqueous sodium chloride solution and concentrated under reduced pressure. The obtained residue was purified by silica gel column chromatography (chloroform:methanol=100:0 to 20:1) and further purified by silica gel column chromatography (hexane:ethyl acetate=100:0 to 50:50 to 0:100) to obtain 40.0 mg of N-[2-(5-{2-[(6-methoxypyridin-3-yl)oxy]ethoxy}-1H-indol-3-yl)ethyl]acetamide as an oily substance.

Example 6

In a mixture of 3.10 mL of methanol and 6.20 mL of tetrahydrofuran was dissolved 385 mg of N-[2-(6-fluoro-1-[(4-methylphenyl)sulfonyl]-5-{2-[(1-methyl-1H-pyrazol-3-yl)oxy]ethoxy}-1H-indol-3-yl)ethyl]acetamide, and 732 mg of cesium carbonate was added thereto, followed by heating to 65° C. and stirring for 3 hours. After cooling to room temperature, to the reaction mixture was added water, followed by extraction with chloroform. The organic layer was concentrated under reduced pressure and then the obtained residue was purified by silica gel column chromatography (chloroform:methanol=97:3 to 92:8) to obtain 191 mg of N-[2-(6-fluoro-5-{2-[(1-methyl-1H-pyrazol-3-yl)oxy]ethoxy}-1H-indol-3-yl)ethyl]acetamide as a solid.

Example 7

In 3.00 mL of tetrahydrofuran were dissolved 84.0 mg of 2-(2-methyl-5-{2-[(1-methyl-1H-pyrazol-3-yl)oxy]ethoxy}-1H-indol-3-yl)ethanamine and 112 µL of triethylamine, and to the reaction mixture was added 27.8 µL of acetic anhydride, followed by stirring at room temperature for 1.5 hours. To the reaction mixture was added methanol, followed by stirring, and then the reaction mixture was concentrated under reduced pressure. The obtained residue was purified by silica gel column chromatography (chloroform:methanol=99:1 to 95:5) to obtain 89.0 mg of N-[2-(2-methyl-5-{2-[(1-methyl-1H-pyrazol-3-yl)oxy]ethoxy}-1H-indol-3-yl)ethyl]acetamide.

Example 8

To a mixture 150 mg of 2-(5-{2-[(1-methyl-1H-pyrazol-3-yl)oxy]ethoxy}-1H-indol-3-yl)ethanamine, 200 µL of triethylamine, and 3.50 mL of dichloromethane was added 96.0 µL of propionic anhydride, followed by stirring at room temperature for 2 hours. To the reaction mixture was added water, followed by extraction with chloroform. The organic layer was concentrated under reduced pressure and then the obtained residue was purified by silica gel column chromatography (chloroform:methanol=97:3 to 92:8) to obtain 187 mg of N-[2-(5-{2-[(1-methyl-1H-pyrazol-3-yl)oxy]ethoxy}-1H-indol-3-yl)ethyl]propanamide.

Example 9

To a mixture of 34.0 mg of 2-(2-methyl-5-{2-[(2-methylpyridin-4-yl)oxy]ethoxy}-1H-indol-3-yl)ethanamine and 1.50 mL of tetrahydrofuran was added 23.0 mg of 1,1'-carbonyldiimidazole under ice-cooling, followed by warming to room temperature and stirring for 1 hour. To the reaction mixture was added 56.9 µL of methylamine (a 9.8

M methanol solution), followed by stirring at room temperature overnight. To the reaction mixture was added water, followed by extraction with chloroform, and the organic layer was concentrated under reduced pressure. The obtained residue was purified by silica gel column chromatography (chloroform:methanol=97:3 to 92:8) to obtain 26.0 mg of 1-methyl-3-[2-(2-methyl-5-{2-[(2-methylpyridin-4-yl)oxy]ethoxy}-1H-indol-3-yl)ethyl]urea as a solid.

Example 10

A mixture of 89.0 mg of 2-(2-methyl-5-{2-[(1-methyl-1H-pyrazol-3-yl)oxy]ethoxy}-1H-indol-3-yl)ethanamine, 61.1 mg of 4-nitrophenylmethylcarbamate, 50.0 µL of triethylamine, and 2.00 mL of tetrahydrofuran was stirred at 60° C. for 3 hours. To the reaction mixture was added methanol, followed by stirring, and then the reaction mixture was concentrated under reduced pressure. The obtained residue was purified by silica gel column chromatography (chloroform:methanol=99:1 to 95:5), and further purified by amino silica gel column chromatography (chloroform:methanol=99:1 to 95:5) to obtain 87.0 mg of 1-methyl-3-[2-(2-methyl-5-{2-[(1-methyl-1H-pyrazol-3-yl)oxy]ethoxy}-1H-indol-3-yl)ethyl]urea as a solid.

Example 11

A mixture of 200 mg of 2-{[3-(2-acetamidoethyl)-1H-indol-5-yl]oxy}ethyl 4-methylbenzenesulfonate, 110 mg of 6-methylpyridin-2-ol, 200 mg of potassium carbonate, and 4.00 mL of dimethylformamide was stirred at 60° C. for 18 hours. After cooling to room temperature, to the reaction mixture were added chloroform and water, followed by extraction with chloroform, and then the organic layer was concentrated under reduced pressure. The obtained residue was purified by silica gel column chromatography (chloroform:methanol=100:0 to 95:5). The obtained compound was purified by preparative thin layer chromatography (chloroform:methanol=10:1) to obtain 86.0 mg of N-[2-(5-{2-[(6-methylpyridin-2-yl)oxy]ethoxy}-1H-indol-3-yl)ethyl]acetamide.

In the same manner as the methods of Examples above, the compounds of Examples 12 to 64 shown in Tables below were prepared.

Example 65

In a mixture of 150 mL of methanol and 300 mL of tetrahydrofuran, 19.0 g of N-[2-(6-fluoro-1-[(4-methylphenyl)sulfonyl]-5-{2-[(1-methyl-1H-pyrazol-3-yl)oxy]ethoxy}-1H-indol-3-yl)ethyl]acetamide was dissolved, followed by adding 37.0 g of cesium carbonate, heating to 65° C., and stirring for 4 hours. The reaction mixture was cooled to room temperature and ethyl acetate was added thereto, followed by washing with a saturated aqueous sodium hydrogen carbonate solution and saturated aqueous sodium chloride solution. The organic layer was dried over magnesium sulfate, the solid was separated by filtration, and the filtrate was concentrated under the reduced pressure. The obtained residue was purified by silica gel column chromatography (chloroform:methanol=97:3 to 92:8). The resultant was suspended and stirred in 30 mL of diisopropylether and 90 mL of ethyl acetate. The obtained solid was collected by filtration to obtain 10.4 g of N-[2-(6-fluoro-5-{2-[(1-methyl-1H-pyrazol-3-yl)oxy]ethoxy}-1H-indol-3-yl)ethyl]acetamide as white crystals.

The crystals obtained in this Example have peaks at around 5.0, 9.9, 10.1, 17.0, 17.7, 18.1, 18.6, 19.8, 21.5, and 24.8 of diffraction angles 2θ (°) in powder X-ray diffraction.

Example 66

In 1.00 mL of 2-propanol, 100 mg of N-[2-(2-methyl-5-{2-[(1-methyl-1H-pyrazol-3-yl)oxy]ethoxy}-1H-indol-3-yl)ethyl]propanamide was suspended, heated to reflux for 10 minutes, cooled to room temperature, and stirred overnight. The precipitated solid was collected by filtration and dried under the reduced pressure at 45° C. overnight to obtain 43.0 mg of N-[2-(2-methyl-5-{2-[(1-methyl-1H-pyrazol-3-yl)oxy]ethoxy}) H-indol-3-yl)ethyl]propanamide as white crystals.

The crystals obtained in this Example have peaks at around 8.1, 8.5, 10.8, 12.5, 15.4, 16.3, 17.0, 17.8, 21.1, and 21.8 of diffraction angles 2θ (°) in powder X-ray diffraction.

The structures of the compounds of Examples are shown in Tables 28 to 41, and the physicochemical data and preparation methods of the compounds of Examples are shown in Tables 42 to 47.

TABLE 6

| PEx | Str |
|---|---|
| 1 | |
| 2 | |
| 3 | |
| 4 | 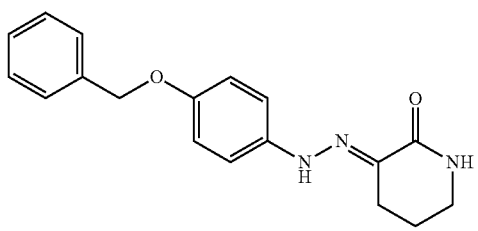 |

TABLE 6-continued

| PEx | Str |
|---|---|
| 5 | (structure) |

TABLE 7

| PEx | Str |
|---|---|
| 6 | (structure) |
| 7 | (structure) |
| 8 | (structure) |
| 9 | (structure) |
| 10 | (structure) |
| 11 | (structure) |
| 12 | (structure) |

TABLE 8

| PEx | Str |
|---|---|
| 13 | (structure) |
| 14 | (structure) |
| 15 | (structure) |
| 16 | (structure) |
| 17 | (structure) |

TABLE 9

| PEx | Str |
|---|---|
| 18 | (structure) |

TABLE 9-continued
| PEx | Str |
|---|---|
| 19 | 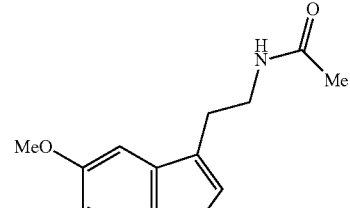 |
| 20 | 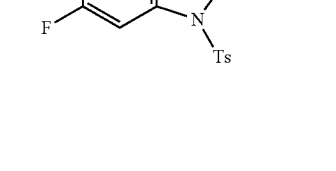 |
| 21 | 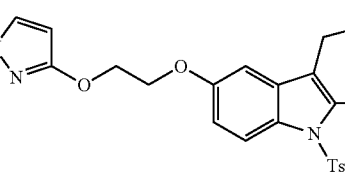 |
| 22 |  |
| 23 | 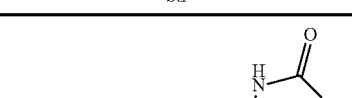 |
TABLE 10
| PEx | Str |
|---|---|
| 24 | |
TABLE 10-continued
| PEx | Str |
|---|---|
| 25 | |
| 26 | |
| 27 | |
| 28 | |
TABLE 11
| PEx | Str |
|---|---|
| 29 | |

TABLE 11-continued
| PEx | Str |
|---|---|
| 30 | 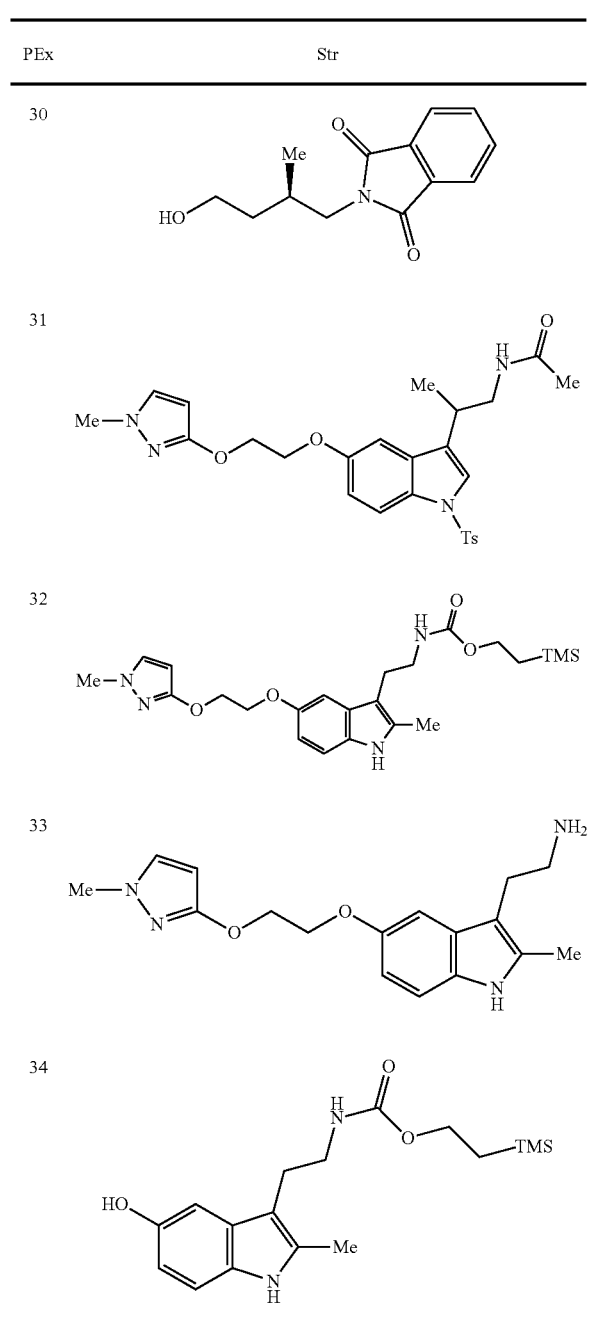 |
| 31 | |
| 32 | |
| 33 | |
| 34 | |
TABLE 12
| PEx | Str |
|---|---|
| 35 |  |
| 36 | 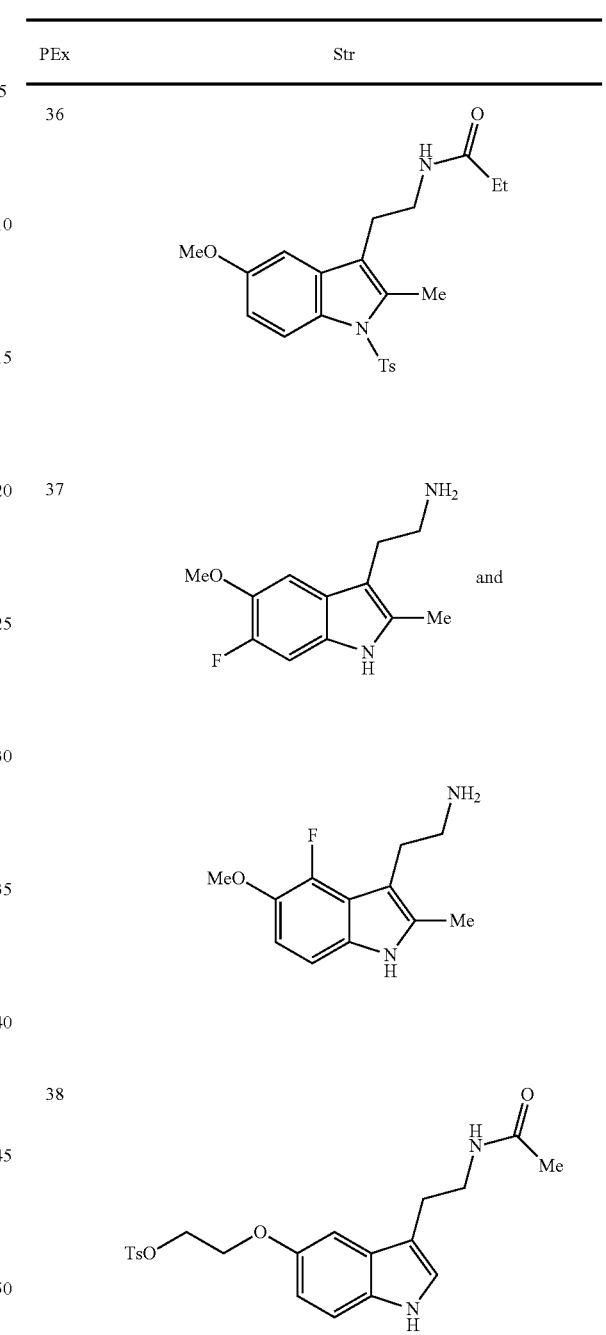 |
| 37 | |
| 38 | |
| 39 | |
and TABLE 13
| PEx | Str |
|---|---|
| 40 | 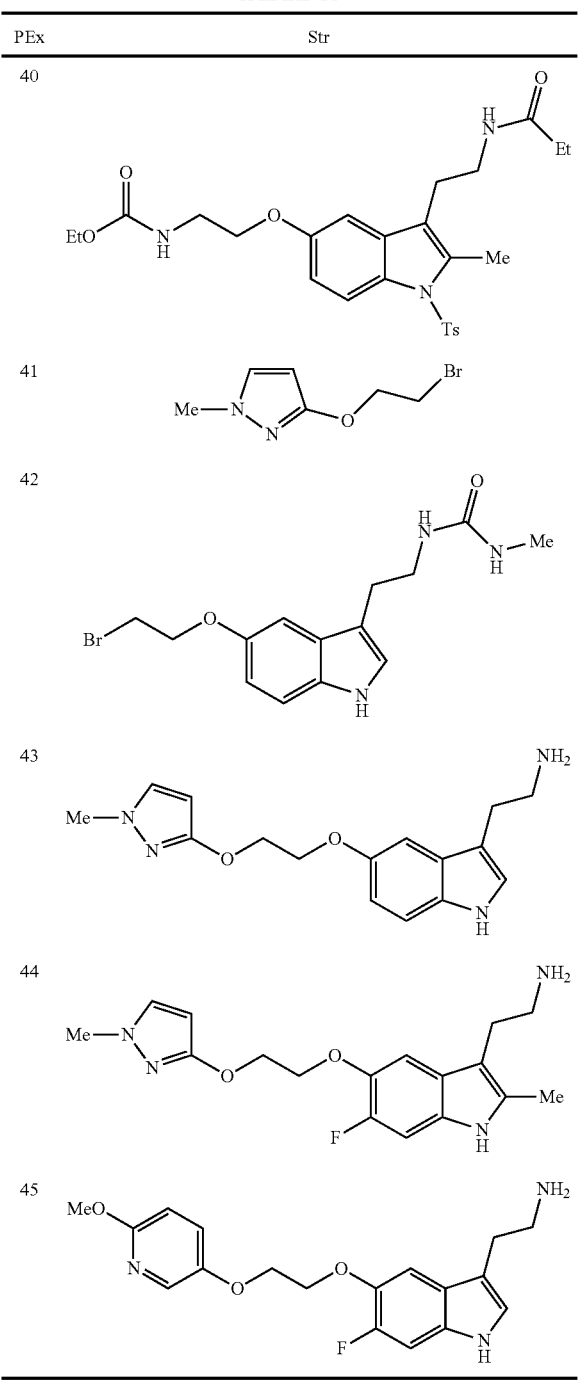 |
| 41 | |
| 42 | |
| 43 | |
| 44 | |
| 45 | |
TABLE 14
| PEx | Str |
|---|---|
| 46 | |
TABLE 14-continued
| PEx | Str |
|---|---|
| 47 | 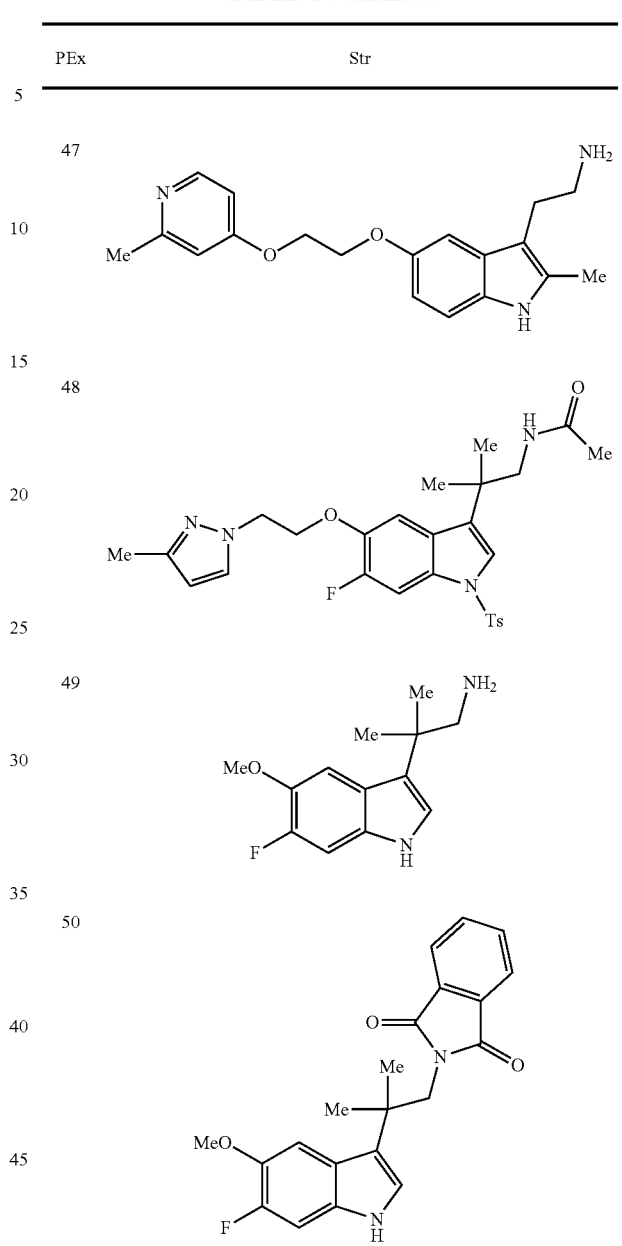 |
| 48 | |
| 49 | |
| 50 | |
TABLE 15
| PEx | Str |
|---|---|
| 51 | |

TABLE 15-continued

| PEx | Str |
|---|---|
| 52 | *N-(2-(6-fluoro-5-hydroxy-1-tosyl-1H-indol-3-yl)ethyl)acetamide* |
| 53 | *1-(2-(6-fluoro-5-hydroxy-1-tosyl-1H-indol-3-yl)ethyl)-3-methylurea* |
| 54 | *N-(2-(5-hydroxy-2-methyl-1-tosyl-1H-indol-3-yl)ethyl)acetamide* |
| 55 | *1-(2-(5-hydroxy-2-methyl-1-tosyl-1H-indol-3-yl)ethyl)-3-methylurea* |

TABLE 16

| PEx | Str |
|---|---|
| 56 | *N-(2-(6-fluoro-5-hydroxy-2-methyl-1-tosyl-1H-indol-3-yl)ethyl)acetamide* |

TABLE 16-continued

| PEx | Str |
|---|---|
| 57 | *N-(2-(5-hydroxy-1-tosyl-1H-indol-3-yl)propyl)acetamide* |
| 58 | *N-(2-(6-fluoro-5-hydroxy-1-tosyl-1H-indol-3-yl)-2-methylpropyl)acetamide* |
| 59 | *(R)-N-(2-(6-chloro-5-hydroxy-1-tosyl-1H-indol-3-yl)propyl)acetamide* |
| 60 | *(R)-N-(2-(6-fluoro-5-hydroxy-1-tosyl-1H-indol-3-yl)propyl)acetamide* |

TABLE 17

| PEx | Str |
|---|---|
| 61 | *N-(2-(6-fluoro-2-methyl-5-(2-(3-methyl-1H-pyrazol-1-yl)ethoxy)-1-tosyl-1H-indol-3-yl)ethyl)acetamide* |

TABLE 17-continued

| PEx | Str |
|---|---|
| 62 | (5-methoxy-6-fluoro-1-tosyl-1H-indol-3-yl)ethyl-N'-methylurea |
| 63 | N-[2-(5-methoxy-2-methyl-1-tosyl-1H-indol-3-yl)ethyl]acetamide |
| 64 | 1-[2-(5-methoxy-2-methyl-1-tosyl-1H-indol-3-yl)ethyl]-3-methylurea |
| 65 | N-[(2R)-2-(5-methoxy-1-tosyl-1H-indol-3-yl)propyl]acetamide |

TABLE 18

| PEx | Str |
|---|---|
| 66 | N-[2-(5-methoxy-6-fluoro-1-tosyl-1H-indol-3-yl)-2-methylpropyl]acetamide |

TABLE 18-continued

| PEx | Str |
|---|---|
| 67 | N-[(2R)-2-(5-methoxy-6-chloro-1-tosyl-1H-indol-3-yl)propyl]acetamide |
| 68 | N-[(2R)-2-(5-methoxy-6-fluoro-1-tosyl-1H-indol-3-yl)propyl]acetamide |
| 69 | N-{2-[5-(2-((1-methyl-1H-pyrazol-3-yl)oxy)ethoxy)-6-fluoro-1-tosyl-1H-indol-3-yl]ethyl}acetamide |
| 70 | 1-{2-[5-(2-((6-methoxypyridin-3-yl)oxy)ethoxy)-2-methyl-1-tosyl-1H-indol-3-yl]ethyl}-3-methylurea |

TABLE 19

| PEx | Str |
|---|---|
| 71 | N-{2-[5-(2-((6-methoxypyridin-3-yl)oxy)ethoxy)-6-fluoro-2-methyl-1-tosyl-1H-indol-3-yl]ethyl}acetamide |

TABLE 19-continued
| PEx | Str |
|---|---|
| 72 | 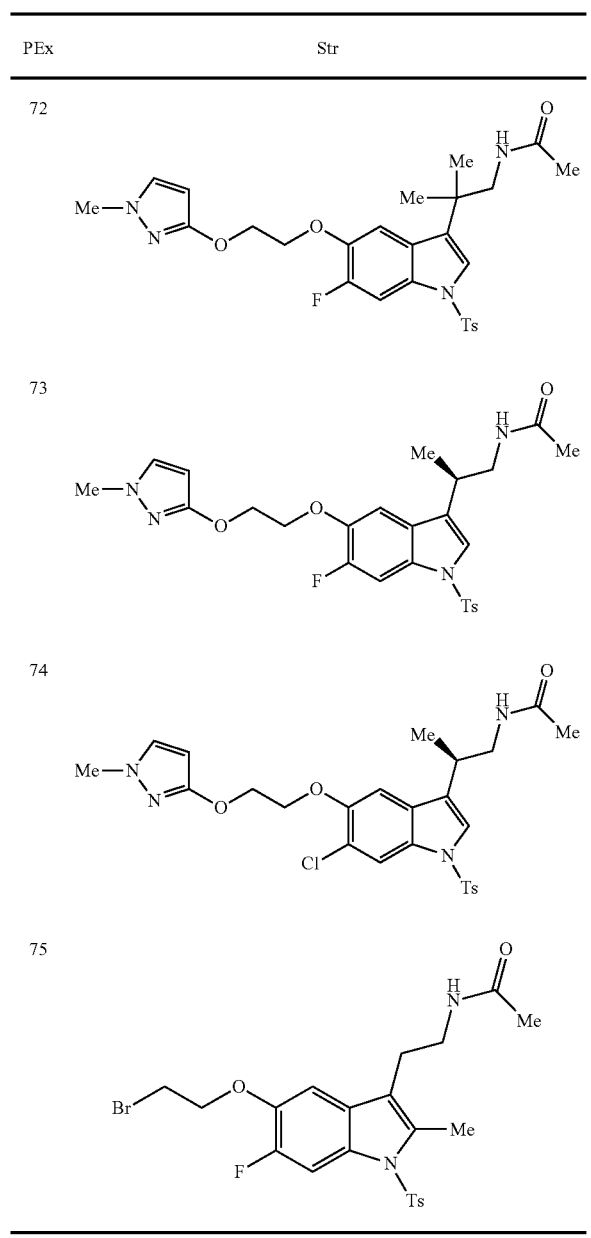 |
| 73 | |
| 74 | |
| 75 | |
TABLE 20
| PEx | Str |
|---|---|
| 76 | 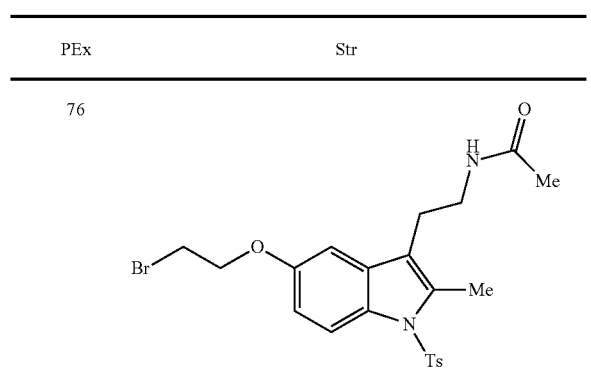 |
TABLE 20-continued
| PEx | Str |
|---|---|
| 77 | 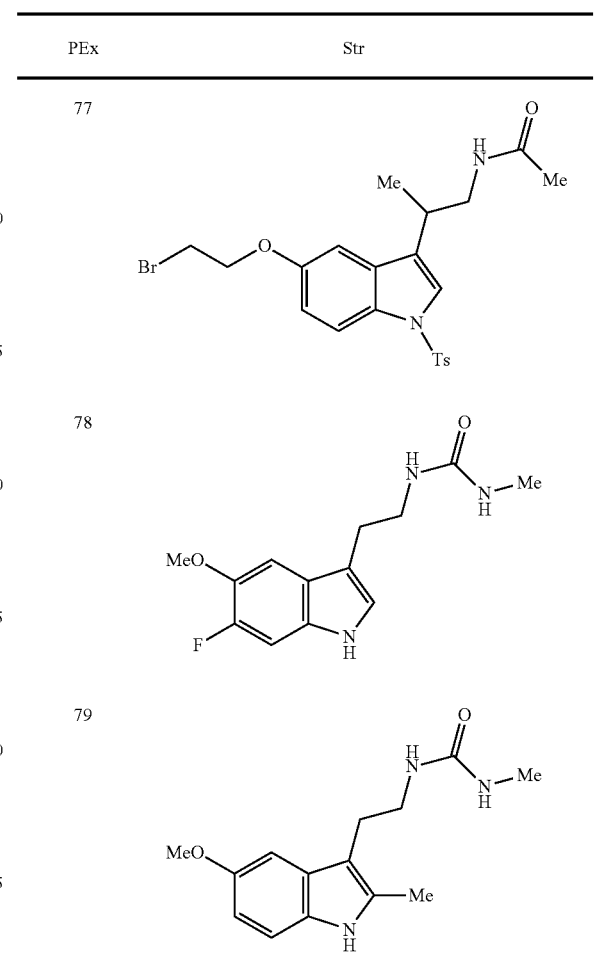 |
| 78 | |
| 79 | |
TABLE 21
| PEx | Str |
|---|---|
| 80 | 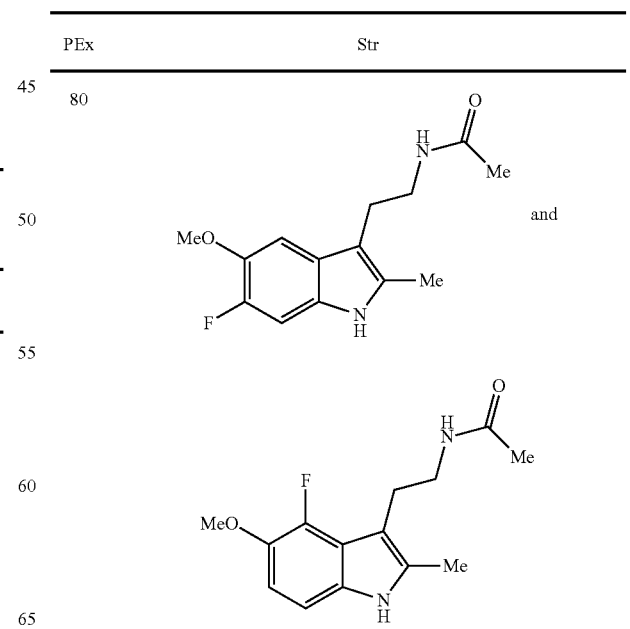 |
and TABLE 21-continued
| PEx | Str |
|---|---|
| 81 | 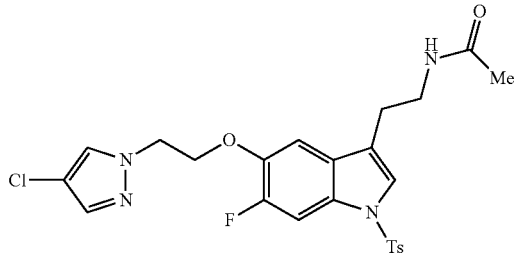 [SMILES: CC(=O)NCCc1cn(S(=O)(=O)c2ccc(C)cc2)c2cc(F)c(OCCn3cc(Cl)cn3)cc12] |
| 82 | 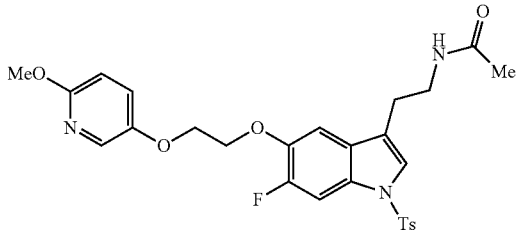 [SMILES: COc1ccc(OCCOc2cc3c(CCNC(C)=O)cn(S(=O)(=O)c4ccc(C)cc4)c3cc2F)cn1] |
| 83 | 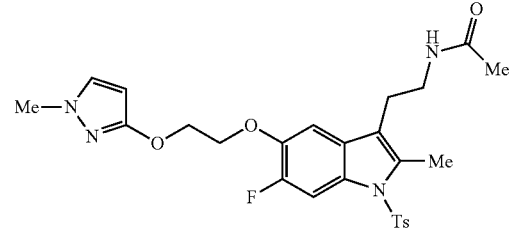 [SMILES: CC(=O)NCCc1c(C)n(S(=O)(=O)c2ccc(C)cc2)c2cc(F)c(OCCOc3ccn(C)n3)cc12] |
TABLE 22
| PEx | Str |
|---|---|
| 84 | 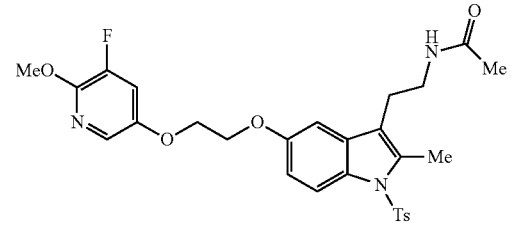 [SMILES: COc1ncc(OCCOc2ccc3c(c2)c(CCNC(C)=O)c(C)n3S(=O)(=O)c2ccc(C)cc2)cc1F] |
| 85 | 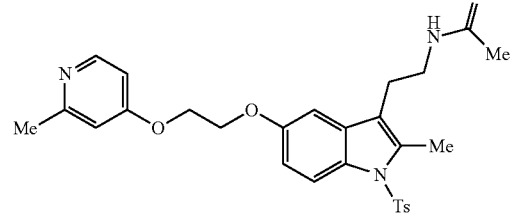 |
TABLE 22-continued
| PEx | Str |
|---|---|
| 86 | 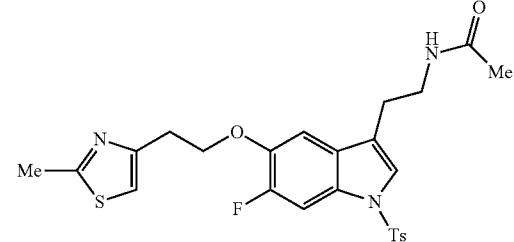 [SMILES: CC(=O)NCCc1cn(S(=O)(=O)c2ccc(C)cc2)c2cc(F)c(OCCc3csc(C)n3)cc12] |
| 87 | 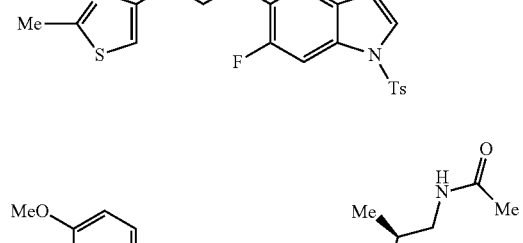 |
| 88 | 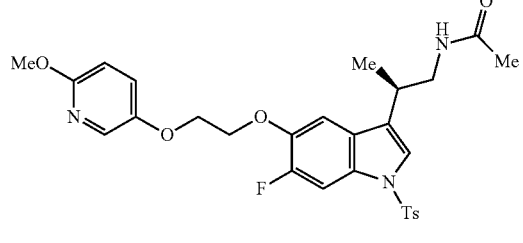 |
TABLE 23
| PEx | Str |
|---|---|
| 89 | 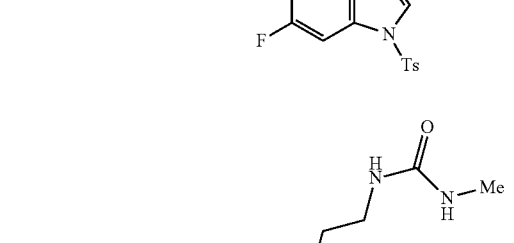 |
| 90 | 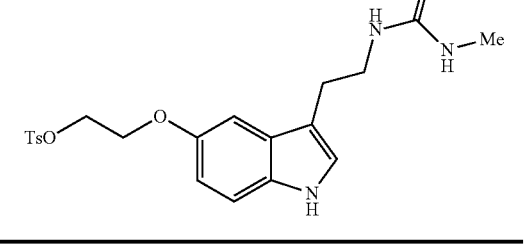 |

TABLE 23-continued

| PEx | Str |
|---|---|
| 91 | (structure) |
| 92 | (structure) |
| 93 | (structure) |

TABLE 24

| PEx | Str |
|---|---|
| 94 | (structure) |
| 95 | (structure) |

TABLE 24-continued

| PEx | Str |
|---|---|
| 96 | 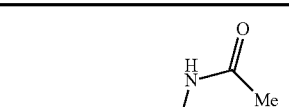 |

TABLE 25

| PEx | Psyn | DAT |
|---|---|---|
| 1 | PEx1 | ESI+: 221 |
| 2 | PEx2 | ESI+: 232, 234 |
| 3 | PEx3 | ESI+: 325, 327 |
| 4 | PEx4 | APCI/ESI+: 310 |
| 5 | PEx5 | APCI/ESI+: 293 |
| 6 | PEx6 | ESI+: 311 |
| 7 | PEx7 | ESI−: 409 |
| 8 | PEx8 | ESI+: 424 |
| 9 | PEx9 | ESI+: 324 |
| 10 | PEx10 | ESI+: 141 |
| 11 | PEx11 | ESI+: 477 [M + Na]+ |
| 12 | PEx12 | ESI+: 143 |
| 13 | PEx13 | ESI+: 560 |
| 14 | PEx14 | ESI+: 513 |
| 15 | PEx15 | ESI+: 223 |
| 16 | PEx16 | ESI+: 234 |
| 17 | PEx17 | ESI+: 353 |
| 18 | PEx18 | ESI+: 232 |
| 19 | PEx19 | ESI+: 472 |
| 20 | PEx20 | ESI+: 265 |
| 21 | PEx21 | ESI+: 401 |
| 22 | PEx22 | ESI+: 319 |
| 23 | PEx23 | ESI+: 542 |
| 24 | PEx24 | ESI+: 502 |
| 25 | PEx25 | ESI+: 405 |
| 26 | PEx26 | ESI+: 525 |
| 27 | PEx27 | ESI+: 497, 499 |
| 28 | PEx28 | APCI/ESI+: 324 |
| 29 | PEx29 | ESI+: 261 |
| 30 | PEx30 | ESI+: 234 |
| 31 | PEx31 | APCI/ESI+: 511 |
| 32 | PEx32 | ESI+: 459 |
| 33 | PEx33 | ESI+: 315 |

TABLE 26

| PEx | Psyn | DAT |
|---|---|---|
| 34 | PEx34 | ESI+: 357 [M + Na]+ |
| 35 | PEx35 | ESI+: 463 [M + Na]+ |
| 36 | PEx36 | ESI+: 415 |
| 37 | PEx37 | ESI+: 223 |
| 38 | PEx38 | ESI+: 417 |
| 39 | PEx39 | ESI+: 509 |
| 40 | PEx24 | ESI+: 516 |
| 41 | PEx41 | ESI+: 205, 207 |
| 42 | PEx3 | ESI+: 340, 342 |
| 43 | PEx43 | ESI+: 301 |
| 44 | PEx43 | ESI+: 333 |
| 45 | PEx43 | ESI+: 346 |
| 46 | PEx43 | ESI+: 360 |
| 47 | PEx43 | ESI+: 326 |
| 48 | PEx14 | ESI+: 527 |
| 49 | PEx15 | ESI+: 237 |
| 50 | PEx17 | ESI+: 367 |

TABLE 26-continued

| PEx | Psyn | DAT |
|---|---|---|
| 51 | PEx20 | ESI+: 279 |
| 52 | PEx21 | ESI+: 391 |
| 53 | PEx21 | ESI+: 406 |
| 54 | PEx21 | ESI+: 387 |
| 55 | PEx21 | ESI+: 402 |
| 56 | PEx21 | ESI+: 405 |
| 57 | PEx21 | APCI/ESI+: 387 |
| 58 | PEx21 | ESI+: 419 |
| 59 | PEx21 | ESI+: 421 |
| 60 | PEx21 | ESI+: 405 |
| 61 | PEx39 | ESI+: 513 |
| 62 | PEx25 | ESI+: 420 |
| 63 | PEx25 | ESI+: 401 |
| 64 | PEx36 | ESI+: 416 |
| 65 | PEx25 | APCI/ESI+: 401 |
| 66 | PEx25 | ESI+: 433 |
| 67 | PEx25 | ESI+: 435 |

TABLE 27

| PEx | Psyn | DAT |
|---|---|---|
| 68 | PEx25 | ESI+: 419 |
| 69 | PEx26 | ESI+: 515 |
| 70 | PEx26 | ESI+: 553 |
| 71 | PEx26 | ESI+: 556 |
| 72 | PEx26 | ESI+: 543 |
| 73 | PEx26 | ESI+: 529 |
| 74 | PEx26 | ESI+: 545, 547 |
| 75 | PEx27 | ESI+: 511, 513 |
| 76 | PEx3 | ESI+: 493, 495 |
| 77 | PEx3 | APCI/ESI+: 493, 495 |
| 78 | PEx28 | ESI+: 266 |
| 79 | PEx28 | ESI+: 262 |
| 80 | PEx29 | ESI+: 265 |
| 81 | PEx31 | ESI+: 519, 521 |
| 82 | PEx31 | ESI+: 542 |
| 83 | PEx31 | ESI+: 529 |
| 84 | PEx31 | ESI+: 556 |
| 85 | PEx31 | ESI+: 522 |
| 86 | PEx39 | ESI+: 516 |
| 87 | PEx32 | ESI+: 556 |
| 88 | PEx38 | ESI+: 432 |
| 89 | PEx38 | APCI/ESI+: 571 |
| 90 | PEx39 | ESI+: 531 |
| 91 | PEx39 | ESI+: 513 |
| 92 | PEx24 | ESI+: 495 |
| 93 | PEx24 | ESI+: 510 |
| 94 | PEx24 | ESI+: 488 |
| 95 | PEx24 | ESI+: 506 |
| 96 | PEx36 | ESI+: 419 |

TABLE 28

| Ex. | Str |
|---|---|
| 1 | 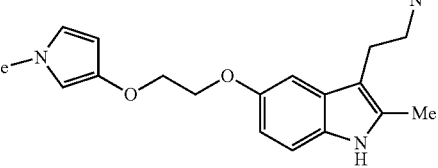 |
| 2 |  |
| 3 | 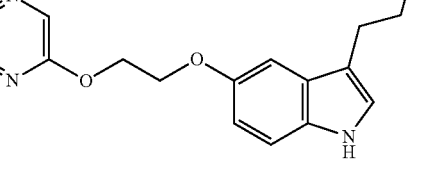 |
| 4 | 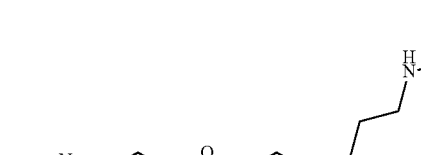 |
| 5 |  |

TABLE 29

| Ex. | Str |
|---|---|
| 6 |  |
| 7 | |

TABLE 29-continued
| Ex. | Str |
|---|---|
| 8 | 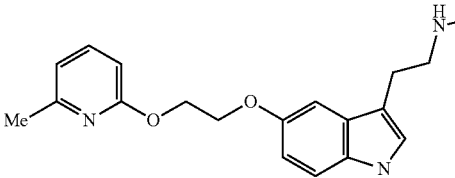 |
| 9 | |
| 10 | |
TABLE 30
| Ex. | Str |
|---|---|
| 11 | 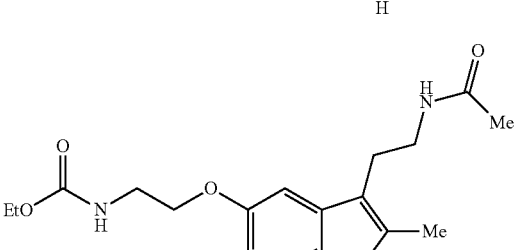 |
| 12 | |
| 13 | |
TABLE 30-continued
| Ex. | Str |
|---|---|
| 14 | 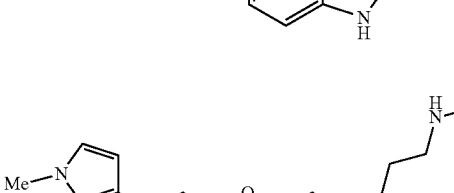 |
| 15 | |
TABLE 31
| Ex. | Str |
|---|---|
| 16 | 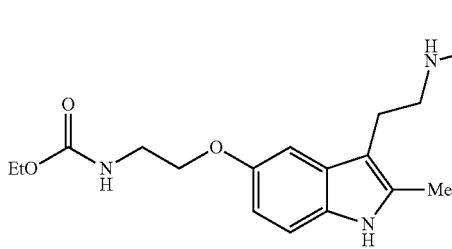 |
| 17 | |
| 18 | |

TABLE 31-continued
| Ex. | Str |
|---|---|
| 19 | 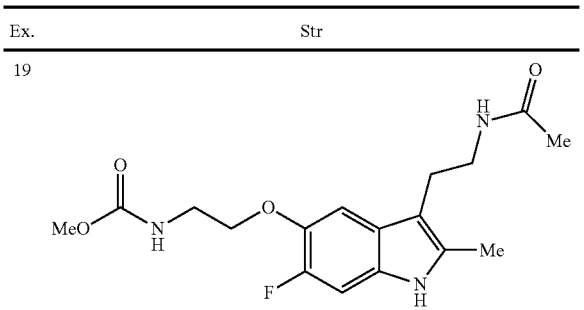 |
| 20 | 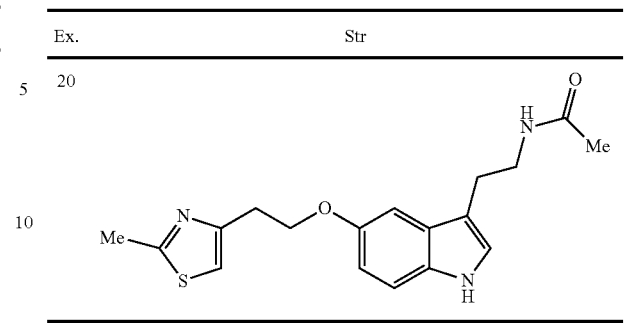 |
TABLE 32
| Ex. | Str |
|---|---|
| 21 | 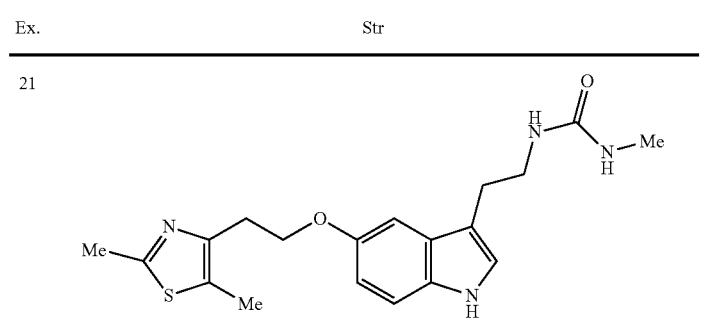 |
| 22 | 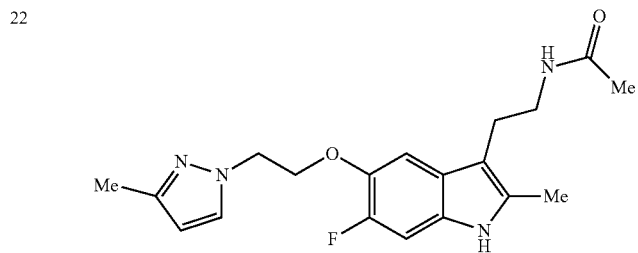 |
| 23 | 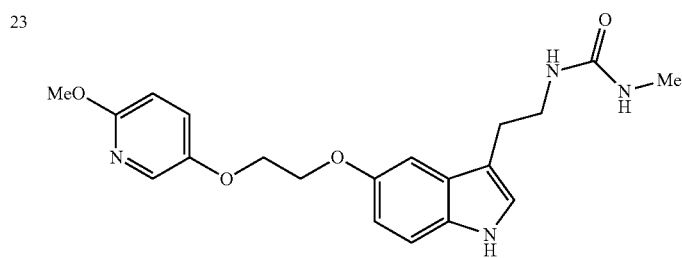 |
| 24 | 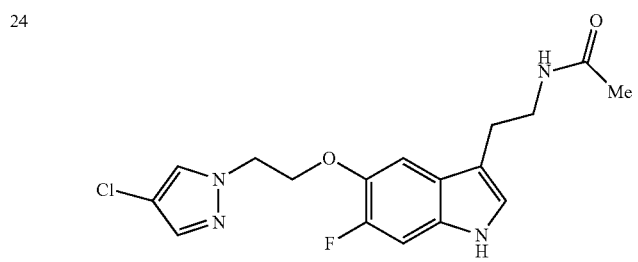 |

TABLE 32-continued
| Ex. | Str |
|---|---|
| 25 | 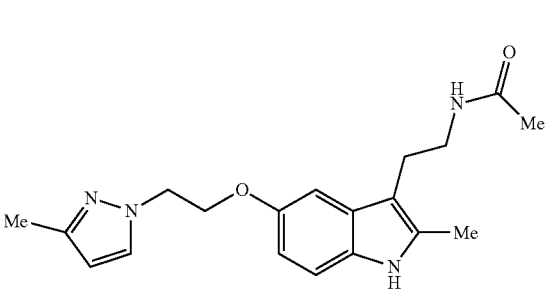 [SMILES: CC(=O)NCCc1c(C)[nH]c2ccc(OCCn3ccc(C)n3)cc12] |
TABLE 33
| Ex. | Str |
|---|---|
| 26 | 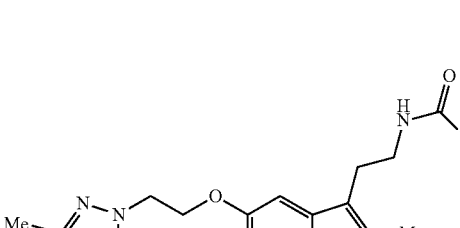 |
| 27 | |
| 28 | |
TABLE 33-continued
| Ex. | Str |
|---|---|
| 29 | |
| 30 | |
TABLE 34
| Ex. | Str |
|---|---|
| 31 | 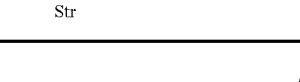 |

TABLE 34-continued
| Ex. | Str |
|---|---|
| 32 | 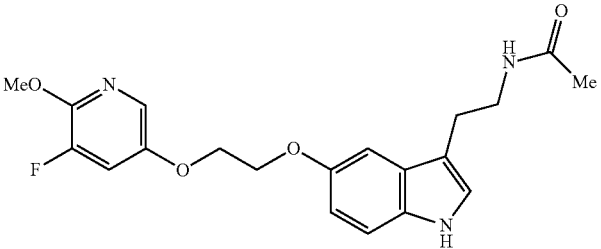 [SMILES: COc1ncc(OCCOc2ccc3[nH]cc(CCNC(C)=O)c3c2)cc1F] |
| 33 | 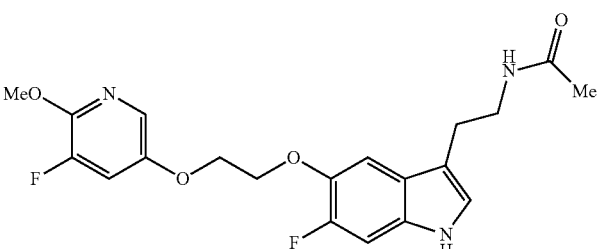 |
| 34 | 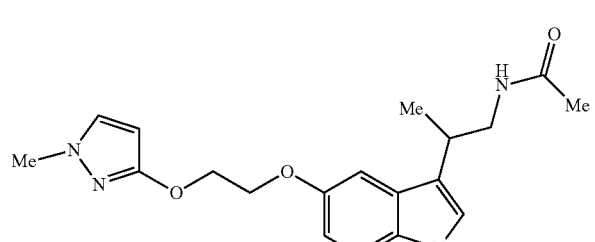 |
| 35 | 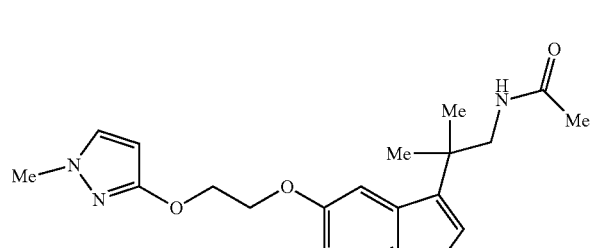 |
TABLE 35
| Ex. | Str |
|---|---|
| 36 | 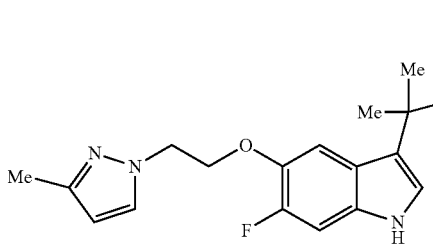 |
TABLE 35-continued
| Ex. | Str |
|---|---|
| 37 | 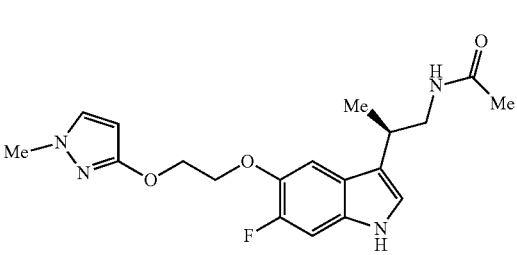 [SMILES: CC(=O)NC[C@H](C)c1c[nH]c2cc(F)c(OCCOc3ccn(C)n3)cc12] |

TABLE 35-continued
| Ex. | Str |
|---|---|
| 38 | 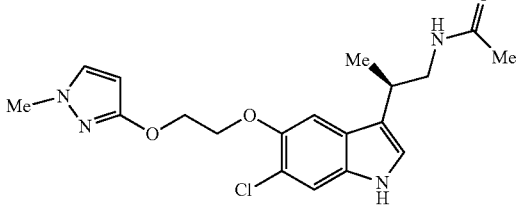 |
| 39 | 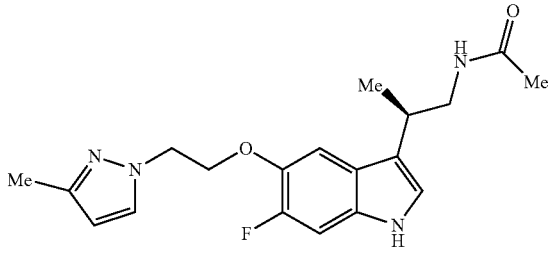 [SMILES: CC(=O)NC[C@H](C)c1c[nH]c2cc(F)c(OCCn3ccc(C)n3)cc12] |
| 40 | 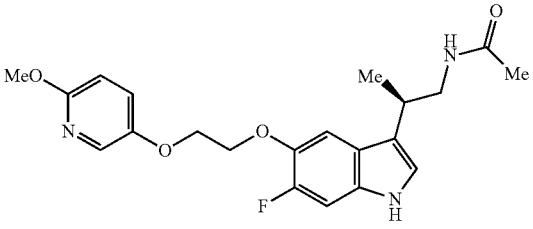 [SMILES: COc1ccc(OCCOc2cc3c([C@@H](C)CNC(C)=O)c[nH]c3cc2F)cn1] |
TABLE 36
| Ex. | Str |
|---|---|
| 41 | 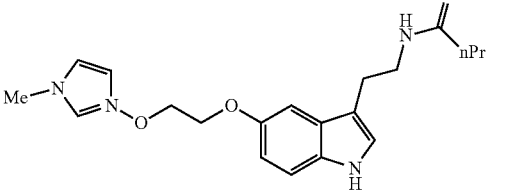 |
TABLE 36-continued
| Ex. | Str |
|---|---|
| 42 | 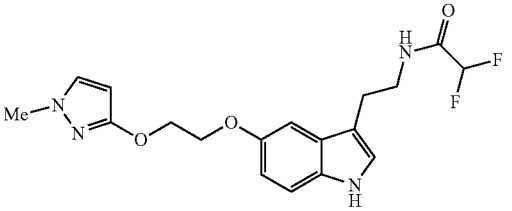 [SMILES: Cn1ccc(OCCOc2ccc3[nH]cc(CCNC(=O)C(F)F)c3c2)n1] |
| 43 | 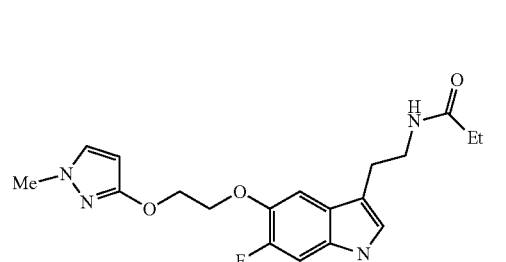 |
| 44 | 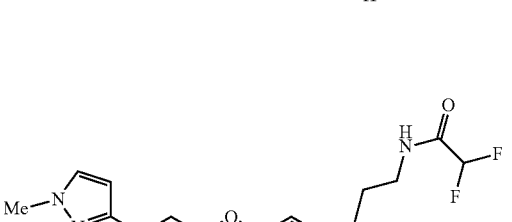 |
| 45 | 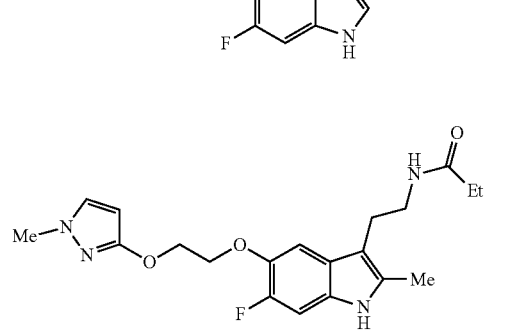 |
TABLE 37
| Ex. | Str |
|---|---|
| 46 | 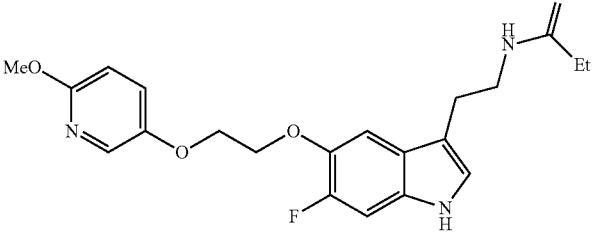 |

TABLE 37-continued

| Ex. | Str |
|---|---|
| 47 | 1-(2-{2-[(1-methyl-1H-pyrazol-3-yl)oxy]ethoxy}-6-fluoro-2-methyl-1H-indol-3-yl)ethyl-3-methylurea structure |
| 48 | 1-{2-[5-({2-[(5-fluoro-6-methoxypyridin-3-yl)oxy]ethoxy})-2-methyl-1H-indol-3-yl]ethyl}-3-methylurea structure |
| 49 | N-{2-[5-(2-{(5-bromopyridin-3-yl)oxy}ethoxy)-1H-indol-3-yl]ethyl}acetamide structure |
| 50 | 1-{2-[5-(2-{(5-bromopyridin-3-yl)oxy}ethoxy)-1H-indol-3-yl]ethyl}-3-methylurea structure |

TABLE 38

| Ex. | Str |
|---|---|
| 51 | N-{2-[5-(2-{(2-chloropyridin-4-yl)oxy}ethoxy)-1H-indol-3-yl]ethyl}acetamide structure |

TABLE 38-continued
| Ex. | Str |
|---|---|
| 52 | 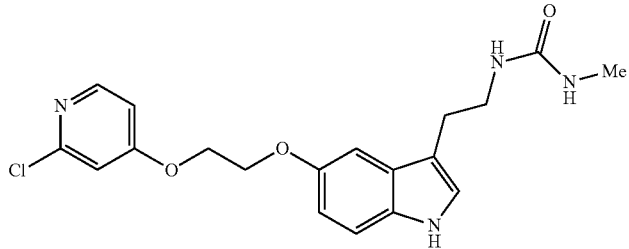 [SMILES: CNC(=O)NCCc1c[nH]c2ccc(OCCOc3ccnc(Cl)c3)cc12] |
| 53 | 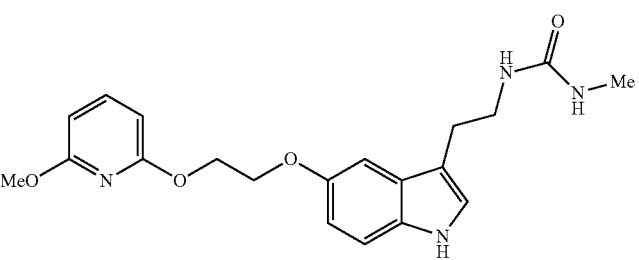 [SMILES: CNC(=O)NCCc1c[nH]c2ccc(OCCOc3cccc(OC)n3)cc12] |
| 54 | 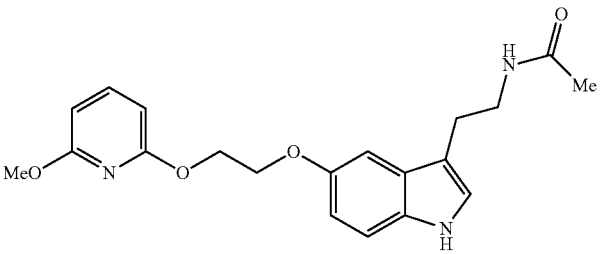 [SMILES: COc1cccc(OCCOc2ccc3[nH]cc(CCNC(C)=O)c3c2)n1] |
| 55 | 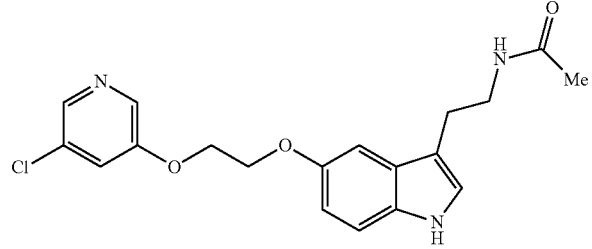 [SMILES: CC(=O)NCCc1c[nH]c2ccc(OCCOc3cncc(Cl)c3)cc12] |
TABLE 39
| Ex. | Str |
|---|---|
| 56 | 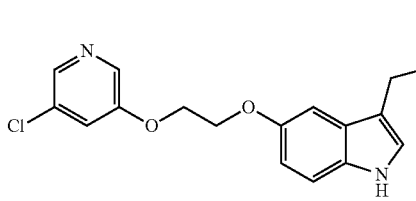 |
| 57 | 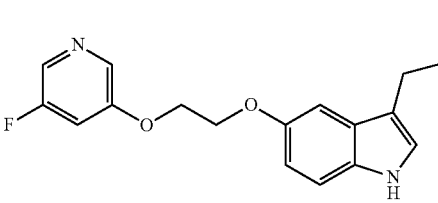 |

TABLE 39-continued

| Ex. | Str |
|---|---|
| 58 | 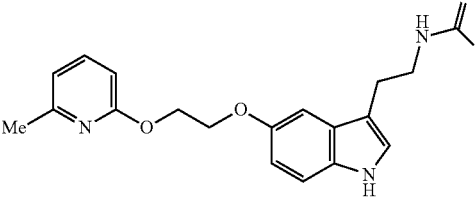 |
| 59 | |
| 60 | |

TABLE 40

| Ex. | Str |
|---|---|
| 61 | 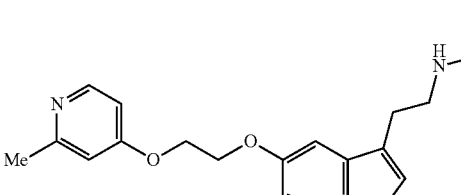 |
| 62 | |
| 63 | |

TABLE 40-continued

| Ex. | Str |
|---|---|
| 64 | 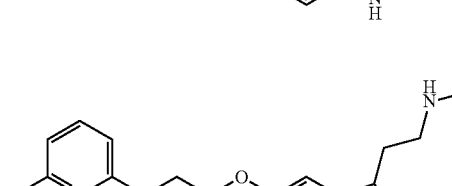 |

TABLE 41

| Ex. | Str |
|---|---|
| 65 | 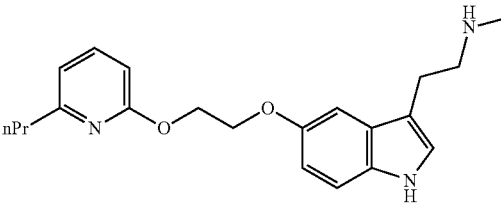 |
| 66 | |

TABLE 42

| Ex. | Syn | DAT |
|---|---|---|
| 1 | Ex1 | ESI+: 371<br>1H-NMR (DMSO-d6) δ:<br>0.97 (3H, t, J = 7.6 Hz), 2.04 (2H, q, J = 7.6 Hz), 2.27 (3H, s), 2.70 (2H, t, J = 7.1 Hz), 3.11-3.21 (2H, m), 3.67 (3H, s), 4.15-4.42 (4H, m), 5.65 (1H, d, J = 2.3 Hz), 6.64 (1H, dd, J = 8.6, 2.4 Hz), 6.96 (1H, d, J = 2.4 Hz), 7.11 (1H, d, J = 8.7 Hz), 7.47 (1H, d, J = 2.2 Hz), 7.72-7.84 (1H, m), 10.49-10.57 (1H, br) |
| 2 | Ex2 | ESI+: 343 |
| 3 | Ex3 | ESI+: 341 |
| 4 | Ex4 | ESI+: 381<br>1H-NMR (DMSO-d6) δ:<br>1.79 (3H, s), 2.75 (2H, t, J = 7.4 Hz), 3.22-3.34 (2H, m), 4.36 (2H, t, J = 5.2 Hz), 4.60 (2H, t, J = 5.2 Hz), 6.67 (1H, dd, J = 8.7, 2.4 Hz), 6.73 (1H, d, J = 2.4 Hz), 7.02 (1H, d, J = 2.4 Hz), 7.10 (1H, d, J = 2.3 Hz), 7.20 (1H, d, J = 8.7 Hz), 7.84-7.95 (1H, m), 8.03-8.08 (1H, m), 10.61-10.68 (1H, m) |
| 5 | Ex5 | ESI+: 370<br>1H-NMR (CDCl3) δ:<br>1.93 (3H, s), 2.93 (2H, t, J = 6.8 Hz), 3.54-3.61 (2H, m), 3.90 (3H, s), 4.29-4.40 (4H, m), 5.53 (1H, brs), 6.70 (1H, d, J = 8.8 Hz), 6.93 (1H, dd, J = 8.8, 2.4 Hz), 7.03 (1H, d, J = 2.3 Hz), 7.10 (1H, d, J = 2.4 Hz), 7.25-7.32 (2H, m), 7.88 (1H, d, J = 2.8 Hz), 8.00 (1H, brs) |

TABLE 42-continued

| Ex. | Syn | DAT |
|---|---|---|
| 6 | Ex6 | ESI+: 361<br>1H-NMR (DMSO-d6) δ:<br>1.79 (3H, s), 2.76 (2H, t, J = 7.3 Hz), 3.25-3.33 (2H, m),<br>3.67 (3H, s), 4.25-4.44 (4H, m), 5,66 (1H, d,<br>J = 2.3 Hz), 7.09 (1H, d, J = 2.2 Hz), 7.16 (1H, d,<br>J = 11.7 Hz), 7.23 (1H, d, J = 8.4 Hz), 7.47 (1H, d,<br>J = 2.3 Hz), 7.83-7.95 (1H, m), 10.66-10.77 (1H, br) |

TABLE 43

| Ex. | Syn | DAT |
|---|---|---|
| 7 | Ex7 | ESI+: 357<br>1H-NMR (DMSO-d6) δ:<br>1.78 (3H, s), 2.27 (3H, s), 2.70 (2H, t, J = 7.3 Hz), 3.15<br>(2H, dt, J = 6.9, 6.8 Hz), 3.67 (3H, s), 4.19-4.27 (2H,<br>m), 4.31-4.40 (2H, m), 5.65 (1H, d, J = 2.3 Hz), 6.64<br>(1H, dd, J = 8.6, 2.4 Hz), 6.96 (1H, d, J = 2.3 Hz), 7.11<br>(1H, d, J = 8.7 Hz), 7.47 (1H, d, J = 2.3 Hz), 7.87 (1H, t,<br>J = 5.6 Hz), 10.53 (1H, s) |
| 8 | Ex8 | ESI+: 357<br>1H-NMR (DMSO-d6) δ:<br>0.99 (3H, t, J = 7.6 Hz), 2.06 (2H, q, J = 7.6 Hz), 2.76<br>(2H, t, J = 7.4 Hz), 3.25-3.34 (2H, m), 3.67 (3H, s),<br>4.20-4.40 (4H, m), 5.66 (1H, d, J = 2.3 Hz), 6.74 (1H,<br>dd, J = 8.8, 2.4 Hz), 7.05 (1H, d, J = 2.4 Hz), 7.09 (1H,<br>d, J = 2.3 Hz), 7.22 (1H, d, J = 8.7 Hz), 7.47 (1H, d,<br>J = 2.3 Hz), 7.76-7.86 (1H, m), 10.59-10.67 (1H, m) |
| 9 | Ex9 | ESI+: 383<br>1H-NMR (DMSO-d6) δ:<br>2.28 (3H, s), 2.41 (3H, s), 2.54 (3H, d, J = 4.7 Hz),<br>2.62-2.73 (2H, m), 3.07-3.19 (2H, m), 4.24-4.43 (4H, m),<br>5.67-5.81 (2H, m), 6.64 (1H, dd, J = 8.7, 2.4 Hz), 6.83<br>(1H, dd, J = 5.7, 2.4 Hz), 6.90 (1H, d, J = 2.5 Hz), 6.98<br>(1H, d, J = 2.4 Hz), 7.11 (1H, d, J = 8.7 Hz), 8.25 (1H, d,<br>J = 5.7 Hz), 10.49-10.58 (1H, br) |
| 10 | Ex10 | ESI+: 394 [M + Na]+<br>1H-NMR (CDCl3) δ:<br>2.23 (3H, s), 2.57 (3H, d, J = 4.7 Hz), 2.75 (2H, t,<br>J = 6.6 Hz), 3.28 (2H, dt, J = 6.3, 6.4 Hz), 3.68 (3H, s),<br>4.18-4.29 (2H, m), 4.36-4.47 (2H, m), 4.64-4.80 (2H, m),<br>5.63 (1H, d, J = 2.3 Hz), 6.71 (1H, dd, J = 8.7, 2.4 Hz),<br>6.93 (1H, d, J = 2.4 Hz), 7.06 (1H, d, J = 8.7 Hz), 7.10<br>(1H, d, J = 2.3 Hz), 8.40 (1H, s) |

TABLE 44

| Ex. | Syn | DAT |
|---|---|---|
| 11 | Ex11 | ESI+: 354<br>1H-NMR (DMSO-d6) δ: 1.79 (3H, s), 2.39 (3H, s),<br>2.76 (2H, t, J = 7.4 Hz), 3.25-3.32 (2H, m), 4.26-4.32<br>(2H, m), 4.53-4.60 (2H, m), 6.65 (1H, d, J = 8.2 Hz),<br>6.75 (1H, dd, J = 8.7, 2.4 Hz), 6.84 (1H, d, J = 7.3 Hz),<br>7.06 (1H, d, J = 2.4 Hz), 7.10 (1H, d, J = 2.4 Hz), 7.21<br>(1H, d, J = 8.7 Hz), 7.59 (1H, dd, J = 8.2, 7.3 Hz),<br>7.85-7.94 (1H, m), 10.63 (1H, s) |
| 12 | Ex1 | ESI+: 348 |
| 13 | Ex1 | ESI+: 375<br>1H-NMR (DMSO-d6) δ: 1.77 (3H, s), 2.26 (3H, s),<br>2.70 (2H, t, J = 7.3 Hz), 3.10-3.22 (2H, m), 3.67 (3H, s),<br>4.23-4.41 (4H, m), 5.66 (1H, d, J = 2.3 Hz), 7.05 (1H,<br>J = 11.7 Hz), 7.13 (1H, d, J = 8.4 Hz), 7.47 (1H, d,<br>J = 2.3 Hz), 7.80-7.92 (1H, m), 10.59-10.68 (1H, br) |
| 14 | Ex1 | ESI+: 362 |
| 15 | Ex1 | ESI+: 355<br>1H-NMR (DMSO-d6) δ: 0.97 (3H, t, J = 7.6 Hz), 2.04<br>(2H, q, J = 7.6 Hz), 2.15 (3H, s), 2.27 (3H, s), 2.64-2.74<br>(2H, m), 3.09-3.21 (2H, m), 4.21-4.42 (4H, m), 6.01<br>(1H, dd, J = 2.2, 0.4 Hz), 6.58 (1H, dd, J = 8.6, 2.4 Hz),<br>6.90 (1H, d, J = 2.4 Hz), 7.08 (1H, d, J = 8.7 Hz), 7.64<br>(1H, d, J = 2.1 Hz), 7.72-7.83 (1H, m), 10.48-10.58 (1H,<br>br) |

TABLE 44-continued

| Ex. | Syn | DAT |
|---|---|---|
| 16 | Ex1 | ESI+: 402 |
| 17 | Ex1 | ESI+: 334 |
| 18 | Ex1 | ESI+: 368<br>1H-NMR (DMSO-d6) δ: 1.78 (3H, s), 2.28 (3H, s),<br>2.41 (3H, s), 2.66-2.75 (2H, m), 3.10-3.22 (2H, m),<br>4.22-4.44 (4H, m), 6.65 (1H, dd, J = 8.6, 2.4 Hz), 6.83<br>(1H, dd, J = 5.7, 2.3 Hz), 6.90 (1H, d, J = 2.5 Hz), 6.98<br>(1H, d, J = 2.4 Hz), 7.11 (1H, d, J = 8.7 Hz), 7.82-7.92<br>(1H, m), 8.25 (1H, d, J = 5.8 Hz), 10.49-10.59 (1H, br) |

TABLE 45

| Ex. | Syn | DAT |
|---|---|---|
| 19 | Ex1 | ESI+: 352 |
| 20 | Ex3 | ESI+: 344 |
| 21 | Ex3 | ESI+: 373 |
| 22 | Ex1 | ESI+: 359 |
| 23 | Ex5 | ESI+: 385<br>1H-NMR (DMSO-d6) δ: 2.54 (3H, d, J = 4.7 Hz), 2.74<br>(2H, t, J = 7.2 Hz), 3.22-3.38 (2H, m), 3.80 (3H, s),<br>4.26-4.30 (2H, m), 4.31-4.36 (2H, m), 5.70-5.77 (1H,<br>m), 5.81-5.88 (1H, m), 6.75 (1H, dd, J = 8.7, 2.4 Hz),<br>6.78 (1H, d, J = 8.9 Hz), 7.06-7.12 (1H, m), 7.23 (1H,<br>J = 8.7 Hz), 7.46 (1H, dd, J = 9.0, 3.1 Hz), 7.92 (1H, d,<br>J = 3.0 Hz), 10.63 (1H, s) |
| 24 | Ex6 | ESI+: 365, 367 |
| 25 | Ex6 | ESI+: 362 |
| 26 | Ex6 | ESI+: 377 |
| 27 | Ex6 | ESI+: 359 |
| 28 | Ex6 | ESI+: 388 |
| 29 | Ex6 | ESI+: 341 |
| 30 | Ex6 | ESI+: 356 |
| 31 | Ex6 | ESI+: 399<br>1H-NMR (DMSO-d6) δ: 2.28 (3H, s), 2.54 (3H, d,<br>J = 4.7 Hz), 2.68 (2H, t, J = 7.2 Hz), 3.07-3.19 (2H, m), 3.80<br>(3H, s), 4.20-4.38 (4H, m), 5.66-5.83 (2H, m), 6.65<br>(1H, dd, J = 8.7, 2.4 Hz), 6.75-6.81 (1H, m), 6.99 (1H,<br>d, J = 2.4 Hz), 7.11 (1H, d, J = 8.6 Hz), 7.46 (1H, dd,<br>J = 8.9, 3.1 Hz), 7.91 (1H, d, J = 2.7 Hz), 10.48-10.58 (1H,<br>br) |
| 32 | Ex6 | ESI+: 388 |
| 33 | Ex6 | ESI+: 406 |
| 34 | Ex6 | ESI+: 357 |
| 35 | Ex6 | ESI+: 389 |
| 36 | Ex6 | ESI+: 373 |

TABLE 46

| Ex. | Syn | DAT |
|---|---|---|
| 37 | Ex6 | ESI+: 375<br>1H-NMR (DMSO-d6) δ: 1.24 (3H, d, J = 6.6 Hz), 1.80<br>(3H, s), 2.95-3.12 (2H, m), 3.27-3.47 (1H, m), 3.67<br>(3H, s), 4.27-4.34 (2H, m), 4.35-4.41 (2H, m), 5.66<br>(1H, d, J = 2.4 Hz), 7.07 (1H, d, J = 2.3 Hz), 7.16 (1H, d,<br>J = 11.8 Hz), 7.33 (1H, d, J = 8.3 Hz), 7.47 (1H, d,<br>J = 2.3 Hz), 7.85-7.97 (1H, m), 10.68-10.75 (1H, m) |
| 38 | Ex6 | ESI+: 391, 393<br>1H-NMR (DMSO-d6) δ: 1.24 (3H, d, J = 6.6 Hz), 1.80<br>(3H, s), 2.96-3.14 (2H, m), 3.28-3.48 (1H, m), 3.67<br>(3H, s), 4.27-4.35 (2H, m), 4.36-4.43 (2H, m), 5.67<br>(1H, d, J = 2.4 Hz), 7.12 (1H, d, J = 2.3 Hz), 7.34 (1H,<br>s), 7.38 (1H, s), 7.47 (1H, d, J = 2.3 Hz), 7.84-7.98 (1H,<br>m), 10.72-10.80 (1H, m) |
| 39 | Ex6 | ESI+: 359 |
| 40 | Ex6 | ESI+: 402 |
| 41 | Ex8 | ESI+: 371 |
| 42 | Ex8 | ESI+: 379 |
| 43 | Ex8 | ESI+: 375 |
| 44 | Ex8 | ESI+: 397 |
| 45 | Ex8 | ESI+: 389 |
| 46 | Ex8 | ESI+: 402 |

TABLE 46-continued

| Ex. | Syn | DAT |
| --- | --- | --- |
| 47 | Ex9 | ESI+: 390 |
| 48 | Ex9 | ESI+: 417 |
| 49 | Ex11 | ESI+: 418 |
| 50 | Ex11 | ESI+: 433 |
| 51 | Ex11 | ESI+: 374, 376 |
| 52 | Ex11 | ESI+: 389, 391 |
| 53 | Ex11 | ESI+: 385 |
| 54 | Ex11 | ESI+: 370 |
| 55 | Ex11 | ESI+: 374 |
| 56 | Ex11 | ESI+: 389 |
| 57 | Ex11 | ESI+: 358 |

TABLE 47

| Ex. | Syn | DAT |
| --- | --- | --- |
| 58 | Ex11 | ESI+: 369 |
| 59 | Ex11 | ESI+: 354 |
| 60 | Ex11 | ESI+: 380 |
| 61 | Ex11 | ESI+: 382 |
| 62 | Ex11 | ESI+: 409 |
| 63 | Ex11 | ESI+: 330 |
| 64 | Ex11 | ESI+: 340 |
| 65 | Ex65 | ESI+: 361<br>1H-NMR(DMSO-d6)δ:<br>1.79 (3H, s) 2.76 (2H, t, J = 7.3 Hz), 3.22-3.34 (2H, m), 3.67 (3H, s), 4.25-4.43 (4H, m), 5.66 (1H, d, J = 2.3 Hz), 7.09 (1H, d, J = 2.3 Hz), 7.16 (1H, d, J = 11.8 Hz), 7.24 (1H, d, J = 8.4 Hz), 7.47 (1H, d, J = 2.3 Hz), 7.82-7.97 (1H, m), 10.64-10.78 (1H, br) |
| 66 | Ex66 | ESI+: 371<br>1H-NMR(DMSO-d6)δ:<br>0.98 (3H, t, J = 7.6 Hz), 2.04 (2H, q, J = 7.6 Hz), 2.27 (3H, s), 2.70 (2H, t, J = 7.2 Hz), 3.11-3.21 (2H, m), 3.67 (3H, s), 4.17-4.27 (2H, m), 4.30-4.40 (2H, m), 5.65 (1H, d, J = 2.3 Hz), 6.64 (1H, dd, J = 8.6, 2.4 Hz), 6.96 (1H, d, J = 2.4 Hz), 7.11 (1H, d, J = 8.7 Hz), 7.47 (1H, d, J = 2.2 Hz), 7.72-7.84 (1H, m), 10.49-10.57 (1H, br) |

INDUSTRIAL APPLICABILITY

The compound of the formula (I) or a salt thereof is a compound which acts as a peripheral $MT_1$ and/or $MT_2$ receptor agonist, and since it does not exhibit a sleep action when administered at an effective dose in the application of the treatment or prevention of urinary incontinence, it is possible to separate the action on urinary incontinence and the action on the central nervous system disease. Thus, the compound of the formula (I) or a salt thereof can be used as an active ingredient for a pharmaceutical composition for treating or preventing urinary incontinence, and preferably stress urinary incontinence and a mixed type of urinary incontinence.

The invention claimed is:

1. A compound of the formula (I) or a salt thereof:

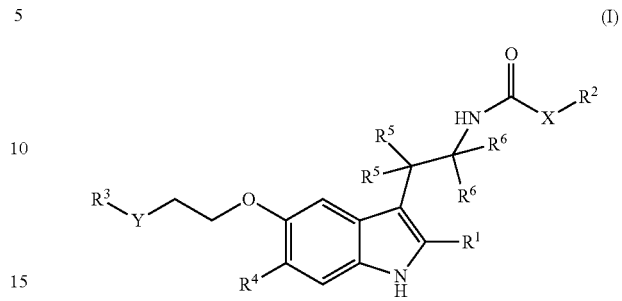

wherein,
$R^1$ is H or $C_{1-6}$ alkyl which may be substituted,
X is a bond, —NH—, or —N($C_{1-6}$ alkyl)-,
$R^2$ is $C_{1-6}$ alkyl which may be substituted,
Y is a bond, —$CH_2$—, —NH—, or —O—,
$R^3$ is 5- to 6-membered heteroaryl which may be substituted, provided that when Y is a bond, $R^3$ may further be —$NR^{31}$—CO—O—$R^{32}$,
$R^{31}$ is H or $C_{1-6}$ alkyl,
$R^{32}$ is $C_{1-6}$ alkyl,
$R^4$ is H, $C_{1-6}$ alkyl which may be substituted, or halogen,
$R^5$s are the same as or different from each other, and are H or $C_{1-6}$ alkyl which may be substituted, and
$R^6$s are the same as or different from each other and are H or $C_{1-6}$ alkyl which may be substituted.

2. The compound or a salt thereof according to claim 1, wherein
$R^1$ is H or $C_{1-6}$ alkyl,
$R^2$ is $C_{1-6}$ alkyl which may be substituted with 1 to 3 halogens,
Y is a bond or —O—, wherein
  (i) when Y is —O—, $R^3$ is 5- to 6-membered heteroaryl having at least one hetero atom selected from a group consisting of O, S, and N, or
  (ii) when Y is a bond, $R^3$ is 5-membered heteroaryl having at least two hetero atoms selected from a group consisting of O, S, and N,
the heteroaryl represented by above (i) and (ii) may be substituted with 1 to 3 substituents selected from a group consisting of $C_{1-6}$ alkyl which may be substituted with 1 to 3 substituents selected from a group consisting of —OH, —O—($C_{1-6}$ alkyl), and halogen; —O—($C_{1-6}$ alkyl); $C_{3-8}$ cycloalkyl; and halogen,
when Y is a bond, $R^3$ may further be —$NR^{31}$—CO—O—$R^{32}$,
$R^4$ is H or halogen,
$R^5$s are the same as or different from each other, and are H or $C_{1-6}$ alkyl, and
$R^6$s are the same as or different from each other and are H or $C_{1-6}$ alkyl.

3. The compound or a salt thereof according to claim 2, wherein
$R^1$ is H or methyl,
X is a bond or —NH—,
$R^2$ is $C_{1-6}$ alkyl which may be substituted with 1 to 3 F,
Y is a bond or —O—, wherein
  (i) when Y is —O—, $R^3$ is heteroaryl selected from a group consisting of pyridyl, pyrazinyl, pyrimidinyl, thiazolyl, pyrazolyl, and isoxazolyl, or (ii) when Y is a bond, $R^3$ is heteroaryl selected from a group consisting of thiazolyl, pyrazolyl, and isoxazolyl, the heteroaryl represented by above (i) and (ii) may be substituted with 1 to 3 substituents selected from a group consisting of $C_{1-6}$ alkyl which may be substituted with 1 to 3 halogens; —O—($C_{1-6}$ alkyl); $C_{3-8}$ cycloalkyl; and halogen, when Y is a bond, $R^3$ may further be —NH—CO—O—$R^{32}$, $R^{32}$ is $C_{1-6}$ alkyl, $R^4$ is H or halogen, and $R^5$ and $R^6$ are the same as or different from each other and are H or methyl.

4. The compound or a salt thereof according to claim 3, wherein $R^2$ is methyl or ethyl, (i) when Y is —O—, $R^3$ is pyridyl or pyrazolyl; or (ii) when Y is a bond, $R^3$ is pyrazolyl, the pyridyl and the pyrazolyl may be substituted with 1 to 3 substituents selected from a group consisting of $C_{1-6}$ alkyl which may be substituted with 1 to 3 halogens and —O—($C_{1-6}$ alkyl), $R^5$s are the same as or different from each other and are H or methyl, and $R^6$s are H.

5. The compound or a salt thereof according to claim 4, wherein (i) when Y is —O—, $R^3$ is pyridyl substituted with one substituent selected from a group consisting of methyl and methoxy, or pyrazolyl substituted with one methyl; or (ii) when Y is a bond, $R^3$ is pyrazolyl substituted with one substituent selected from a group consisting of methyl and trifluoromethyl.

6. The compound or a salt thereof according to claim 5, wherein

X is a bond,

Y is —O—, $R^3$ is pyrazolyl substituted with one methyl, $R^4$ is H or F, and $R^5$ and $R^6$ are both H.

7. The compound or a salt thereof according to claim 1, wherein the compound is selected from the group consisting of:

N-[2-(6-fluoro-5-{2-[(1-methyl-1H-pyrazol-3-yl)oxy]ethoxy}-1H-indol-3-yl)ethyl]acetamide, N-[2-(2-methyl-5-{2-[(1-methyl-1H-pyrazol-3-yl)oxy]ethoxy}-1H-indol-3-yl)ethyl]acetamide, N-[2-(2-methyl-5-{2-[(1-methyl-1H-pyrazol-3-yl)oxy]ethoxy}-1H-indol-3-yl)ethyl]propanamide, 1-[2-(5-{2-[(6-methoxypyridin-3-yl)oxy]ethoxy}-1H-indol-3-yl)ethyl]-3-methylurea, N-[2-(5-{2-[(6-methylpyridin-2-yl)oxy]ethoxy}-1H-indol-3-yl)ethyl]acetamide, N-[2-(6-fluoro-2-methyl-5-{2-[(1-methyl-1H-pyrazol-3-yl)oxy]ethoxy}-1H-indol-3-yl)ethyl]acetamide, N-(2-{2-methyl-5-[2-(3-methyl-1H-pyrazol-1-yl)ethoxy]-1H-indol-3-yl}ethyl)propanamide, and 1-[2-(5-{2-[(6-methoxypyridin-3-yl)oxy]ethoxy}-2-methyl-1H-indol-3-yl)ethyl]-3-methylurea.

8. A pharmaceutical composition comprising the compound or a salt thereof according to claim 7, and a pharmaceutically acceptable excipient.

9. A method for treating urinary incontinence, comprising administering to a subject an effective amount of the compound or a salt thereof according to claim 7.

10. The compound or a salt thereof according to claim 7, wherein the compound is N-[2-(6-fluoro-5-{2-[(1-methyl-1H-pyrazol-3-yl)oxy]ethoxy}-1H-indol-3-yl)ethyl]acetamide.

11. The compound or a salt thereof according to claim 7, wherein the compound is N-[2-(2-methyl-5-{2-[(1-methyl-1H-pyrazol-3-yl)oxy]ethoxy}-1H-indol-3-yl)ethyl]acetamide.

12. The compound or a salt thereof according to claim 7, wherein the compound is N-[2-(2-methyl-5-{2-[(1-methyl-1H-pyrazol-3-yl)oxy]ethoxy}-1H-indol-3-yl)ethyl]propanamide.

13. The compound or a salt thereof according to claim 7, wherein the compound is 1-[2-(5-{2-[(6-methoxypyridin-3-yl)oxy]ethoxy}-1H-indol-3-yl)ethyl]-3-methylurea.

14. The compound or a salt thereof according to claim 7, wherein the compound is N-[2-(5-{2-[(6-methylpyridin-2-yl)oxy]ethoxy}-1H-indol-3-yl)ethyl]acetamide.

15. The compound or a salt thereof according to claim 7, wherein the compound is N-[2-(6-fluoro-2-methyl-5-{2-[(1-methyl-1H-pyrazol-3-yl)oxy]ethoxy}-1H-indol-3-yl)ethyl]acetamide.

16. The compound or a salt thereof according to claim 7, wherein the compound is N-(2-{2-methyl-5-[2-(3-methyl-1H-pyrazol-1-yl)ethoxy]-1H-indol-3-yl}ethyl)propanamide.

17. The compound or a salt thereof according to claim 7, wherein the compound is 1-[2-(5-{2-[(6-methoxypyridin-3-yl)oxy]ethoxy}-2-methyl-1H-indol-3-yl)ethyl]-3-methylurea.

* * * * *